United States Patent
Mitchell et al.

(10) Patent No.: US 6,684,188 B1
(45) Date of Patent: Jan. 27, 2004

(54) METHOD FOR PRODUCTION OF MEDICAL RECORDS AND OTHER TECHNICAL DOCUMENTS

(76) Inventors: Geoffrey C Mitchell, 3847 Olentangy Blvd., Columbus, OH (US) 43214; Douglas D Rudy, 40 W. Lincoln Ave., Westerville, OH (US) 43085

(*) Notice: Subject to any disclaimer, the term of this patent is extended or adjusted under 35 U.S.C. 154(b) by 0 days.

(21) Appl. No.: 08/596,002

(22) Filed: Feb. 2, 1996

(51) Int. Cl.[7] ............................................. G06F 17/60
(52) U.S. Cl. ........................ 705/3; 128/924; 128/925; 345/809; 345/810; 715/506
(58) Field of Search ................ 128/923, 924, 128/925; 345/352, 704, 809, 810; 395/12, 50, 924; 705/2, 3, 4; 707/104, 506, 104.1; 715/506

(56) References Cited

U.S. PATENT DOCUMENTS 3,800,439 A * 4/1974 Sokolski et al. ............. 35/48 B
3,900,961 A * 8/1975 Sokolski et al. ............. 35/48 A (List continued on next page.)

FOREIGN PATENT DOCUMENTS

JP 03-108017 * 5/1991

OTHER PUBLICATIONS

Wu: "A knowledge–based database assistant with a menu–based natural language user–interface"; IEICE Tranactions on Information and Systems, Oct. 1993, vol. E76–D, No. 10, pp. 1276–1287, (Abstract Only).*

Yamazaki et al: "Standard method for describing an electronic patient record template: application of XML to share domain knowledge"; Methods of Information in Medicine, Mar. 200, vol. 39, No. 1, pp. 50–55, (Abstract Only).*

Toshiba; "DYNAPAD T200"; advertisement; (One page), 1994.*

Primus Systems Inc.; "CHARTEM Quickly create Emergency Department Charts"; 910 Boston Post Road Suite 260, Marlborough, Ma 01752; (Three pages), 1995.*

(List continued on next page.)

*Primary Examiner*—Edward R. Cosimano
(74) *Attorney, Agent, or Firm*—Porter, Wright, Morris & Arthur LLP

(57) ABSTRACT

A computer implemented system for the production of medical records, legal documents and other frequently produced semi-technical documents. This is accomplished by generating an intelligent computer-guided interview and the use of serialized scriptable objects. Major program elements include a knowledge base text file, a parse engine, and an execution module. The knowledge base uses a unique rule syntax. The parse engine converts the textual knowledge base file to a compiled binary representation which can then be interpreted by the execution module. The execution module leads the user through the interview by generating a series of questions and presents possible answers in the form of pick lists. The data is recorded with a computer pen and collated into a document file. This file is coded in binary format and can be written to and recalled from disk. If the file is recalled from disk the user can continue to answer questions or change answers previously given. The result is a mobile computing system whereby data is input in a structured format. When the program is executed the user is prompted for answers to questions and, based upon the user's response, the final document can change considerably. Depending upon each answer, the program may change the subsequent questions being asked, change the list associated with a question, change the text being generated, or change the entire structure of the document. The data collected may be also be stored in a database for analysis at a later date. Finally, the data collected is output in a narrative text format which can be tailored according to the traditions and expectations of the user's profession. The program will output the text via a printer or it can be transmitted via electronic means.

3 Claims, 41 Drawing Sheets

U.S. PATENT DOCUMENTS

| | | | | | |
|---|---|---|---|---|---|
| 3,951,062 | A | * | 4/1976 | Abramson | 101/426 |
| 3,960,634 | A | * | 6/1976 | Kempster | 156/277 |
| 4,038,666 | A | * | 7/1977 | Fuller, Jr. | 346/136 |
| 4,190,268 | A | * | 2/1980 | Webster | 282/3 R |
| T998,008 | I4 | | 9/1980 | DeLano, Jr. | |
| 4,733,354 | A | * | 3/1988 | Potter et al. | 364/415 |
| 4,798,543 | A | * | 1/1989 | Spiece | 434/323 |
| 4,835,683 | A | * | 5/1989 | Phillips et al. | 706/10 |
| 4,835,690 | A | * | 5/1989 | Gangarosa et al. | 364/413.13 |
| 4,865,549 | A | * | 9/1989 | Sonsteby | 434/262 |
| 4,869,531 | A | * | 9/1989 | Rees | 283/67 |
| 4,920,499 | A | * | 4/1990 | Skeirik | 364/513 |
| 4,945,476 | A | * | 7/1990 | Bodick et al. | 600/301 |
| 5,006,699 | A | * | 4/1991 | Felkner et al. | 235/472 |
| 5,043,891 | A | * | 8/1991 | Goldstein et al. | 707/531 |
| 5,065,338 | A | * | 11/1991 | Phillips et al. | 706/50 |
| 5,070,478 | A | * | 12/1991 | Abbott | 364/419 |
| 5,101,375 | A | * | 3/1992 | Goldhor | 364/419 |
| 5,111,398 | A | * | 5/1992 | Nunberg et al. | 364/419 |
| 5,128,865 | A | * | 7/1992 | Sadler | 364/419 |
| 5,146,406 | A | * | 9/1992 | Jensen | 364/419 |
| 5,146,439 | A | * | 9/1992 | Jachmann et al. | 369/25 |
| 5,148,366 | A | * | 9/1992 | Buchanan et al. | 364/419 |
| 5,164,899 | A | * | 11/1992 | Sobotka et al. | 364/419 |
| 5,165,030 | A | * | 11/1992 | Barker | 395/500 |
| 5,200,893 | A | * | 4/1993 | Ozawa et al. | 364/419 |
| 5,247,437 | A | * | 9/1993 | Vale et al. | 364/419.19 |
| 5,257,185 | A | * | 10/1993 | Farley et al. | 364/419.19 |
| 5,257,186 | A | * | 10/1993 | Ukita et al. | 364/419.1 |
| 5,265,010 | A | * | 11/1993 | Evans-Paganelli et al. | 364/413.02 |
| 5,267,155 | A | * | 11/1993 | Buchanan et al. | 364/419.14 |
| 5,276,793 | A | * | 1/1994 | Borgendale et al. | 395/148 |
| 5,293,473 | A | * | 3/1994 | Hesse et al. | 395/146 |
| 5,309,359 | A | * | 5/1994 | Katz et al. | 364/419.19 |
| 5,310,997 | A | * | 5/1994 | Roach et al. | 235/375 |
| 5,311,422 | A | * | 5/1994 | Loftin et al. | 364/578 X |
| 5,327,341 | A | * | 7/1994 | Whalen et al. | 364/419.07 X |
| 5,331,554 | A | * | 7/1994 | Graham | 364/419.07 |
| 5,331,555 | A | * | 7/1994 | Hashimoto et al. | 364/419.07 |
| 5,341,469 | A | * | 8/1994 | Rossberg et al. | 395/145 |
| 5,359,509 | A | * | 10/1994 | Little et al. | 364/401 |
| 5,361,202 | A | * | 11/1994 | Doue | 365/600 X |
| 5,367,619 | A | * | 11/1994 | Dipaolo et al. | 707/506 |
| 5,375,204 | A | * | 12/1994 | Motoyama et al. | 395/164 |
| 5,402,504 | A | * | 3/1995 | Bloomberg et al. | 382/9 |
| 5,404,528 | A | * | 4/1995 | Mahajan | 365/650 |
| 5,438,512 | A | * | 8/1995 | Mantha et al. | 395/145 X |
| 5,446,653 | A | * | 8/1995 | Miller et al. | 364/401 |
| 5,452,206 | A | * | 9/1995 | Turrietta et al. | 395/700 X |
| 5,459,827 | A | * | 10/1995 | Allouche et al. | 395/148 |
| 5,463,547 | A | * | 10/1995 | Markowitz et al. | 364/408 |
| 5,475,805 | A | * | 12/1995 | Murata | 395/145 |
| 5,632,007 | A | * | 5/1997 | Freeman | 395/75 |
| 5,657,233 | A | * | 8/1997 | Cherrington et al. | 73/117.2 |
| 6,006,242 | A | * | 12/1999 | Poole et al. | 707/531 |
| 6,289,513 | B1 | * | 9/2001 | Bentwich | 717/106 |
| 2001/0044813 | A1 | * | 11/2001 | Frank | 707/530 |

OTHER PUBLICATIONS

QD Systems; "Great Charts"; 1465 Fourth Street Berkely, Ca. 94710; (order form and sample); (Two pages), 1993.*

Microsoft; "MEDI–Mouse Systems"; 10 W. Terra Cotta Crystal Lake, Il. 60014; (sales brouchure and sample); (Two pages), Oct. 1992.*

WELLSOFT Corp., "HomeEasy Integrated Clinical Management System"; 605 Franklin Blvd, Suite 5 Somerset, NJ. 08873; (Cover and sample); (Two pages), No Date.*

ORCA Medical Systems; "ORCA Clinical Information System (ORCA–CIS)"; 22125 17th Avenue, S.E. Suite 105, Bothell, Wa 98021; (Cover letter and 3 pages of description of the features of ORCA–CIS); (Four pages), Dec. 1995.*

TeleMed RLIS, Inc.; "Emergency Department Patient Documentation Systems" 4319 Medical Drive #131–341 San Antonio, Texas 78229; (Cover letter and description); (Four pages), Sep. 1995.*

BRC Health Care Division Clinical Resources Group; "EmSTAT Clinical Documentation"; 3701 North Lamar, Suite 207 Austin Texas 78705; (cover sheet and two page sample); (Threee pages), Apr. 1993.*

Lancent Technology, Inc.; "Emergency One for Windows Version 3.2"; One Kendall Square, Building 200 Cambridge Ma 02139; (cover letter, description and sample); (Three pages), Oct. 1995.*

Logicare Corp.; "LOGICARE" (advertisement); Logicare Corp. Eau Clair WI.; (One page), No Date.*

Cybermedix Inc; "Cliniplex"; 8230 Old Courthouse Road Suite 300 Vienna Virginia 22182; (Advertisment and sample); (Two pages), 1993.*

PDA MEDical; "Virtual Intern"; PO Box 12353 Aspen Co. 81612; (One page advertisment), No Date.*

Reynolds; One page of description of PRAXIS from Infor*Med Medical Information Systems, 10806 Ventura Boulevard, Suite 2, Studio City California 91604; Physicians and Computers; p. 36, No Date.*

Medicomp Systems; "MEDTRAC The Computerized Patient Chart System"; 14585 Avion Parkway Suite 1000 Chantilly Va. 222021; (Cover sheet and description); (Two pages), No Date.*

Kurzweilai Applied Intelligence, Inc.; "VoiceEM Clinical Management System"; 411 Waverly Oaks Road Waltham Ma 02154; (cover advertisment and sample); (Two sheets), No Date.*

TransQuick; "Voice Quick" 4848 Riverdale Road Atlanta Georgia 30337; (one page advertisement), No Date.*

Wrenn, Keith, et. al., "The Use of Structured, Complaint Specific–Patient Encounter Forms in the Emergency Department", *Annals of Emergency Medicine*, May 1993, p. 805–812, vol. 22.5.

Mellick, Larry B., et. al., editors, "Innovative Charting Can Slash Costs, Bolster Efficiency, Enhance Quality", ED Management, Nov. 1995, p. 121–127, vol. 7:11.

Davis, Dave, et. al., "Changing Physician Performance", *Journal of the American Medical Association*, Sep. 6, 1995, p. 700–705, vol. 274:9.

* cited by examiner

| Input Variable | — 316 |
| Ouput Variable | |
| Ouput Variable | |
| Ouput Variable | — 318 |
| Ouput Variable | |
| Ouput Variable | |
| Ouput Variable | |

| | | |
|---|---|---|
| tobacco | TOB | |
| toes | TOE | |
| tooth | TOO | |
| trauma - level 1 | TR1 | |
| trauma - level 2 | TR2 | |
| trauma - level 3 | TR3 | |
| trauma | TRA | |
| transported by | TRN | ——— 310 |
| introduction | TRO | |
| trauma score | TRS | |
| trivial | TRV | |
| title - Mr./Mrs./Ms. | TTL | |
| treatment | TX | |
| tympanic membrane | TYM | |
| type | TYP | |
| upper arm | UAR | |
| ulcer | ULC | |
| ulnar | ULN | |
| ultimate (last) | ULT | |
| umbilicus | UMB | |
| unit | UNT | |
| upper | UPP | |
| urinary | URN | |
| user | USR | |
| uterus | UTR | |
| upper extremity | UX | |
| unilateral | UNL | |
| visual field | VFD | |
| medications - vitamins | VIT | |
| volar | VOL | |
| vital signs | VS | ——— 314 |
| peripheral vascular | VSC | |
| vessel | VSL | |
| with or without | W/W | |
| WBC | WBC | |
| which | WCH | |
| width | WID | |
| weakness | WKN | |
| wound | WND | |
| wound repair | WR | |
| wrist | WRI | |
| warmth | WRM | |
| xrays | XR | |
| extremity | XT | |
| extended exam | XTD | |
| yes / no | Y/N | |

Fig. 15

240-- [LISTS]
REM \*\*\*\*\*\*\* Lists - Generic \ Multi \ Alphasort \*\*\*\*\*\*\*\*\*\*\*\*\*\*\*\*\*\*\*\*\*\*\*\*\*\*\*\*\*\*\*\*\*\*\*\*\*\*
REM alphabetized NAME=ANA_LAC
336-- SORT=false
ankle
face
finger
foot
hand
head
knee
334-- [NEW]

NAME=ANA_ORN ———————— 312
anterior
338-- posterior\posterior to the
medial
lateral
superior
inferior NAME=COM ———————— 252
abdominal pain
ankle injury
chest pain ———————— 256
eye injury
laceration
neck injury
[MORE]

NAME=DX
SORT=TRUE
acute myocardial infarction
chest pain, noncardiac
costochondritis
fracture
laceration
sprain
strain

Fig. 17A

```
REM ****** Lists - Numbers **********************************************
NAME=029
 0
 1
 2
 3
 4
 5
 6
 7
 8
 9
```

242-- [TEMPLATES]
```
REM ************************ Templates **************************************
  NAME=COM                _____  262
    SUBVAR=#
      LONGNAME "What is the complaint number?"
      LIST 029
      TYPE INFER_ONLY
340--    SUBVAR=IS
      LONGNAME "What is the complaint?"
      LIST COM
    SUBVAR=TYP
      LONGNAME "What is the complaint type?"
      list TYP
      TYPE INFER_ONLY
    SUBVAR=LOC
      LONGNAME "Where is the %COM.TYP% located?"
      list ANA_TOT
    SUBVAR=CLS
      LONGNAME "What is the complaint class?"
      list COM
      TYPE INFER_ONLY
    SUBVAR=AGG
      LONGNAME "Aggravating factors"
      LIST
      TYPE
      DEFAULT
    SUBVAR=ALL
      LONGNAME "Alleviating factors"
      LIST
      TYPE
      DEFAULT
```

Fig. 17B

```
                    SUBVAR=ARR
                      LONGNAME "Means of Arrival"
                      LIST
                      TYPE
                      DEFAULT
                    SUBVAR=ASX
                      LONGNAME "Associated symptoms"
354 ─────────         TYPE MULTSELECTABLE, OMITTABLE
                    SUBVAR=B/U
                      LIST B/U
                      DEFAULT unique
                    SUBVAR=CCS
                      LONGNAME "What were you doing when the %COM.TYP% occurred?"
                      LIST CCS
                      TYPE OMITTABLE
                    SUBVAR=DTL
                      LONGNAME "Do you wish to add more detail?"
                      LIST Y/N
                      DEFAULT no 244 ─────────       [VARS]
                    REM ****************************** Variables ***********************
                    REM alphabetized
                                                          ─── 356
                    NAME=CTRL_PMH
276 ─────────       LIST 029
                    TYPE INFER_ONLY OMITTABLE RATCHET ─────────── 360
                    DEFAULT 0

NAME=MRN
274 ─────────       LONGNAME "Enter the medical record number for this patient"
                    LIST MRN                                  ─── 364
278 ─────────       DEFAULT 00000000
                    TYPE NUMERIC_ENTRY FILENAME 358  ╲              NAME=SEX
      ╲             LIST SEX          ─── 362
       ╲            TYPE INFER_ONLY
       ╱            HELP This is an infer-only variable.
280  ╱              DEFAULT female NAME=WCH_DIG
                    LIST WCH_DIG
                    LONGNAME "Which digit?"

344 ─────────       NAME=COM1 TEMPLATE=COM

NAME=DX1 TEMPLATE=DX
```

Fig. 17C

```
246--  [NODES]
       REM ************************ Nodes **********************************

NAME=DI
370--  TEXT "The patient was "
       VAR DI_DST
       TEXT " in "
376--  VAR DI_CDT
       TEXT " condition. "
       TEXT "Discharge instructions are noted. "

NAME=DX
       SETTEMPLATE DX=DX1
372--  TEXT "\n      "
       NODE DX_QLF
       VAR DX.IS
       TEXT ", "
378--  NODE DX_ICD
       TEXT ", "
       VAR DX.ICD

NAME=RT_HPI
       REM This node gives the routing instructions based upon CLaSs.
342--  IF (COM1.LOC=head) HPI_HI
392--  ELSE IF (COM.TYP=laceration) \SETVARIABLE HPI_TYP\\laceration
393--  ELSE IF (COM.TYP=pain) \SETVARFROMSUM ROS_TOT\ROS_MN\ROS_PAI
       IF ((COM.LOC=ankle)AND(COM.TYP=injury)) HPI_INJ_ANK
388--  ELSE IF ((COM.LOC=knee)AND(COM.TYP=injury)) \ABORT
390--  ELSE IF ((COM.LOC=neck)AND(COM.TYP=injury)) \TEXT " neck injury "

NAME=COM1
384--  SETTEMPLATE COM=COM1
       SETTEMPLATE DX=DX1
394--  DO \SETVARIABLE COM.#\\1
       TEXT "This (age) year old %SEX% presented to the ED with "
380--  IF (COM.G/S=specific) COM_SPF
382--  ELSE IF (COM.G/S=general) COM_GNL
       IF ((COM.FOC=yes)AND(COM.TYP=laceration)) COM_LOC_INJ
       TEXT ". "
       NODE RT_HPI

NAME=CH_COM
       SETTEMPLATE COM=COM1
387--  VAR \ARTICLE COM.IS

NAME=GET_MRN
386--  VAR \NODISP MRN
       TEXT "\n\n"
374--  TEXT "Doe, Jane          %EDP%        ER %MRN%"
```

Fig. 17D

248-- [INFERENCES]
REM ************************ Inferences ******************

REM v v COM.IS v v

316— INFERENCE COM.IS=laceration
I COM.TYP \\laceration\
I COM.FOC \\yes\
I COM.G/S \\specific\
318— I CTRL_LAC\\5\
I COM.CLS \\laceration\
I DX.IS \\laceration\

INFERENCE COM.IS=chest pain
I COM.TYP \\pain\
I CTRL_LAC\\0\

250-- [SECTIONS]
REM ************************ Sections ******************

NAME=DEMOGRAPHICS
398-- DISP=NO
GET_MRN
SEX

NAME=ED PHYSICIAN NOTE

NAME=TIME DICTATED

NAME=CHIEF COMPLAINT:
CH_COM

NAME=HISTORY OF PRESENT ILLNESS
COM1
366-- COM2
COM3

NAME=ALLERGIES

NAME=CURRENT MEDICATIONS

NAME=PAST MEDICAL HISTORY
PMH

NAME=REVIEW OF SYSTEMS
CTRL_ROS

Fig. 17E

NAME=PHYSICAL EXAMINATION
CTRL_LAC_FST
CTRL_SHO_L
CTRL_SHO_R
CTRL_ELB_L
CTRL_ELB_R
CTRL_KNE_L
CTRL_KNE_R
CTRL_ANK_L
CTRL_ANK_R
CTRL_LAC_LST

NAME=LAB

NAME=X-Rays

NAME=PROCEDURES
SET_CTRL_PRC
CTRL_WR_LAC1

NAME=DIAGNOSTIC IMPRESSION
DX

NAME=INSTRUCTIONS

TITLE="            Anywhere Hospital\n            100 Main Street.\n
        ╲
         ╲ 372

Fig. 17F

Anywhere Hospital

100 Main Street.

Anytown, U.S.A. 99999

Doe, Jane     Marcus Welby, M.D.     ER 00000000

EMERGENCY DEPARTMENT PHYSICIAN NOTE

TIME DICTATED

CHIEF COMPLAINT     chest pain

HISTORY OF PRESENT ILLNESS     This 58 year old female presented to the ED with chest pain.

\*\*\*\* HPI entered by MD here \*\*\*\*

Other associated symptoms include palpitations, diaphoresis, and PND.

ALLERGIES     The patient is allergic to sulfa.

CURRENT MEDICIATIONS     Current medications include Bactrim and Inderal.

PAST MEDICAL HISTORY     The past medical history is positive for The past medical history is positive for COPD and diabetes. Previous surgeries include PTCA.

\*\*\*\* Social history and Family history inserted here \*\*\*\*     518

516

REVIEW OF SYSTEMS     The review of systems was positve for *nausea* and *cough*. The review of systems was negative for *fever, shortness of breath, wheezing, abdominal pain, vomiting, or diarrhea*.

What is the patients occupation?

| | |
|---|---|
| [NONE]<br>assembly line worker<br>carpenter<br>clerical worker<br>disabled<br>EMT<br>executive<br>factory worker<br>fast food attendent<br>hospital aide<br>kitchen worker<br>laboror<br>landscaper<br>maid<br>nurse<br>paramedic<br>resturant server<br>roofer<br>sales person<br>secretary<br><br>OK | ER  12345678                         410<br><br>EMERGENCY DEPARTMENT PHYSICIAN NOTE<br><br>TIME DICTATED<br><br>CHIEF COMPLAINT          chest pain<br><br>HISTORY OF PRESENT ILLNESS    This (age) year old<br>female presented to the ED with  chest pain.<br><br>**** HPI entered by MD here ****<br><br> Other associated symptoms include <br>claudication and DOE.<br><br>CURRENT MEDICIATIONS       Current<br>medications include Insulin and Proventil inhaler.<br><br>SOCIAL HISTORY            The patient is<br>employed as a  . |

552 (points to EMT)

Smart Chart Editor - ROS064.SCT    Thu Dec 07 12:44a
File Edit View Chart Options Help

Template specific review of systems

** HPI entered by MD here **

Other associated symptoms include 
claudication, DOE, and orthopnea.

CURRENT MEDICIATIONS       Current
medications include Insulin.

SOCIAL HISTORY            The patient is
employed as a  clerical worker.        ——— 556

Smart Chart Editor - ROS064.SCT    Thu Dec 07 12:49a
File Edit View Chart Options Help

Template specific review of systems

| | |
|---|---|
| [NONE]<br>abdominal pain<br>bloody stools<br>cough<br>diarrhea<br>lower extremity symtoms<br>nausea<br>orthpnea<br>pain with breathing<br>vomiting<br><br>558 | **** HPI entered by MD here ****<br><br> Other associated symptoms include <br>claudication and DOE.<br><br>CURRENT MEDICIATIONS       Current<br>medications include Insulin, Prednisone, and<br>Proventil inhaler.<br><br>SOCIAL HISTORY            The patient is<br>disabled. |

Fig. 36

Doe, Jane  
ER 22233322

Marcus Welby, M.D.

Chief complaint:   twisted ankle   562

HPI  
This 18 year old female presented to the ED with a *twisted ankle*. This occurred as a result of an inversion injury. The patient also complained of *knee pain*. There was no history of trauma to the knee.   564

566

568

PE   The *left knee* was nontender. There was no tenderness localized over the *right knee* joint. There was no swelling of the right knee . No effusion was noted. There was no instability noted. There was mild tenderness localized over the lateral aspect of the *left ankle* joint. There was mild swelling of the lateral aspect of the left ankle . No effusion was noted. There was no instability noted. The *right ankle* was nontender .

Doe, Jane  Susan Lewis, M.D.
ER 70000001                                              574

ED PHYSICIAN NOTE                                    576

PROCEDURES
Wound Repair:  The skin surrounding the wound was painted with
*betadine* and draped in a sterile fashion.  The wound was
infiltrated locally with *1% xylocaine* without epinephine.  The
wound was then scrubbed with *sterile saline*.  The wound was
inspected for foreign material and none was seen.  The skin was
reapproximated with *4-0 nylon* suture.  6 sutures were placed in
interrupted fashion.  The wound was treated with *neosporin* and
dressed with a *kling* dressing.

580

Doe, Jane            Marcus Welby, M.D.
ER 70000001

582

PROCEDURES
Wound Repair:  The skin surrounding the wound was painted with
*soap and water* and draped in a sterile fashion.  The wound was
infiltrated locally with *1% novacaine* without epinephine.  The
wound was then scrubbed with *clean tap water*.  The wound was
inspected for foreign material and none was seen.  The skin was
reapproximated with *4-0 silk* suture.  6 sutures were placed in
interrupted fashion.  The wound was treated with *sulfa antibiotic*
and dressed with a *gauze* dressing.

Fig. 38

Anywhere Hospital
100 Main Street.
Anytown, U.S.A. 99999

Doe, Jane                    Trapper John, M.D.          ED 70000001
ED PHYSICIAN NOTE TIME DICTATED
CHIEF COMPLAINT:              laceration HISTORY OF PRESENT ILLNESS    This 27 year old female presented to the ED
with a laceration of her left hand. The laceration occurred from broken
glass while washing dishes. This occurred about 1 hour ago. There is no
numbness or weakness noted. There is no sensation of a foreign body. Her
last tetanus immunization was less than 5 years ago.

PHYSICAL EXAMINATION          Examination of the left hand demonstrates a 2
centimeter linear laceration over the lateral border. The wound is oblique
in orientation. Distal neurovascular function is normal. This full thickness
wound appears essentially clean.

PROCEDURES
Wound Repair: The skin surrounding the wound was painted with betadine and
draped in a sterile fashion. The wound was infiltrated locally with 1%
xylocaine without epinephine. The wound was then scrubbed with sterile
saline. The wound was inspected for foreign material and none was seen. The
skin was reapproximated with 4-0 nylon suture. 6 sutures were placed in
interrupted fashion. The wound was treated with neosporin and dressed with a
kling dressing.

DIAGNOSTIC IMPRESSION         laceration, left hand, 882

DISPOSITION                   The patient was discharged from the ED in
satisfactory condition. Discharge instructions are noted.

| Customer ID | First Name | Last Name | Sex | Chief Complaint | COM LOC | COM DUR | Diagnosis |
|---|---|---|---|---|---|---|---|
| 30001234 | Smith | Bob | M | Chest pain | chest | 1 | MI |
| 30001235 | Doe | John | M | laceration | hand | 1 | hand laceration |
| 30001248 | White | Jack | M | abdominal pain | abdomen | 12 | Appendicitis |
| 30001999 | Black | Susan | F | laceration | face | 1 | facial laceration |
| 59001234 | Doe | Mary | F | laceration | hand | 1 | hand laceration |
| | | | | | | 0 | |

METHOD FOR PRODUCTION OF MEDICAL RECORDS AND OTHER TECHNICAL DOCUMENTS

FIELD OF INVENTION

This invention relates generally to the production of technical documents and more particularly to the production of electronic medical records by mobile health care workers.

BACKGROUND OF INVENTION

As the entire world struggles through the transition from the industrial to the information age, the need for information and document management is felt throughout the workplace. Medicine can be considered a prototypical field where that need is acutely felt. In medicine, as in many other fields, the increasing risk of litigation, the presence of third party payers, and the increasing complexity of the work have lead to a mountainous burden of paperwork.

Modern patients lament the fact that physicians don't spend as much time with them as Marcus Welby would have. Few realize that most doctors spend at least as much time on paperwork as they spend directly with a patient for any given encounter. Superficial, cursory physician/patient encounters are not acceptable but unfortunately the work of documentation must be done and we cannot turn back the clock. Our only hope of improving this situation is to make the documentation process more efficient.

Structured Documentation

Through the years, individuals have sought to improve the process of documentation in several different ways. Kempster (U.S. Pat. No. 3,960,634, 1976) sought to simplify the process by adding adhesive sheets to an existing record, thus adding small amounts of information to a preexisting record in an incremental fashion. Sonsteby (U.S. Pat. No. 4,865,549, 1989) attempted to add structure to the documentation process. She utilized color coded adhesive labels to organize the document and eliminate omissions of crucial data elements.

The concept of structured documentation is not new. It should be considered simply a way to practice good medicine. It is often estimated that in medicine the correct diagnosis is revealed in the patient's history as often as 90% of the time. A structured interview is simply a way of enhancing the quality of care by reminding the physician not to omit important details. An example of structured documentation is noted in one of the earliest textbooks still in widespread use today (The Early Diagnosis of the Acute Abdomen, Sir Zachary Cope, 1921, 15th ed., pg 21). The concept is still being refined and improved today (Wrenn, et al.: The use of structured, complaint-specific patient encounter forms in the emergency department. *Annals Emergency Medicine*, May 1993; 22:805–812). Unfortunately these attempts all comprise written manual methods. Attempts to incorporate information age technologies to bear in the medical profession have thus far been less than successful.

Visual Images

Others sought to improve upon the documentation process by adding visual representations to their documents. Assuming "a picture is worth a thousand words" these individuals felt that they could improve the documentation process and avoid long winded descriptions. Abramsom (U.S. Pat. No. 3,951,062, 1976) accomplished this by using a rubber stamp which consisted of an outline of a particular anatomic structure. Rees (U.S. Pat. No. 4,869,531, 1989) accomplished the same goal by using adhesive backed stickers with drawings of anatomical structures that could be mounted on the chart. In either case the physician could then add the particular elements of the individual case to the outline or scaffold drawing. This could be accomplished in a relatively accurate fashion without the need for great artistic talent on the part of the user.

Mobile Workers

Fuller (U.S. Pat. No. 4,038,666, 1977) attacked a different problem. How could documentation be performed by a mobile worker? His device, known as a "portable medical data recorder" consisted of a roll of paper on two rollers encased in a device with a window for writing. When the paper in the window was filled, the paper could be advanced and a fresh writing surface exposed.

Dictation/Transcription

All of these were manual methods that required written input on the part of the user. Documentation was still very time consuming and produced only a physical paper record. Eventually some modern technological methods were applied in order to increase the efficiency of the professional user who needed to produce documentation. The most important of these was dictation and subsequent transcription. We are not aware of any patents relating to standard transcription methods even though they are in widespread use. The method is quite obvious i.e. a tape recorder and a typist. Jachmann and Sweet (U.S. Pat. No. 5,146,439, 1992) developed a more advanced form which they described as "digital dictation" but this was a technical innovation that had little impact on the individual performing the dictation or on the final document produced.

Dictation/transcription systems are in widespread use today. These systems have several drawbacks:

1) Compared to writing or typing, there is a clear time saving for the individual doing the dictating. However, this is simply represents a cost shifting mechanism. Transcribing is still very labor intensive and skilled transcriptionists are still in short supply in most areas.

2) Similar scenarios require repetitive duplicate dictation on the part of the dictating user. Some have attempted to overcome this drawback by combining transcription with the use of "boiler plate" methods. A boiler plate is where a variable is inserted in the context of some preexisting text. This is seem in the mail merge functions of many word processors.

3) Transcription does not even come close to the dream of the "Electronic Medical Record" so often discussed among health care planners. There are three reasons for this.

a) Transcription still produces a paper document in most cases. Although most modern transcription centers use computerized word processors the transcribed documents are almost always printed to paper before there are reviewed or distributed. The electronic file produced by the transcription software is rarely transmitted or archived in its electronic state. The paper document is often reproduced by photocopying or transmitted by facsimile machine and this requires additional time and effort. If one then wishes to transmit or store the paper document by electronic means, it must first be converted, usually by means of an optical scanner. This adds a redundant step to the work.

b) Even if they are scanned into electronic documents, most documents are simply scanned as a graphical image not as text files. Optical character recognition is an additional step that still requires an operator to proofread and correct the document.

c) Even if the document is scanned, converted and stored in a text based format, it is still very difficult to retrieve data for outcome studies (very important for health planning). This is because the data is not input in any sort of systematic format. The same physical symptom could be known as chest pain, chest pains, substernal pain or pains in the chest. Complex search engines must be utilized to extract any meaningful data from free text documents. This can be very labor intensive as well.

Computerized Medical Records

As computers have become common place over the past decade it is only logical that they would be utilized to address these problems. Buchanan and Dowdle (U.S. Pat. No. 5,148,366, 1992) developed "computer-assisted documentation system for enhancing or replacing the process of dictating and transcribing". They themselves described their technique as a "boiler plate" methodology. It is much like the process commonly described as "mail merge" in word processing systems. Buchanan and Dowdle (U.S. Pat. No. 5,267,155, 1993) later improved upon their system by adding a relational database.

Computerized Speech recognition

One of the leaders in the field of document production over the past few years has certainly been Kurzweil AI, Inc. Kurzweil Al has been a dominant market player in the field of medical record production. Investigators at Kurzweil hold at least ten patents. Nine of these relate specifically to voice recognition apparatus which is the main strength and emphasis at Kurzweil. Only one patent by Goldhar (U.S. Pat. No. 5,101,375, 1992) relates to the actual structure or production of the document itself and this only in a limited way. His patent related to the use of a database table lookup scheme for providing binding and capitalization of text strings in a report. This is a function that is accomplished in different ways by other programs that provides narrative output, e.g. grammar checking programs. The methods developed at Kurzweil have certainly been very innovative and useful for those who can utilize speech recognition in their work. However there remain several shortcomings to Kurzweil's and other speech recognition systems.

1) Speech recognition is suitable for radiologists, pathologists, and attorneys who do their work at a fixed desk but is not suitable for mobile workers. Thus for these workers who move about constantly, speech recognition introduces the same redundancy and duplication into the flow of work as standard dictation. Mobile workers must take notes and then return to a central dictating station to dictate a formal record from their notes.

2) The advantage of speech recognition is that the document is produced immediately but a disadvantage is that the speaker must speak much slower than with standard dictation. This time consuming drawback can often offset the other advantages of the system.

3) The currently available systems available from Kurzweil and others offer speech recognition as their only advantage. These systems actually utilize the same basic boiler plate approach advanced by Buchanan and Dowdle. The voice recognition systems are used to simply fill in the blank holes in preprinted text. Many documentation needs in the world today are simply far too complex for such an approach.

Expert Systems

As computers became more powerful and sophisticated, expert systems were developed and applied to a variety of problems. DeLano (US DEFPUB T998008, 1980) developed a method for decision tree analysis. This involved the calculation of probabilities and weighted decisions. Gangarosa, Patrick, Futtu James M., and Green Andrew S. (U.S. Pat. No. 4,835,690, 1989) developed an integrated expert system for medical imaging, set-up, and scheduling. This system was used for organizing x-rays. It had nothing to do with producing medical charts. Skeirik (U.S. Pat. No. 4,920,499, 1990) developed an expert system with natural-language rule updating. Spiece (U.S. Pat. No. 4,798,543, 1989) used an expert system to perform interactive training in the military. Bodick, et al. (U.S. Pat. No. 4,945,476, 1990) developed an interactive expert system and method for creating and editing a knowledge base for use as a computerized aid to the cognitive process of diagnosis. This program was used to assist in making diagnoses in a pathology depart by means of cataloging and accessing case features and photographs. Little, et al. (U.S. Pat. No. 5,359,509, 1994) applied an expert system to the process of health care payment adjudication of claims and payments.

More recent inventions include Loftin, Wang, Baffes and Hua's (U.S. Pat. No. 5,311,422, 1994) development of general purpose architecture for intelligent computer-aided training and Mahajan (U.S. Pat. No. 5,404,528, 1995) who developed a scripting system. Although there is a great deal of interest in the application of expert systems in the medical field, most of this interest is directed toward using such systems to arrive at a diagnosis. We are aware of no case where an expert system has been used as an aid to the rapid production of technical documents.

Automated Data Entry

Sokolski (U.S. Pat. Nos. 3,800,439, 1974 and 3,900,961, 1975) developed a document reading, data input technology known as the SCAN-TRON™ method of data entry. This method comprises a specially designed paper form used for the purpose of collecting data for computerized analysis. Scan-Tron™ sheets are filled in by the individual being surveyed. The user must fill in a small box or circle with a pencil mark. A common use for Scan-Tron™ sheets is in the grading of standardized examinations. These data entry sheets can then be read by a special electronic device and the data fed directly into a computer. This bypasses the expensive step of a human data entry clerk. The disadvantage to these scannable sheets is that they are not at all fast or expeditious for the original user. There are two reasons for this. One, the Scan-Tron™ answer sheet must be a distinct second sheet of paper. The user must look back and forth between the two sheets and be very cautious not to lose his place. The other reason the use of these sheets is very slow is that the small boxes or circles must be filled in very precisely. Generations of students have been warned that if the are not cautions and diligent in the filling out of their answer sheets their grade will suffer. This degree of attention to detail is time consuming.

Patented Pen Computer Processes

One other patent is of some interest. Roach and Hollander (U.S. Pat. No. 5,310,997, 1994) secured a patent for an automated order and delivery system. Although this patent comes from a totally different field, it is an example of a computerized process utilizing a pen based computer to improve the flow of work in a given industry.

Emergency Medicine—State of the Art

The state of the art of documentation in the emergency department was recently reviewed in a monthly newsletter directed toward emergency department managers and directors (ED Management, American Health Consultants, Nov. 1995). This article begins by pointing out that "producing medical charts quickly and thoroughly has always been a challenge for emergency physicians". They proceed to review the currently available technology. Standard dictation/transcription is in widespread use. However chart turnaround time is often too slow and tracking and editing charts is cumbersome. These authors note that voice recognition is improving, but remains too slow for widespread acceptance. Voice recognition systems in use today are uniformly combined with template systems. This same ED Management article points out that a Smithsonian Technology award was recently granted to a company called TRANSQUICK™ (Atlanta, Ga.) for developing a methodology to smoothly toggle from computerized speech recognition to a standard medical transcriptionist.

The authors of this review then turned their attention to what they felt was the best currently available computerized documentation system, EMstationm™ (Datamedic Clinical Systems, Waltham, Mass.). EMstation™ is a template driven system that incorporates many useful reminders for billing and reimbursement. It also manifests a very creative use of the Windows GUI with regard to the use of color and placement of items on the screen. However, at its core this product remains essentially a template driven system. Any template system is still limited to the initial document structure provided by the template. The user simply fills in the blanks. These systems can be customized but this still requires someone; the user, designer, or domain expert, to envision each and every potential scenario in advance. Each and every potential scenario or combinations of scenarios must be programmed as a separate template. Thus, to use medical examples it would be logical to create a template for nausea and vomiting as these two complaints are logically related. However, the complaints of ankle sprain and shortness of breath have no logical connection although they are both very common. Creating templates for combinations of even two or three common complaints would be essentially impossible.

Shortcomings of Currently Available Systems

Other drawbacks of currently available template computerized charting systems are noted.

1. These devices are designed to enhance reimbursement. They are structured for physician data entry. They make no allowance for shared data or data entry by less experienced and/or less highly paid individuals.
2. Whatever inference might be present in these systems is a function of the structure of the template. As such it is unidirectional, that is to say, it begins with the patient's complaint. We are aware of no other software system which allows for bi-directional inference, i.e., working backward from a diagnosis. This corresponds to the that way doctors often think when they produce charts, especially if the charts are produced after the fact.
3. These systems are desktop which have been modified and customized for different types of input such as mouse and pen. The result is a system that often requires such hybrid input in order to function effectively. These programs are not designed for use by the mobile worker with data input from a pen only.
4. A corollary to number 3 above is that the currently available systems too often require keyboard entry to complete or modify the data. Many systems depict the user typing on a laptop computer. Again this is not suitable for the mobile worker.
5. Those emergency department, medical record systems which do a better job of facilitating data entry, such as CLINPLEX™, produce documents in the form of an outline or telegraphic speech. These documents are similar to the short hand notes people make to themselves in the course of their work. Handwritten doctor's notes have long been considered unintelligible. This is true for two reasons. One is the tradition of sloppy handwriting. The other is the shorthand and technical abbreviations. Because of these two problems, dictated notes are now considered the standard of practice for insurance reimbursement and legal documentation. Computer systems that produce abbreviated text output only address half of the problem.
6. Currently available systems generally do not incorporate any reminder function to improve the quality of care provided. The authors of the ED management review point out that a computer system should be able to help remind a doctor not to prescribe penicillin if the patient is allergic. Some systems do incorporate some reminders but they are still template based. For this reason these reminder functions when they do exist don't really respond to the actual unique data input such as a patient's drug allergy. They simply respond to the current template.
7. In the systems currently available the number of user definable fields is usually quite limited and not programmable by the end user. Consequently there is no means for the user to collect much personally useful data for the purpose of outcomes analysis.

Background Summary

The authors of this recent review of currently available technology (ED Management) conclude, "there is no cutting-edge technology in transcription . . . we're not even close to that." Furthermore in regard to template systems such as EM STATION™ they conclude "The one deficit I see with all of these systems is they are motivated by improving reimbursement . . . ED's will need something to make them more efficient, improve outcomes and keep them out of trouble". These authors seem to view currently available computer systems as less than successful. They then turn their attention to a review of other methodologies for improving the documentation process. These include the use of court stenographers and dictation assistants.

Thus the reader will see in the following sections that the present invention combines some features that have been known. These features are part of the process of producing documents, managing information and practicing medicine. The reader will also see that the present invention, Computer-assisted Documentation (CaD), succeeds in computerizing these processes, combining a vast array of useful functionality into one smooth process. CaD furthermore adds new functionality to produce a unique and powerful tool to create technical documents.

SUMMARY AND OBJECTS

Accordingly, the overall object and advantage of our invention is to assist the professional or technical expert in producing documentation or records on a daily basis. There is a great need for a more efficient means of managing information and producing records. Our invention is a means of automating the production of such documents. This is accomplished by several means as outlined below.

Speed and Efficiency

It is, therefore, the first major object of this invention to provide a method to produce documents more efficiently.

Rapid Documentation

One advantage of our invention is that mechanically it is simply a faster way to record information. It is faster because data is recorded by quick taps of a pen on a computer screen. These pen strokes are translated to words or sentences in the completed document. Older methods such as writing or dictating are much slower because they require the operator to generate each and every word individually.

Decreased Number of Steps

It is a further object of the invention to increase the efficiency of the process by reducing the number of steps required by eliminating unnecessary and redundant procedures. The means by which this is accomplished is outlined in more detail in the operation of the preferred embodiment.

Shorthand Documentation

It is yet a further object of the invention to increase efficiency of the documentation process by providing the expert user a means of recording data in a shorthand form. When menu selections are made, this can produce various forms of text output. Knowledge base rules can be used to generate grammatically correct phrases and sentences from a single pen click. The inference function of the program can be programmed by the domain expert so that single choices produce longer text fragments. These text fragments can contain variables which are inferred or defaulted according to the user's personal preference. An example might be the description of some surgical procedure that is frequently performed in the same manner or a document such as a will which is frequently produced in a similar fashion.

Expert Extender

It is still a further object of the invention to provide increased efficiency by enabling an expert extender (i.e., nonexpert) to perform some expert functions in a more accurate way. The knowledge base rules can be written so as to incorporate the knowledge of the domain expert into the computer program. The knowledge base can be programmed at the user level in much the same way that a spread sheet program can be written for a specific application. This knowledge base can then be parsed into a reusable program. The nonexpert individual is then guided through the interview process in a structured and controlled fashion simply by answering the questions as they appear on the computer screen. Thus our invention has the advantage of increasing efficiency by freeing the expert to spend more time in decision making, i.e., actually using his/her expertise. The expert user is relieved of redundant documentation tasks and assistants can be utilized in a more cost effective manner. One example of the application of this feature might be to allow less technically proficient individuals to staff a computer help desk.

Multiple Simultaneous Documents

It is still a further object of the invention to provide increased efficiency by allowing the user to produce multiple documents concurrently. Although a user can actually only work on one document at a time, incomplete documents may be saved to disk and later restored. Once a document is restored, the user can move forward and continue to answer questions or go back and change answers previously given to questions. This can be accomplished with written records but is very difficult to do with speech recognition. This requires extra specific effort to communicate to the transcriptionist what changes are to be made. Thus our invention has the advantage of better harmonizing with the way some individuals really work. This feature is essential for certain professions such as emergency medicine where physicians always care for multiple patients simultaneously.

Multiple Contributors to the Same Document

A corollary object and advantage of the invention is to allow a means for multiple workers to contribute to different parts of the same document. Examples of this function include medical records where technicians might record the vital signs and doctors and nurses might each make their own contributions to the record. In the production of standardized accounting report different individuals might each make their own contributions to the final document.

Bi-directional Inference

It is still a further object of the invention to provide increased efficiency by the use of a concept known as "bi-directional inference". Some of the efficiency of CaD is due to the process of inference, i.e., the program allows the value of a variable to be set or determined by the previous selection of another variable. An important and unique feature of the CaD software is that inference can operate in a reverse direction. That is, the reverse of the normal flow of the document and reverse of the apparent thinking process of the user. This is an essential component of the CaD program. It is particularly useful in the expert mode of the preferred embodiment.

In the medical setting, particularly in the emergency department, a physician is able to make a correct diagnosis much more quickly he or she might be able to document the reasoning processes. Bi-directional Inference allow the user to enter some "bottom line" information, in this case a diagnosis, and the CaD system will infer appropriate information throughout the document. This inferred information can then be edited by the user. This process dramatically increases the efficiency of the CaD system. This function is absent in template based systems. As a simple example of how this works consider the fact that a diagnosis of a "heart attack" almost always implies that an EKG was obtained and demonstrated a "heart attack". A template which starts from the beginning complaint of "chest pain" can make no such assumption.

Furthermore complaint based templates can never be specific enough. A chief complaint of "shortness of breath" may mean asthma in a child, anxiety in a young adult but is very likely to signify a heart attack or other heart disease in an elderly person. The advantage of bi-directional inference according to the preferred embodiment is that it corresponds to the way physicians often actually perform their documentation. A physician may arrive at a diagnosis very quickly. The medical record should reflect how the physician arrived at that diagnosis.

Electronic Format

It is still a further object of the invention to provide increased efficiency by producing documents in an electronic format. Handwritten, checklist and most dictation systems used today produce paper documents. There is a great deal of talk and interest in the "electronic medical record". Although most transcription systems use a word processor and produce an electronic file, the far more common practice is to produce a paper document first. Then extra steps are taken to change the document back to an electronic format by scanning or faxing. This is usually necessary because with transcription the user cannot the edit the document in real time as it is being produced (typed). One more advantage of this invention is that because the document can be edited by the original producer in real time, it can immediately be saved or transmitted in electronic format. Thus this invention will allow users to move much closer to the dream of the "paperless office".

Accuracy and Professionalism

It is, therefore, the second major object of this invention to provide a method to produce documents which are more accurate, complete and professional.

Professional Appearance

An object and advantage of this invention is to provide a means of producing charts which are more professional in appearance than those produced by most other methods. High quality documents can be produced with transcription systems but this requires the extra steps of proofreading, editing and retyping. By the appropriate use of the rule syntax in the knowledge base, this invention allows the incorporation of the user's expertise and grammar rules to influence the structure and content of the document. The user's expertise can include the traditional way to organize a document according to the user's profession or according to local custom. Correct spelling and grammar can be built into the knowledge base in advance by the user. The result is a high quality textual report in narrative or prose form. Accurate, concise and readable documents are very important and useful in today's world with increased risk of litigation. This type of document is especially useful in the medical profession where reimbursement by third party payers is based upon the written medical record. Also, according to the preferred embodiment, the CaD program is used to produce accurate medical records. This is advantageous because doctors are particularly known for illegible hand writing. According to the preferred embodiment these documents are created in a narrative or prose format. This feature is useful in a wide variety of fields where the documents once produced, will be read by nontechnical persons.

Individualized Documents

It is another object of the invention to provide a method to provide documents which are more professional in terms of their variety and individuality. Unlike boiler plate methods which can be fast and efficient but result in a document which is very limited or even amateurish, this invention has the advantage of producing documents which are unlimited in their variety. This can be accomplished because the knowledge base syntax rules allow the users input to change the structure and content of the final document in several ways. A simple syntax for the nodes or potential branches in the knowledge base structure allows for essentially unlimited (billions) numbers of possible variations in the final document. In addition to this variability there are the dynamic changes that can occur at runtime. Depending upon the user's input several changes can occur. The subsequent questions can change. The list of potential answers to the questions can change. The text output can change or the actual structure of the document could change.

It is still a further object and advantage of the invention to provide a professionalism and variety in document production due to the fact that the knowledge base script language is not bound to the language or customs of a particular profession. It can be reused across many different fields.

Graphic Images

It is another object of the invention to provide increased accuracy by means of incorporating pictures and diagrams into documents. The advantage of this function is illustrated by the well known saying "a picture is worth a thousand words". The incorporation of visual or graphic images is difficult with any currently available methods. It can easily be accomplished with hand written records but hand writing is otherwise the most cumbersome and inefficient method available. Drawings cannot be easily incorporated into documents produced by checklists, transcription or newer speech recognition systems.

Increased Accuracy

It is another object of the invention to provide a method to produce more accurate documents. This is accomplished because the knowledge base can be programmed in such a way that the user is intelligently guided through an interview. The final document thus produced is more accurate and complete because the user is reminded not to omit certain questions. The user could also be reminded to take a certain action. At first glance it would seem that this function would be most useful to the nonexpert user. However, this ability would actually be of tremendous value to the expert user as well. In a review of the world's literature on the value of continuing medical education for physicians, Davis (JAMA, 1995) found that reminder systems were by far the most effective means of positively changing physician behavior. This invention has the advantage of enabling the expert user or supervisor to incorporate such reminder systems into the day to day work of the regular users.

Mobile Documentation

It is, therefore, the third major object of this invention to provide a means of documentation for the mobile professional. One advantage of this invention is that because it is portable, the user would not be tied down to a desk, Dictaphone or fixed computer but would be free to move about unencumbered. User input is collected via a hand held computer with pen input device and this computer can be connected to a printer through a wireless network.

Concurrent Documentation

It is, therefore, also an object of the invention to provide a means whereby this documentation can occur in real time while the user is actually performing his job rather than after the fact. If the user is forced to postpone documentation until some later time then there is increased risk of forgetting crucial bits of information before the documentation is completed. Real time documentation has the advantage of increased accuracy because the user has the pertinent facts readily available.

It is, therefore, the forth and final major object of this invention to provide a method of data collection and management. This is useful in two ways.

Data Collection for Outcome Analysis

It is, therefore, an object of this invention to provide a method of data collection for use in outcome's analysis. In our world today there is a great deal of pressure to measure outcomes and evaluate the effectiveness of what we do. The most difficult aspect of this in most situations is the actual collection of adequate data. Usually this requires hiring someone to retrospectively review the appropriate documents. An alternative method is to take a dictated record and scan it into electronic format using optical character recognition. A complex search engine is then utilized to extract any meaningful data. Both of these methods are expensive and time consuming. Many times the records in question do not even contain the information being sought. None of the currently available methods of documentation are very good at organizing and retrieving data. Hand written and free text dictation offer no control over the data elements. These methods depend solely upon the operator to include the proper information. Check list systems with preprinted forms are the best currently available attempts to address this problem. These systems are fast, efficient and potentially complete at collecting data. Retrieving the data is another matter. These systems still require a human reviewer/data entry clerk. The alternative is to use a scannable answer sheet which requires very careful attention to detail. In this case the advantage of speed and efficiency is lost because these sheets cannot be filled in quickly.

The advantage of this invention is that each data element is structured in the form of a pick list and stored as a variable. The appropriate data elements are collected in real time as the work is being performed. The user is prompted for data elements he might otherwise have forgotten. Although this program is not based upon a database or internally structured as a database, an interface allows the user to specify that the contents of any variable be translated to a database field. Thus the user can decide which data elements are to be collected and saved for future analysis. This information can then be analyzed retrospectively using commercially available database programs.

A further advantage if the present invention is that the number of user definable fields is unlimited. Variable (field) names can be created by the domain expert/knowledge base programmer. The data collection and analysis process can be individualized.

Data Collection for Scientific Research

It is, therefore, an object of this invention to provide a method of data collection for use in performing scientific research. Once a user decides what questions should be asked, these questions can be programmed into the knowledge base and asked repeatedly in the appropriate context. Thus computer assisted documentation has rather obvious application to field research in sociology and politics. Perhaps less obvious is the advantage of this methodology in such fields as clinical medicine where the research is extraneous to the ongoing task of patient care. In this situation the program could prompt the user to ask the appropriate question or remind the user that a given patient is a suitable candidate for a research protocol. In either case the necessary data elements would be recorded during the course of the patient's care and would be retrievable, if necessary, for research purposes.

Ultimate Object

The overall object and advantage of this invention is to liberate the expert to greater utilization of his or her expertise. Freed from the drudgery of documentation these individuals could use their time more effectively. Perhaps the clearest advantages can be seen in health care which has so preoccupied the public eye in the past few years. Patients idealize the physicians of the past and their caricatures such as Marcus Welby and the Norman Rockwell paintings. Patients lament the fact that today's physicians seem too rushed and busy to spend enough time with them. However, these physicians of the past were never depicted spending hours on paperwork. This is the crucial difference. By utilizing this invention physicians could spend more time with patients. Thus physician's time could be utilized more efficiently and health care costs should decrease.

Up until now people have only talked and dreamed of the "paperless office". Others have utilized complex, redundant technologies in an attempt to convert paper documents to an electronic format. CaD represents a quantum leap forward in the technology of record keeping and document management. The advantages of this invention are by no means limited to health care applications. This invention can be effectively utilized wherever an expert individual is called upon to record and interpret data which is then recorded in the form of individual documents. This invention is of particular advantage in any situation which requires a relatively structured interview.

DRAWING FIGURES

FIG. 15 is an example of a naming convention used in the preferred embodiment.

FIG. 17a is the first of six pages an abbreviated knowledge base (KB) file illustrating many aspects of the knowledge base syntax.

FIG. 17b is the second page of the abbreviated knowledge base file.

FIG. 17c is the third page of the abbreviated knowledge base file.

FIG. 17d is the fourth page of the abbreviated knowledge base file.

FIG. 17e is the fifth page of the .abbreviated knowledge base file.

FIG. 17f is the sixth page of the abbreviated knowledge base file.

FIG. 28 is a sample of a document produced which demonstrates complex variable manipulation using the \SETVARFROMSUM and VARCONVERSE commands.

FIG. 36 is a series of screen snapshots which depict altered text output demonstrating context specific grammar changes.

FIG. 37 is a sample document demonstrating context specific changes in the structure of the document.

FIG. 38 is a sample document demonstrating expert mode with personal preferences selected by inference.

FIG. 41 is an example of a simple but complete document according to the preferred embodiment.

FIG. 42 is a screen snapshot which depicts an example of data recalled in database for analysis.

REFERENCE NUMBERS

Figure 1:
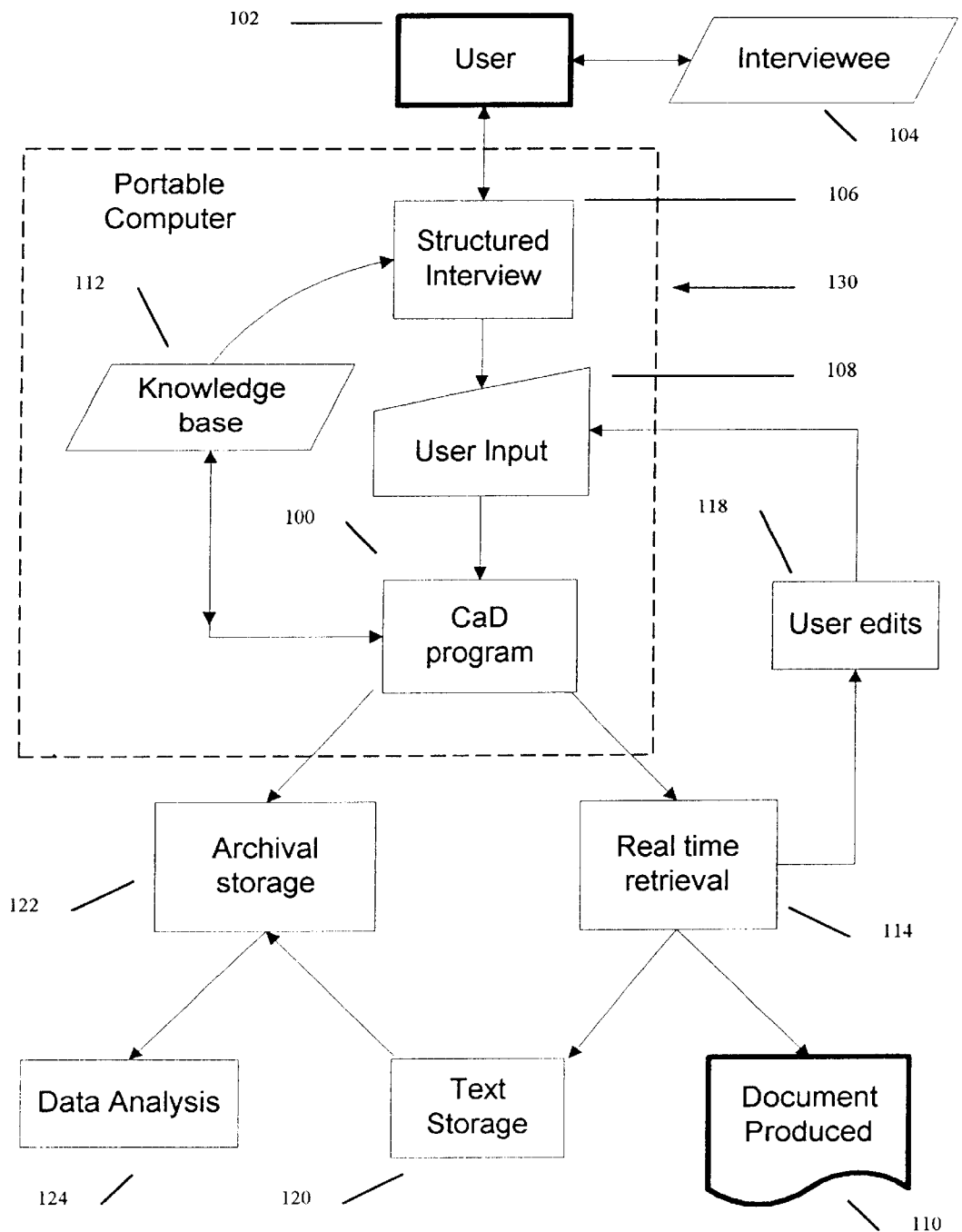
FIG. 1 is a flow chart illustrating an overview of the process of computer-assisted documentation.

| Ref. # | Description | FIG. # |
| --- | --- | --- |
| 100 | complete CaD program | 1, 44 |
| 102 | User, e.g. physician | 1, 6, 43, 44, 45 |
| 104 | Interviewee, e.g. patient | 1, 44, 45 |
| 106 | structured interview process | 1 |
| 108 | user input | 1 |
| 110 | document produced - end result | 1, 6, 44, 45 |
| 112 | binary knowledge base file | 1, 5, 6, 44 |
| 114 | real time retrieval (SCT files) | 1 |
| 118 | user editing process | 1 |
| 120 | text file storage - TXT files | 1 |
| 122 | archival storage - TXT, SCT, DB files | 1, 6 |
| 124 | data analysis | 1 |
| 130 | hand-held computing device | 1, 2 |
| 132 | desktop computing device | 1, 2 |
| 134 | wireless LAN transmitter/receiver | 2, 3, 4 |
| 140 | central processing unit - CPU | 3, 4 |
| 142 | read only memory - ROM | 3, 4 |

-continued

REFERENCE NUMBERS

| Ref. # | Description | FIG. # |
| --- | --- | --- |
| 144 | random access memory - RAM | 3, 4 |
| 146 | mass storage device - hard disk drive | 3, 4 |
| 148 | keyboard input device | 3 |
| 150 | mouse input device | 3 |
| 152 | computer monitor - display screen | 3 |
| 154 | printer device | 3 |
| 156 | LCD screen/digitizeddigitalized input device | 4 |
| 158 | pen input device | 4 |
| 200 | knowledge from domain expert | 5 |
| 202 | syntax language definitions | 5 |
| 204 | ASCII knowledge base file | 5 |
| 208 | parse engine | 5 |
| 210 | persistent objects - POs | 5, 6 |
| 212 | binary code format definitions | 5 |
| 214 | parse module of CaD editor program | 5, 6 |
| 216 | execution module of CaD editor program | 6 |
| 218 | knowledge base manager | 6 |
| 220 | view manager | 6 |
| 222 | display manager | 6 |
| 224 | object manager | 5, 6 |
| 226 | inference manager | 6 |
| 228 | reusable document file - SCT file | 6 |
| 231 | chart (document) persistent object | 7 |
| 232 | section persistent object | 7 |
| 233 | node persistent object | 7 |
| 234 | text persistent object | 7 |
| 235 | rule persistent object | 7, 43 |
| 235 | node rules | 43 |
| 236 | list persistent object | 7 |
| 237 | variable persistent object | 7 |
| 238 | variable set persistent object | 7 |
| 240 | Kbknowledge base syntax - [LISTS] division | 8, 17a, 43 |
| 242 | Kbknowledge base syntax - [TEMPLATES] division | 8, 17b |
| 244 | Kbknowledge base syntax - [VARS] - variable division | 8, 17c |
| 246 | Kbknowledge base syntax - [NODES] division | 8, 17d |
| 248 | Kbknowledge base syntax - [INFERENCE] division | 8, 17e, 43 |
| 248 | Inferences | 43 |
| 250 | Kbknowledge base syntax - [SECTIONS] division | 8, 17e, 43 |
| 252 | list name | 9, 17a |
| 254 | list sort flag | 9, 17a |
| 256 | sample list/list contents | 9, 17a |
| 262 | template name | 10 |
| 264 | template subvariables | 10 |
| 268 | VAR name | 11, 42 |
| 270 | variable attribute - value | 11, 42, 43 |
| 272 | variable attribute - state | 11 |
| 274 | variable attribute - longname | 11, 17c |
| 276 | variable attribute - associated list | 11, 17c |
| 278 | variable attribute - default value | 11, 17c |
| 280 | variable attribute - help text | 11, 17c |
| 282 | variable attribute - type | 11 |
| 284 | modal dialog data entry form - MR # | 12 |
| 286 | numerical entry buttons | 12 |
| 288 | numerical display box | 12 |
| 290 | "OK" - enter button - MR # modal dialog entry | 12 |
| 292 | node - name | 13 |
| 294 | node execution - line by line | 13, 43 |
| 300 | nodal program control - straight transfer | 14 |
| 302 | nodal program control - conditional branch | 14 |
| 304 | nodal program control - return of control | 14 |
| 306 | nodal program control - transfer to | 14 |
| 310 | typical 3 letter abbreviation | 15 |
| 312 | compound name syntax | 17a, 43 |
| 312 | node name syntax | 43 |
| 314 | commonly accepted abbreviation | 15 |
| 316 | inference table - input variable | 16, 17e |
| 318 | inference table - output variable | 16, 17e |
| 334 | [NEW] example of a list keyword | 17a |
| 338 | menu text\output text | 17a |
| 340 | subvariable name line | 17b |

-continued

REFERENCE NUMBERS

| Ref. # | Description | FIG. # |
|---|---|---|
| 342 | example of a simple rule in a node | 17d |
| 344 | template definition | 17c |
| 354 | variable - TYPE = MULTSELECTABLE | 17c |
| 356 | variable - TYPE = OMITTABLE | 17c |
| 358 | variable - TYPE = INFER_ONLY | 17c |
| 360 | variable - TYPE = RATCHET | 17c |
| 362 | variable - TYPE = NUMERIC_ENTRY | 17c |
| 363 | variable - TYPE = DRAWING | |
| 364 | variable - TYPE = FILENAME | 17c |
| 366 | list of nodes to executed as a section | 17e |
| 370 | simple text output | 17d, 43 |
| 372 | \n = insert carriage return | 17d |
| 374 | %VAR% variable substitution in text fragment | 17d |
| 376 | VAR = insert variable value | 17d |
| 378 | routine node redirection | 17d |
| 380 | IF rule | 17d |
| 382 | ELSE rule | 17d |
| 384 | SETTEMPLATE variable set reassignment | 17d |
| 386 | VAR \NODISP variable option | 17d |
| 387 | \ARTICLE | 17d |
| 388 | \ABORT action | 17d |
| 390 | \TEXT action | 17d |
| 392 | \SETVARIABLE command | 17d |
| 393 | \SETVARFROMSUM command | 17d |
| 394 | DO \action syntax | 17d |
| 398 | section - display flag | 17e |
| 400399 | document title definition | 17f |
| 404 | title bar with file ID | 18, 21 |
| 406 | menu bar | 18, 21 |
| 408 | tool bar | 18, 21, 24 |
| 410 | prompt window | 18, 21, 24, 25, 36 |
| 412 | parse from text button | 18 |
| 414 | File menu - parse from text menu selection | 19 |
| 416 | execute Chart menu - interview mode | 20 |
| 417 | execute Chart menu - edit mode | 20 |
| 419 | execute Chart menu - expert mode | 20 |
| 420 | execute Chart menu - document sections | 20 |
| 422 | execute (run) program (currently) loaded KB | 21 |
| 424 | toggle between interview mode &and edit mode | 21 |
| 426 | omit current question button | 21 |
| 428 | open drawing window button | 21 |
| 430 | list window with active pick list | 18, 21, 24 |
| 432 | "OK" button for quick pen input | 18, 21, 24, 25 |
| 434 | text edit window | 18, 21, 24 |
| 436 | edit button - text edit mode | 18, 21 |
| 438 | standard windows scroll bar | 21 |
| 440 | print file button | 21 |
| 442 | text edit button - green check = question answered | 22 |
| 444 | text edit button - green question, optional | 22 |
| 446 | text edit button - omitted question | 22 |
| 448 | text edit button - red question, mandatory answer | 22 |
| 450 | User menu - use to log in, open dialog | 23, 24 |
| 452 | log in dialog box | 23 |
| 454 | log in button | 24 |
| 456 | log out button | 24 |
| 458 | d/c interview and return to edit mode | 24 |
| 502 | pick list with chest pain selected | 25 |
| 504 | text output of "chest pain" in chief complaint | 25 |
| 506 | text output of "chest pain" later in HPI | 25 |
| 512 | gastrointestinal symptoms include nausea | 26 |
| 514 | respiratory symptoms include cough | 27 |
| 516 | Chart section = "Review of Systems" | 28 |
| 518 | example of \SETVARFROMVAR command | 28 |
| 520 | example of VAR \CONVERSE command | 28 |
| 522 | flow chart question - chief complaint | 29 |
| 524 | flow chart question - mechanism of injury? | 29 |
| 526 | flow chart question - which seat? | 29 |
| 528 | flow chart question - location of laceration? | 29 |
| 530 | flow chart question - laceration mechanism? | 29 |
| 532 | chief complaint answer = neck injury | 30 |
| 534 | mechanism answer = motor vehicle accident | 31 |
| 536 | chief complaint answer = laceration | 323 |
| 538 | which seat answer = driver's | 332 |
| 540 | location answer = hand | 34 |
| 542 | mechanism answer = broken glass | 35 |
| 552 | "occupation" pick list | 36 |
| 554 | variable longname prompt window | 36 |
| 556 | selection = clerical worker | 36 |
| 558 | selection = disabled | 36 |
| 562 | complaint #1 = twisted left ankle | 37 |
| 564 | complaint #2 = right knee pain | 37 |
| 566 | left knee exam - minimal | 37 |
| 568 | right knee exam - detailed | 37 |
| 570 | left ankle exam - detailed | 37 |
| 572 | right ankle exam - minimal | 37 |
| 574 | Dr. Lewis - younger doctor | 38 |
| 576 | Dr. Lewis' preferences | 38 |
| 580 | Dr. Welby - older doctor | 38 |
| 582 | Dr. Welby's preferences | 38 |
| 584 | text annotation, drawing window | 39, 40 |
| 586 | keyboard overlay, pen input device | 39 |
| 588 | drawing template | 40 |
| 590 | clear button | 40 |
| 592 | cancel button | 40 |
| 594 | "OK" (enter) button | 40 |
| 598 | record definitions (filenames) | 42 |
| 610 | impact of user selections | 43 |
| 620 | document structure | 43, 44 |
| 632 | medical history | 44, 45 |
| 634 | physical examination findings | 44, 45 |
| 636 | diagnosis | 44 |
| 638 | clinical judgment of physician | 44 |
| 654 | medical traditions | 44 |
| 656 | physician's past experience &and training | 44 |
| 658 | local hospital rules | 44 |
| 672 | secondary user - RN | 44 |
| 674 | secondary user - technician | 44 |
| 676 | minor historical details | 44 |
| 702 | take notes | 45 |
| 704 | sit down &and dictate | 45 |
| 706 | transcription | 45 |
| 708 | dictated note | 45 |
| 710 | repeat similar information in each note | 45 |
| 712 | information gathered by staff members | 45 |
| 714 | fax transmission | 45 |
| 716 | optical scanner | 45 |

DETAILED DESCRIPTION OF THE PREFERRED EMBODIMENT

An Overview of the Process—FIG. 1

FIG. 1 shows an overview of the process of computer-assisted documentation according to the present invention and abbreviated as CaD. This invention comprises a scriptable object system 100 for generating and running intelligent computer-based interviews 106. Essential elements include a user 102, an expert 200, and the computer-assisted documentation software itself 100. The software must be loaded into a suitable computer 130 as outlined below. In the preferred embodiment, the process includes an individual being interviewed 104. This individual 104 serves a source of new and unique data to be recorded to produce a document 110.

CaD allows knowledge domain experts 200 to create knowledge base (KB) text files 204. These files are then compiled into binary knowledge base files 1112 by the software. This binary knowledge base (KB) file 112 is then used to direct the program to prompt the user for information 106 and produce text 110 based on the answers received. When the program executes, it prompts 106 the user for answers to questions. The original knowledge base file 112 is reused to produce scaffolds for new documents. The modified file 112 may be saved to disk 146 and restored, in which case the user 102 can continue to answer questions, or change answers 118 previously given to questions. Finally, the CaD software will output a report in textual format either to disk 120, FIG. 6 or printed as a usable hard copy document 110. The CaD program will output data in a variety of formats and archived for later use 122. This data may be analyzed 124 at some later time for the purpose of research or outcomes analysis. It may also be retrieved for billing or legal purposes.

Figure 2:
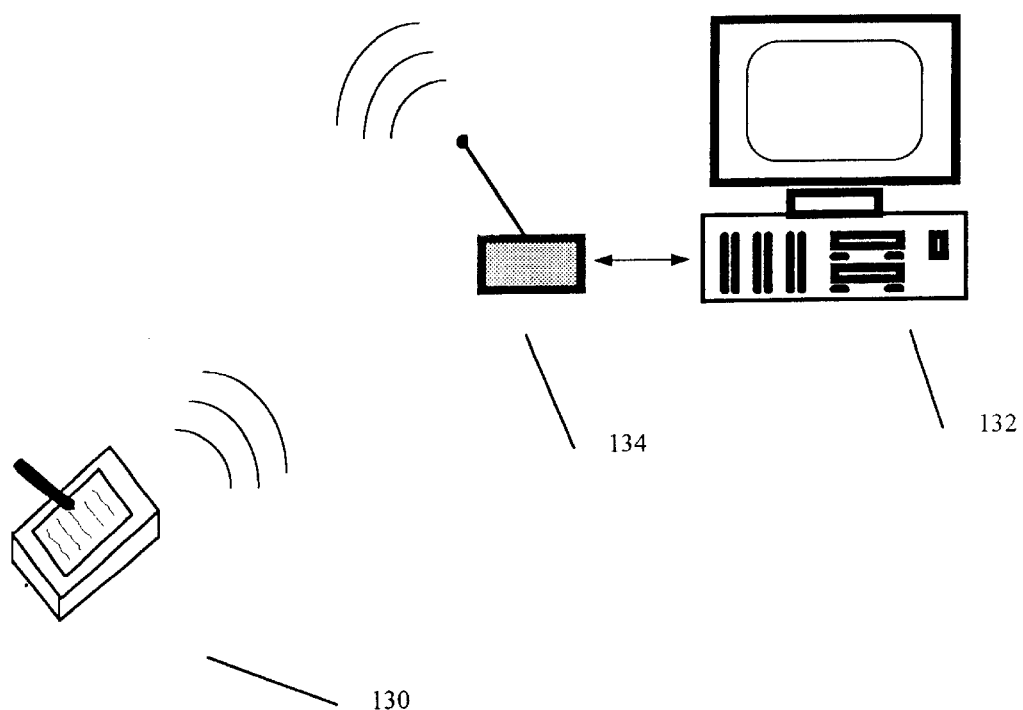
FIG. 2 shows a schematic of wireless LAN transmission between the two computing devices.
Figure 3:
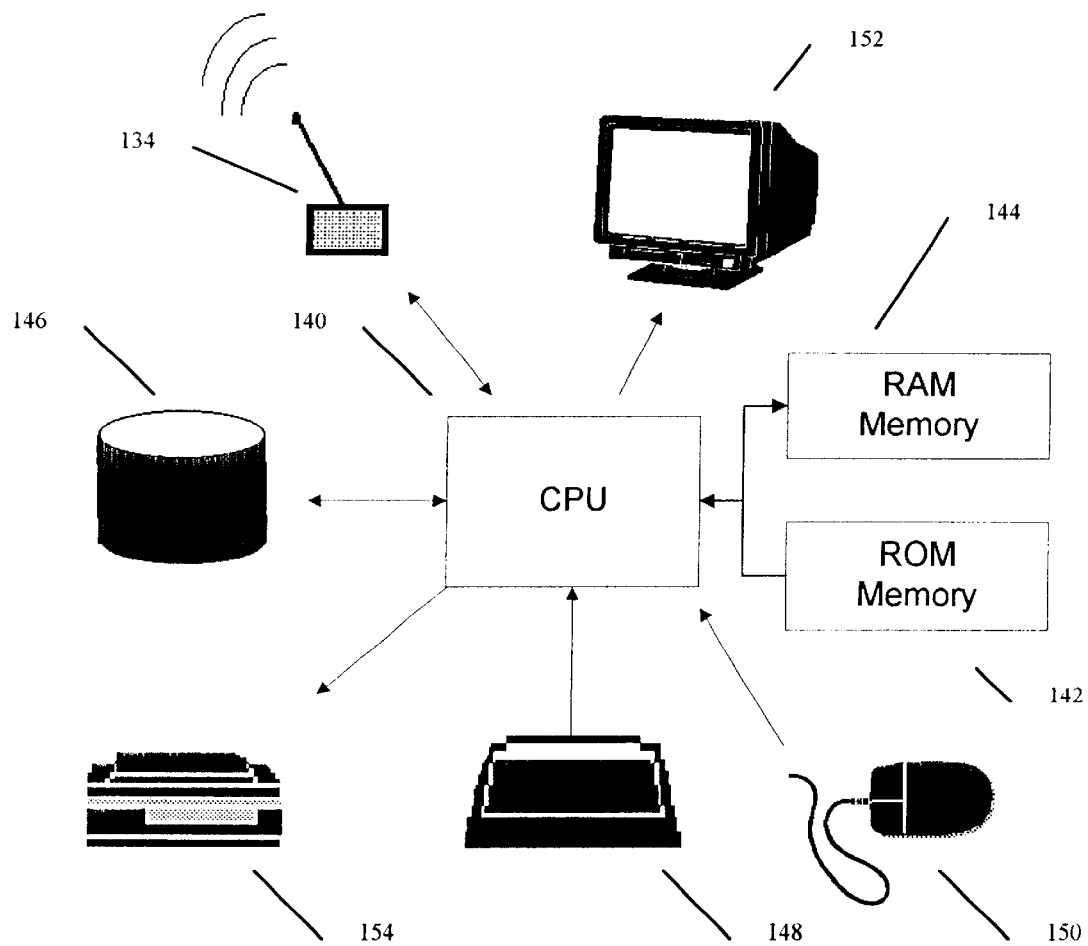
FIG. 3 depicts a typical system configuration for a desktop computing device.

Hardware—FIGS. 2, 3

FIG. 2 shows an overview of the hardware configuration of an apparatus according to the present invention. The crucial piece of hardware is a hand-held tablet computer 130 with a pen interface. Such units are commercially available from several manufacturers including FUJITSU™, IBM™, DAUPHIN™, BADGER™, NORAND™, PANASONIC™, TELXON™, TELEPAD™, and others. According to the preferred embodiment, the hand-held unit communicates with a desktop computer 132 via a wireless LAN (local area network) 134.

FIG. 3 shows the typical configuration of desktop personal computer equipment such as an IBM PC or a PC-compatible computer. In the preferred embodiment computing equipment 132 includes a CPU 140 such as an 80486-processor operating at 66 MHz or greater. The CPU 140 executes program instructions such as operator selected applications programs stored in RAM memory 144 or specialized functions such as start-up programs or BIOS stored in ROM memory 142. Computing equipment 132 further includes a wireless local area network interface 134 that provides an interface to a local area network whereby the computing equipment 132 can communicate with the hand-held mobile unit 130. Computing equipment 132 further includes a monitor 152, a keyboard 148 and a mouse 150 for allowing operator manipulation and input of information. Mass storage memory 146, such as a fixed disk or a floppy disk drive, is accessible to the CPU 140. Mass storage 146 typically includes stored program instruction sequences such as an instruction sequence according to the invention. Other information and data processing programs may be stored in mass storage device 146 as well. Data may also be stored on mass storage memory 146 as desired by the operator. The desktop computer 132 connects to a suitable printer 154 for output of text. A standard laser printer with a resolution of at least 300 dpi would be suitable.

Figure 4:
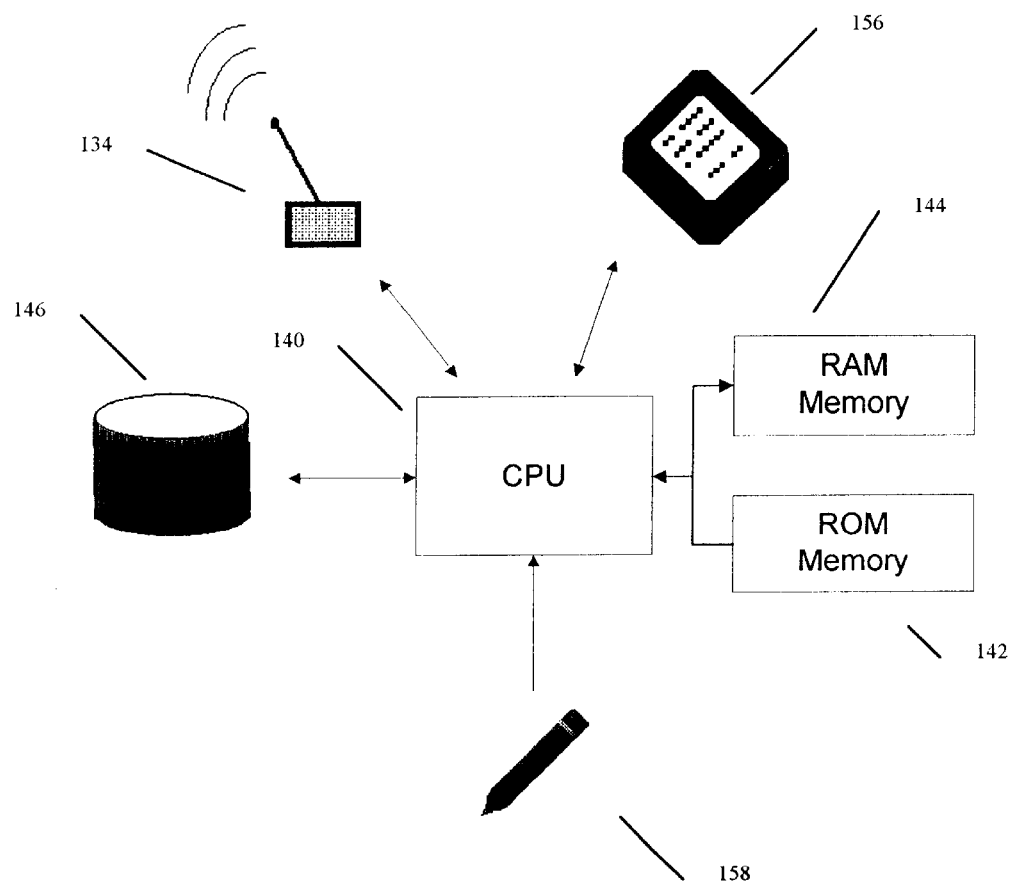
FIG. 4 depicts typical system configuration for a handheld computing device.

FIG. 4 shows the similar configuration of the hand-held computer 130. This computer would also be an IBM PC-compatible computer. Computer 130 includes a CPU 140 such as an 80486-processor operating at 50 MHz or greater. The RAM 144, ROM 142, wireless LAN or WAN 134 are all essentially the same as outlined above. Significant differences between the two computers include the fact that the hand-held unit 130 has no mouse 150 or printer 154. In place of the mouse is the pen 158 designed to transmit an electromagnetic impulse to the specially designed LCD screen 156. This screen is an integral part of the hand-held unit 130 and replaces a conventional monitor 152 but it also serves as an input device. Consequently, no keyboard 148 is used for data entry. The pen 158 is functionally almost identical to a mouse. Mass storage memory 146, consists of a fixed drive of at least 340 Mbytes, accessible to the CPU 140. There is no floppy drive in the hand-held unit. As in the desktop unit, and like most computers, the mass storage 146 includes stored program instruction sequences including the computer-assisted documentation program.

Figure 5:
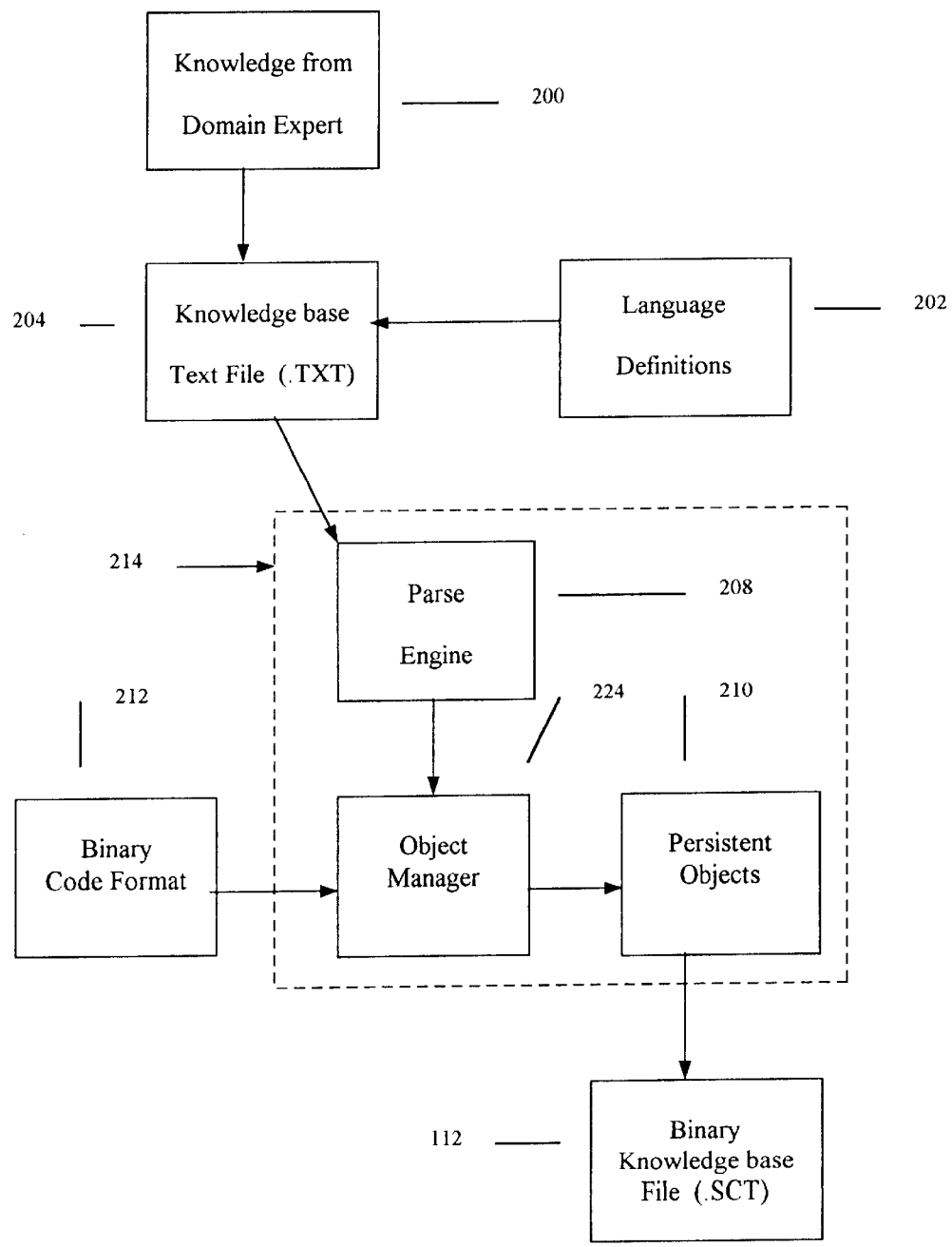
FIG. 5 is a flow chart which illustrates the parse routine whereby a binary knowledge base file is produced from an ASCII knowledge base file.
Figure 6:
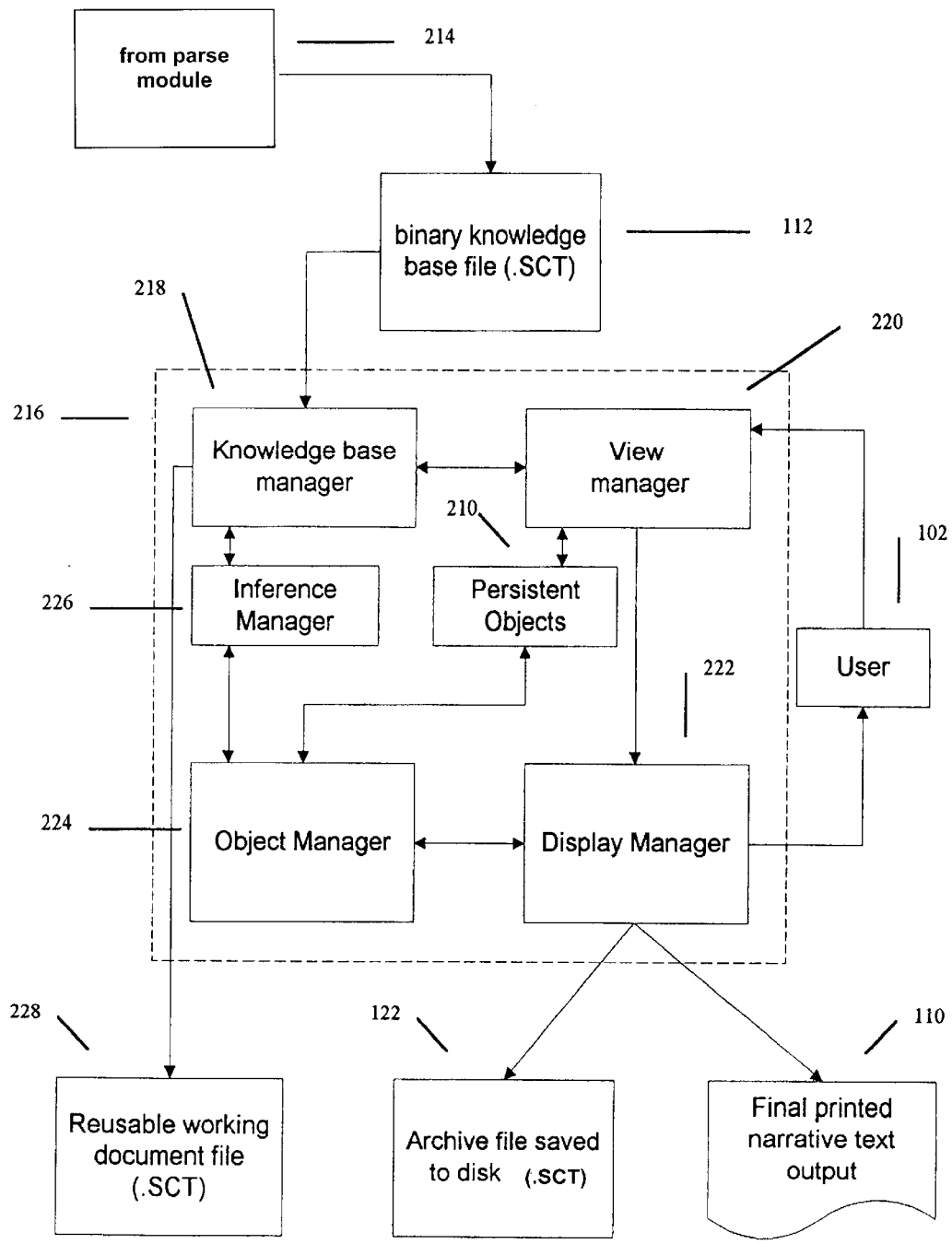
FIG. 6 is a modular flow chart depicting the components of the run-time execution routine.

An Overview of Software Function—FIGS. 5, 6

The structure of the CaD software 100 reflects the fact that the program must be executed in two stages. FIG. 5 outlines the first stage, the parsing of the knowledge base file 204. The expertise of a given domain expert 200 is used to create a knowledge base file 112 that can be reused multiple times. Later the CaD program is executed by a user 102 who may be the original expert or another (nonexpert) individual. At this later point in time the execution of the program serves to guide the user through an interview 106 and facilitate the recording and output of data in a specific organized fashion. FIG. 6 illustrates the execution phase of this process.

FIG. 5 is a flow chart illustrating the components of the preliminary or preparatory portions of the CaD program 214. This preliminary activity culminates in the parsing of the knowledge base file 112. It can be seen in FIG. 5 that this process begins with a domain expert 200. This individual's expertise is translated into a knowledge bags text file 204 according to the syntax in the language definitions 202. The notion of a scripting language is certainly not new. This particular knowledge base language and syntax are, however, newly created. What is unique is the degree to which this language allows dynamic control and redirection of text and variables during the execution phase of document production. Unique features of this language include the combination of standard procedural language constructs for flow control, variable assignment, query, grouping, and indirect reference. These features are also combined with built-in facilities for constructing inference relationships between the value (or content) of a variable and other variables. This inference can change the value of the subsequent variables or the lists associated with the second variable. Inference can also directly affect the text as it is displayed and output to the final document. Variables also control the way a user is prompted for new material. The details of the knowledge base language definition are outlined in a subsequent section. Further details concerning the function of the program are found in the appropriate section of the specification.

There are two parts of the complete CaD editor program 100, the parse module 214 and the execution module 216. These two modules are outlined in FIGS. 5 and 6 respectively. After the domain expert 200 has produced a knowledge base text 204 file written in the CaD knowledge base language 202, this file is processed by the parse engine producing a binary knowledge base file 112. This binary executable knowledge base file contains CaD persistent objects (POs). POs 210 can be stored to disk and recalled or held in RAM 144 where their order dictates the flow of the interview 106. These POs can be stored to disk and later recalled for editing and subsequent output. These POs 210 are defined according to predetermined formats 212 and produced by the parse engine 208. The rules and interpretations of this syntax are stored in rule POs 235 which contain unique byte code. These rule POs are used to translate the knowledge base into persistent core objects 210 written in a machine readable language. All of the POs for a given knowledge base 204 are interrelated, and when stored on disk, make up the binary knowledge base file 112.

FIG. 6 is a flow chart that illustrates the components of the run time or execution module of the CaD program. The execution phase requires that a binary knowledge base file 112 exist, having been previously prepared according to the parse routine 214 as outlined in FIG. 5. The CaD execution program 216 consists of six primary software components. These include the knowledge base manager 218, the view manager 220, the persistent core objects 210, the display manager 222, the object manager 224, and the inference manager 226.

The view manager 220 is responsible for constructing and communicating with the display manager 222. The view manager 220 is also responsible for constructing and communicating with the list display. This is in order to display the list associated with the current question. The view manager 220 is also responsible for executing the current knowledge base at the proper times and determining the current question. The display manager 222 can wrap the text into the display as it is generated and keeps track of the objects associated with each piece of text. The display manager 220 also controls the display buttons representing questions and handles mouse input when the user clicks on a list selection or the "OK" button 432. The display manger 222 controls the translation of the data into a textual format which can be saved to disk as a text file 120, FIG. 1 or printed out as a hard copy 110. The data file may also be saved in a binary file consisting of serialized persistent objects. We call this an SCT file. It is one type of archival storage 122. An SCT file can be reopened for editing or adding additional material. It may also be shared with another user. The knowledge base manager 218 is responsible for performing open, save, and close functions on the current knowledge base 112. The knowledge base manager 218 is also responsible for performing open, save, and close functions on the newly created document file 228. This file 228 can be modified by the user 102 and stored to disk. This document file 228 can be recalled 114 for later editing.

The Inference table manager 226 manages information on disk regarding inference rules as originally defined in a knowledge base text file but created in inference table format during parse time. Values are assigned to variables due to a user answering a question, or to an inference rule assigning a value to a variable. The inference table manager then determines if there are any rules defined for the variable-value pair currently being assigned, and if any are found, it executes the inferences.

Figure 7:
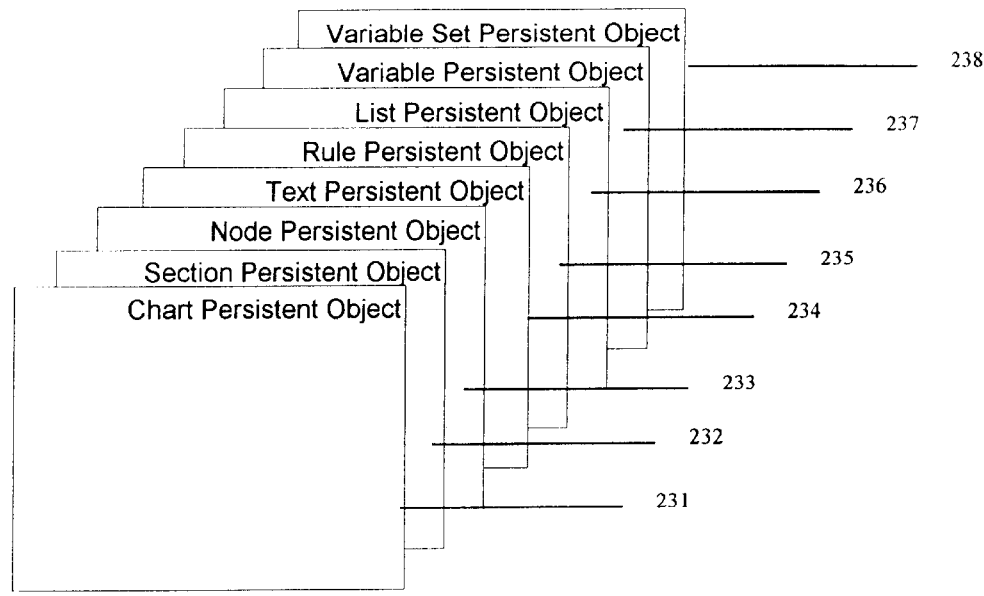
FIG. 7 is a schematic representation of the various types of persistent objects.

The persistent core objects (PO) 210 consist of several objects as outlined below. The object manager 224 is responsible for saving and restoring the POs to and from disk 146. The CaD program utilizes eight major types of POs. These are illustrated in FIG. 7. The document PO 231 maintains a list of sections which are important to define the structure of the document. The document PO may also contain other document specific information e.g. an identifying number to reference that particular record. This number is contained in a special variable object which is used to generate unique filenames. The section PO 232 maintains a list of nodes that will be executed for the section of the document they represent. The section PO also contains policy information regarding the display and execution of the section. The node POs 233 maintain a list of zero or more executable POs. These POs can be of one of five classes. The five classes include text, rule, variable, node, and template POs. These five classes as well as the "DO" command are discussed in more detail under the discussion of the node division. The text PO 234 contains text, which will be displayed when a node executes them. The rule PO 235 contains the binary code representations of the flow control logic and actions associated with the condition(s) in the knowledge base rules. The list POs 236 are referenced by variable objects 237 and maintain lists of possible answers to questions represented by variable objects. The Variable POs 237 maintain zero or more selections and maintain a reference to 0 or 1 List objects. Variable POs also maintain a reference to 0 or 1 variable set objects, and a set of CaD specific attributes. These attributes specify the behavior of the CaD executing software regarding whether the question represented by the variable has been answered or not. If an answer was manually selected by a user, then that user's "user level" is recorded as well. In addition, variable objects may store the results of inferences only. Such variables exist only to be referenced by a rule object and never represent a question that the user can answer. The variable set POs 238 provide the ability to group variables in a single object. The POs also provide the ability to provide multiple instances of such groups so that the same Node and Rule objects can use indirect references to more than one actual instance of such variable groupings. The basic CaD execution program 216 combines all of the above components. The knowledge base manager 218, the view manager 220, the display manager 222, the object manager 224, and the inference manager 226 are combined with the persistent objects 210 themselves 231–238 to form the execution program. A CaD editor program combines the execution program outlined above along with the parse function diagrammed in FIG. 5.

Knowledge Base Language Definitions

Figures 8, 9:
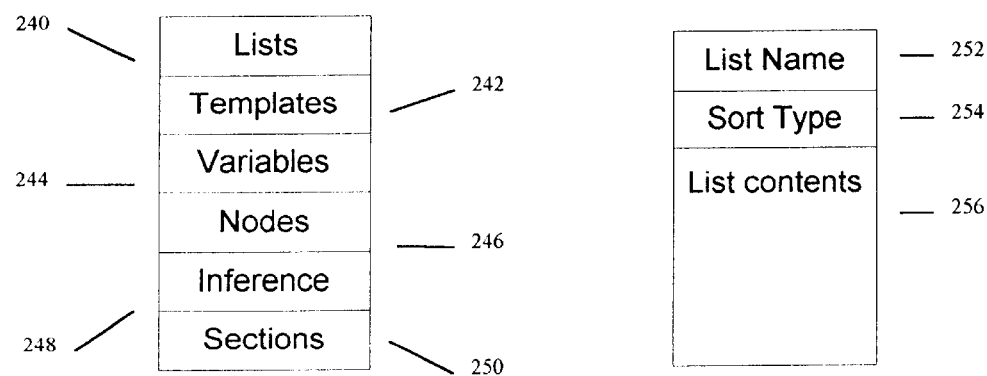
FIG. 8 illustrates the six divisions of the knowledge base text file.
FIG. 9 is a schematic representation of the LIST object structure.

The essence of the CaD program is a script language with newly developed rules and syntax. This language is created for the particular types of activities described herein. Namely, the production of technical documents based upon the results of an interview and guided by the knowledge of a domain expert. The knowledge base text file 204 is written as ASCII text. There are, however, specific keywords with unique meanings as well as specific rules with a defined syntax. The knowledge base text file 204 is translated into a binary form 112. This process is outlined in FIG. 5. The knowledge base text file 204 consists of six divisions as illustrated in FIG. 8. These divisions include lists 240, templates 242, variables 244, nodes 246, inference 248, and sections 250. Each of these represents a type of PO 210 which can be written to disk and recalled to computer memory where it can perform its role in generating a document. The document is produced as the appropriate POs are linked together in a serial manner in the correct order for display and output. FIGS. 17a–17f represent sample consisting of actual knowledge base text file code 204 which may serve as a useful reference throughout the following sections. In contirast FIGS. 7–16 are schematic representations of the various components of the knowledge base language 202. FIGS. 17a–17f serves to illustrate the knowledge base language syntax described below. This file is markedly abbreviated but shows examples of each of the major syntax features 202. Each new division is noted to be introduced by the division name or keyword in square brackets [ ] e.g. [LISTS] 224. Reference numbers between 334 and 400 are found in the sample KB file. Other reference numbers are found in the appropriately referenced figure. FIG. 8 illustrates the 6 divisions of the knowledge base file 204 as noted.

The LISTS division 240 defines names of lists and choices 256 within each list. Lists 256 are referenced by variables. I.e. a list contains the possible choices from which a selection may be made. This selection, once made becomes the variable value. The TEMPLATES division 242, FIG. 17b, defines the types or templates from which groups of variables or compound variables can be derived. The VARS division 244, FIG. 17c, defines the variables. Variables can be simple variables or compound variables based upon a template. The NODES division 246, FIG. 17d, defines the various nodes that make up the document decision tree.

The INFERENCES division 248, FIG. 17e, defines tables of inferences that are used to set the inferred selections (and optionally lists) for variables and/or bitmaps based on the value of another variable.

The SECTIONS division 250 gives a section name and a list of nodes for each section in the document. In the example of the medical record these sections might include such topics as history, physical exam, and treatment. Divisions of the Knowledge Base Text File FIGS. 9–16

The list division begins with [LISTS] 240. FIG. 9 illustrates the structure of the list object. Lists are referenced by variables 276. The list is displayed as a pick list when a variable 244 is queried. A list is always associated with or called by a variable 276. The same list 256 may be referenced by several different variables. Each list begins "NAME=name" 252. A list can contain special keywords that are interpreted internally by the program. Special keywords 334 are enclosed in square brackets [ ]. Such keywords are not written to screen or text. An example of such a keyword is [NEW]. This causes an input modal dialog to pop up so that the user can input a choice not on the list. The next line many contain a "SORT=TRUE/FALSE" flag 254. If no SORT=flag is specified, the list will default to non-sorting. Every non-empty line after that will be considered an entry in that list 2564, until another line with NAME=is encountered. Another tool that adds flexibility to the way the text is handled is a means of distinguishing between menu text and display text. The menu text shows up on the pick list on the screen and the display text is what appears in the printed document. When a node contains a VAR statement, the result of such a statement is to display the text associated with the value of that variable. The text selected from the menu is known as the menu text and the text which is output by the VAR command is the display text. If separate display text is used there is always a one to one correlation between menu text and display text. In each entry line, the backslash character (\), if present, separates the list entry's menu text from its display text 338. The display text might be an expanded form of the menu text but in some cases it might be an abbreviated form. This could be used in cases where technical abbreviations are used in the final document 110. If there is no backslash entry, then the entry's menu text will be used as its displayed text. An alternative way to convey more information is by using the %VAR% construction 374. Whenever text is output to the document 110, the use of the %VAR% construction will cause the display text to be inserted in that position.

Figure 10:
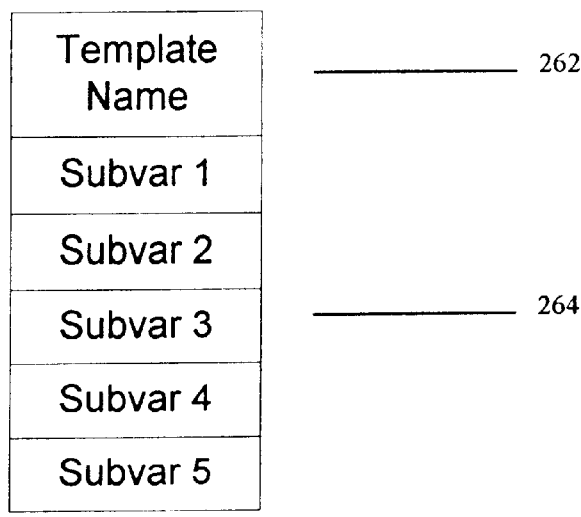
FIG. 10 is a schematic representation of the TEMPLATE object structure.

The template division begins with [TEMPLATES]. FIG. 10 illustrates the structure of the template object. The use of templates allows dynamic redirection during program execution. Templates also allow for greater efficiency by reusing of components. An example of the particular utility of templates would be in the case of a medical record where an examiner might want to examine duplicate (i.e. left and right) organs. A template 242 is a list or a set of variables. Simple variables (variables that are defined in the VARS section without referencing a template) contain only one value. Variable sets use a template, and contain multiple component variables. Because some rules can reference a template name rather than a variable name, the knowledge base programmer 200 must choose template names 262 which are unique, not only for templates, for but variables as well. For more info on this, see the VARS section and RULES section.

Figure 11:
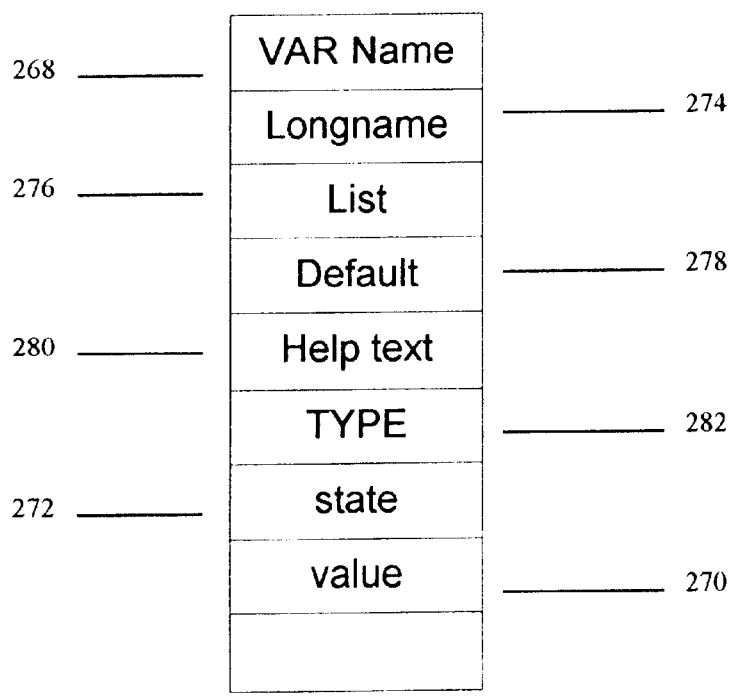
FIG. 11 is a schematic representation of the VAR object structure.

Each template begins with "NAME=name". Following the name line 262, there must be one or more of the following component variable descriptions 264. These are identical in syntax to the simple variable descriptions in the VARS section, except that rather than NAME=, they begin with SUBVAR=. Each component variable section -264 is indicated in the knowledge base with a "SUBVAR=name" line 340. FIG. 17b. The name supplied here is used in conjunction with the main variable name, with a "." in between them. Thus each SUBVAR 264 has a compound name that can be used to reference a new unique value. For example, if the template is named COM (complaint) and there is a component variable defined with the name SUBVAR=LOC (location), a variable called COM1 may be derived from a template called COM. Then a rule a rule may be constructed to test the value of COM1.LOC 342 i.e. the location of complaint # 1. Following the SUBVAR=line the same kinds of lines may be used as were utilized in the VAR sections. The SUBVAR sections can be repeated indefinitely for each template. Note that, in order to make the file easier to read, the SUBVAR lines are indented The variable division begins with [VARS]. FIG. 11 illustrates the structure of the variable object. Each variable has a unique name 268. Variables store information selected by the user during document generation. The information stored is known as the value 270 of the variable. The value could also be thought of as the contents of the variable. The value 270 is a dynamic attribute and usually comprises a text string. The other important dynamic variable attribute is its state 272.

Variables can have one or more static attributes as shown. These attributes include longname 274, list 276, default 278, helptext 280, and type 282. The information stored in a variable is selected in one of two ways. It may be based on user selection of an item from a variable's associated list (manual selection). Alternately the value may be an inferred selection because of an inference that occurred when the user selected some previous variable. Each simple variable definition begins with "NAME=name 268. There is an optional template parameter, " TEMPLATE=template$_{13}$ name". Usually it is omitted in which case the variable would be a simple variable.

A compound variable could also be defined by using a template 242. This type of variable definition requires the use of template definition syntax, "NAME=name <TEMPLATE=template_name>" 344. If the "TEMPLATE=" parameter is used then the variable in question is defined as a compound variable. The newly created group of variables are defined according to the attributes of the various subvariables 264 of the template 262. The use of the SUBVAR syntax is reviewed in the template section above.

As a simple example of variable redirection and substitution suppose a template named COM (complaint) had two subvariables known as IS (what is the complaint) and LOC (location). Then the template could be reused and redefined for multiple complaints. The syntax NAME=COM1 TEMPLATE=COM, would cause the subvariables from the COM template to be reused and renamed as subvariables of COM1. This process can be repeated for COM2. If complaint #1 was a laceration to the hand and complaint # 2 was a bruise on the head then the final syntax and variable values could look like this:

COM1.IS=laceration
COM2.IS=bruise
COM2.LOC=hand
COM2.LOC=head

Later rules can be written to assign COM to one of three instances, and then evaluate COM.IS in a generic sense. In this case the rule would consider either the value of COM1.IS and COM2.IS. Assuming COM2 was the most recent reassignment then this would be the variable evaluated by the rule. Alternately a rule could be written in a specific way to evaluate only COM1.IS and ignore COM2, COM3 etc. Thus the CaD software has the ability to generate compound variable names and create new variables which are logically related or interdependent. Thus nodes and rules can be reused for different instances of related sets of variables. This is one of the properties which creates the unique power and, flexibility of CaD.

Static Variable Attributes

The following types of static variable attributes can appear on the lines immediately following the NAME line for each variable. Static attributes are defined by the knowledge base author or domain expert 200. They are written into the knowledge base 204. The dynamic attributes are volatile and their values change at run time depending upon user actions. The most basic attribute of a variable of course is its value 270. The second dynamic attribute in the CaD program is the variable's state 272. These two attributes are discussed later in this section. The following represent the user defined or static attributes. These can appear in any order in the knowledge base. The first line of each paragraph represents the correct syntax for that attribute.

LONGNAME text—string

The LONGNAME attribute line 274 simply supplies a more descriptive term to describe the variable. This is the phrase which is displayed on the prompt line 410 on the screen to prompt the user to answer the question. The longname attribute may also employ the %VAR% syntax whereby a variable is embedded in a line of text. This is used to communicate context specific information to the user.

LIST list_name

The LIST attribute line 276 references the name of a list object 252, a list of possible choices for the value of the variable. Note that while every variable must have an associated list of some sort even if it is embedded in the variable, there is not a strict one to one correlation between a list and a variable. A single list may be referenced by multiple variables. The list associated with a variable may be changed dynamically by the use of inference tables and inference rules. Thus a single variable may use different lists and not simply different choices on the list. This process is dynamic and context specific. An embedded list can be created in the variable division of the knowledge base. All non-empty lines following NAME and not using a recognized keyword will be considered entries in an embedded list for that variable. An embedded list will be created for a variable only if there is not a LIST line for that variable. Embedded lists are given the same name as the variable.

DEFAULT choice_menu_text.

The DEFAULT attribute 278 indicates an initial default value for the variable in question. This will also cause the variable to behave just as if that value had been inferred to the variable. This default value may be overridden with manual input from the user.

HELP help_text string (Not Enclosed in Quotes)

The HELP attribute 280 is used to list a help text string which supplies additional information if necessary. The text is not enclosed in quotes.

TYPE Command Keyword(s)

The most complex of the variable attributes is the variable TYPE 282. Then syntax is TYPE "keyword". The TYPE attribute is set by a TYPE keyword. Multiple keywords may be used. If multiple keywords are used they are separated by blanks 282. By defining a variable's type the specific functional characteristics of the variable are defined. These characteristics define how the variable can be used at execution time. This data structure enables the CaD software to function in unique ways. Possible keywords that may be used to define a variable type are defined in the next section.

TYPE Keywords

NODEFAULT

The variable cannot be considered inferred. It requires manual input by the user.

MULTSELECTABLE 354

The variable can receive multiple values. Without this keyword, only one value may be contained in the variable.

OMITTABLE 356

The variable can be omitted manually by the user 102 or by way of inference even though it is called by the program. No text value will be output and no questions will be asked. This refers to a specific act of omission by the user 102 or the program 100. Other variables are simply not called by the program during a particular execution. This has no bearing on the concept of omission. If a variable is omitted, this is tracked in the variable's state 272.

INFER_ONLY 358 The user will not be asked to select a choice for the value of the variable. The value can only be input by a rule or inference.

RATCHET 360

The value of the variable must be numeric. Its value may be increased by subsequent inference rules but the value can never decrease. If an inference rule attempts to set the variable at a lower value it will simply be ignored. This data structure is utilized to indicate that a more complex level of documentation is required for some reason. It is important that this not be overlooked. Rules can then be written based on the value of the ratchet type variable. NUMERIC_ENTRY 362

If the edit dialog is opened on this variable by selecting the [NEW] keyword then a special modal dialog window is opened which facilitates entry of numeric data with a pen. This input dialog is illustrated in FIG. 11.

DRAWING <[initial.bmp]>

If a variable is of the DRAWING TYPE this allows a pop-up window 588 to be opened when the variable is selected or active. The pop-up window may be blank or contain a drawing template. The [initial.bmp] filename is optional. If a file name is specified in this way then a drawing will appear when the window is opened. The user can then edit or and to this drawing.

IMPORT

The import keyword means that the value of the variable can be read into CaD from a database file. The name of the database file to search is noted in the CaD.INI file. This input database must contain only one record, i.e., only one value per field. The CaD program will search for a field with the same name as the current variable. If a mach is found the value will be input into the CaD variable.

EXPORT

The export keyword means that the value of the variable can be exported from CaD to a database file. The name of this output database file is noted in the CaD.INI file as well. This output database will then contain summary information from all the documents produced by the CaD device. This database can them be sorted, filtered or queried by a user or reviewer. A wide variety of reports can be generated to analyze procedures and outcomes or to conduct scientific research. An additional unique feature of the database export feature is that the state 272 of a variable 244 can be tracked and exported as well as its value 270. Thus it can be measured whether a certain choice was made by a particular user or if a user omitted a certain choice

FILENAME

The use of reserved variable names is allowed for special purposes. In the preferred embodiment the variable name "MRN" 364 is the variable designated with the specific type flag set with the filename command. This variable MRN is the name of the variable designated to contain the "medical record number". This unique eight digit number is assigned to identify an individual patient in the hospital setting. The CaD program automatically uses this number to create a unique filename when the document is saved to disk.

The default settings for the variable TYPE, if not otherwise specified, are DEFAULTABLE, (not) MULTSELECTABLE, (not) OMITTABLE, (not) INFER_ONLY. This means that the default type of variable is one which may have a default and only one selection may be made from a list. The variable may not be omitted from the document if the variable is reference by the internal flow of the program. Finally, the default state for a variable is that it may be manually selected by the user.

Dynamic Variable Attributes—Value 270

Fundamental to the concept of a variable in mathematics or computer languages is the concept of a name 268 for the variable which is constant and defines the variable and a value 270 which can change. The use of these terms in CaD is consistent with this understanding. In the CaD program the value of a variable is generally defined when a user makes a selection from a list. In CaD a variable may have a value or contents that contain more than one selection if it is defined a multi-selectable 354 by the type attribute 282. A variable can also be of the infer-only type 3586 and thus it is not available for user input. In the preferred embodiment the value 270 of a variable can also be inferred in one of four ways. It can be set to equal the value of another variable by the command \SETVARFROMVAR. It can be set internally by the program by use of the \SETVARIABLE command 392. The value of a variable may be the sum of the values of two other variables by use of the \SETVARFROMSUM 393 command. In the CaD program this syntax is used not for numerical data but for combining multiple selections (string variables) from different lists 518. The value of the new variable is not a numerical sum but rather a concatenation of the values of the two previous variables. The fourth way in which the value 270 of a variable can be inferred is by the use of an inference 248 table. The syntax for the inference table is described in a subsequent section. In CaD an inference table is usually used when the value of a certain variable has implication for the values of more than one other variable. This is the structure that allows a given user to specify defaulted personal preference values for commonly used variables. These values can be selected in advance at the time the knowledge base is prepared, i.e., a variable default 278. These values can also be inferred and a wide variety of complex ways using combinations of conditional rules, inference commands and inference tables. These newly inferred variable values can then be inserted into the document automatically.

Dynamic Variable Attributes—State 272

One of the unique features of the CaD language is the use of the variable state 272. In its simplest sense the state of a variable could be considered selected as opposed to not selected. I.e., has the user selected a value for the variable from an associated list. In CaD this concept is expanded considerably. The state attribute 272 tracks whether each variable:

1) has been selected at all, either manually or by inference or by default,
2) has been manually selected by a user 108,
3) has been inferred by the CaD program,
4) contains a default value, or
5) contains multiple selected values.

In addition to tracking whether on not the variable has been manually selected, the CaD program records the user level of the person who selected the value. Thus, if the CaD programs were being used by an expert and an assistant to prepare the same document, it could be set up so that the assistant was not able to override the data input by the expert user. This has very important ramifications in the case of an expert system. One of the significant limitations of expert systems is the garbage in, garbage out phenomenon. In many cases the output of the expert system is compromised because the actual data input requires expert interpretation in order to be of any real value. The CaD system can be setup to prohibit a less experienced user from overriding data supplied by a more expert user. CaD would also prohibit a less experienced user from omitting a selection made by a more expert user.

In situations where text is output to either the screen or to the document a standard %VAR% syntax 374 can be used. This will cause the value of the variable to be written to the document at that position. This syntax can also be used in the "LONGNAME" text 274 to provide more accurate feedback to the user on the prompt line. This enables the CaD interview 106 to be a very dynamic process.

Node Division

Figures 12, 13:
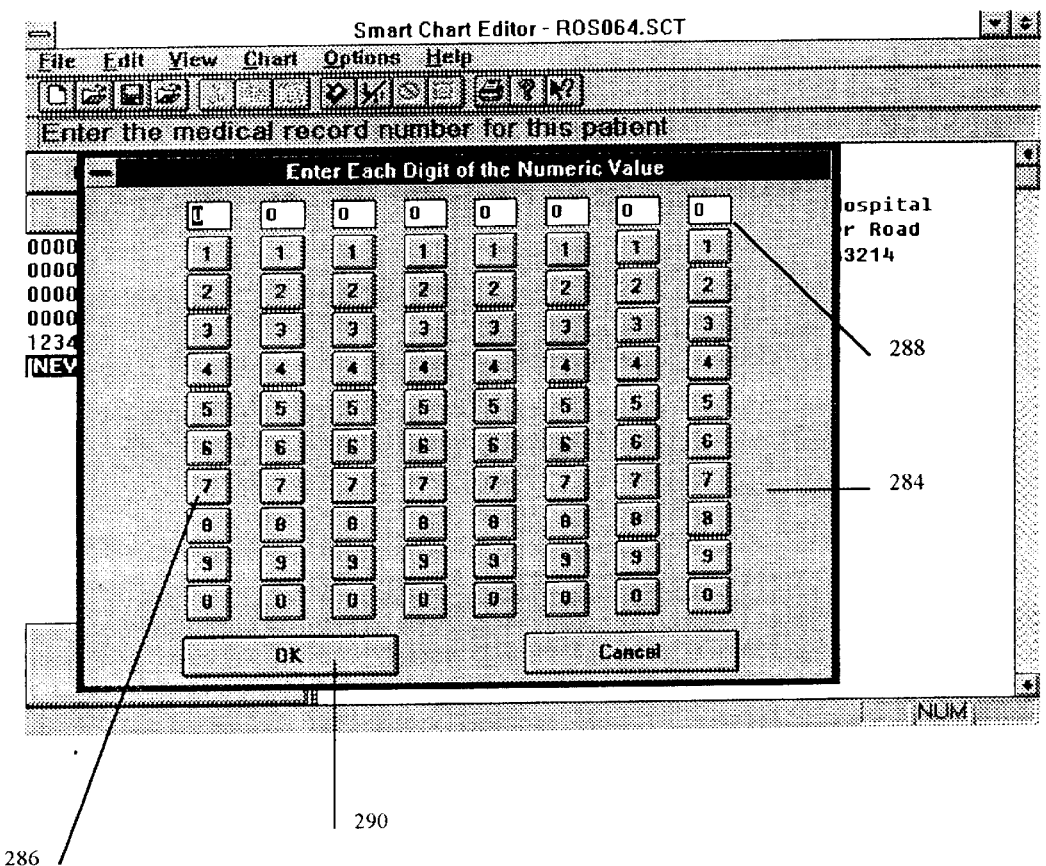
FIG. 12 is a screen snapshot demonstrating the numeric data entry grid.
FIG. 13 is a schematic representation of the NODE object structure.

The node division 246 of the knowledge base FILE begins with [NODES]. FIG. 13 illustrates the structure of the node object or node syntax in the knowledee base file 204. A node is the basic structural element of the document. A document is generated as a user is guided through a series of nodes. A node is like a small program. A node definition begins with a line, "NAME=node_name" 292. The node is executed, line by line 294, and ends up with a Boolean status of executed or not executed. Nodes are executed either a) because they are included in a section's node list 366, or
b) because a rule in another node invoked them 378, or
c) because they were directly invoked by another node 300.

The top level nodes are anchored to sections (see the SECTIONS division below). Other nodes may be referenced only as the result of particular selections made by the user at run time. The use of nodes allows for dynamic control of the flow of information and the structure of the document.

The node 246 and section 250 divisions work together to define a huge tree structure of potential pathways through the document. Typically a given document would utilize only a small fraction of the nodes defined in the knowledge base. Part of the ability of the user to customize the knowledge base for his/her individual needs comes from the ability to create new nodes and name them in any fashion the user chooses. Naming schemes or syntaxes can be created for different fields. According to the preferred embodiment a naming syntax is devised for use in the knowledge base. This naming syntax has particular application in the field of emergency medicine but serves to illustrate how such a syntax can create a near infinite variety of possible branching points in the node structure. A small fragment of the index for the naming scheme is recorded in FIG. 15. This is included only as an example of one possible method for systematically naming nodes and other components of the CaD knowledge base. The general pattern is to reduce all significant words to a three letter abbreviation 310. These abbreviations are then linked in the form A_B_C 312 where A,_B, and C represent appropriately abbreviated names. If a commonly used abbreviation exists 314 this is used instead and the three letter convention is not strictly enforced. It is common to nest these node names three deep.

Sometimes four layers are used but this is unusual. This sort of naming convention avoids duplicate names and yet the meaning of the abbreviation is usually intuitively apparent. As an example, the location of pain in the chest might be listed as CHE_PAI_LOC. This name could then be used to name a node, a variable, or a list. The same name could be used for all three types of objects. Similar naming conventions could be created for other professions. Using this system, with 35 alpha-numeric possibilities for each character space in each of nine potential character spaces, allows for the generation of more than five trillion unique names. This naming syntax is one more tool used to create variety and flexibility in the CaD program.

Although the number of possible nodes is potentially astronomical, this fact alone does not begin to adequately explain the degree of variation and individuality attainable with CaD software. Any individual node generally references one or more variables. Each of these variables can contain different values 270. The list 276 for each given variable can be changed as well resulting in further variation and individuality in the resultant document.

Optionally, the next line following the name can contain help text. This is identical to the construction used in the VAR division discussed above. The syntax is HELP help_text (text not enclosed in quotes). Remarks can be made within the individual node section as well. Typical syntax remark (REM_) is used. Each non-empty line 294 until the next NAME=contains an appropriate key word or instruction. Each keyword represents one of five classes of POs 210. What actually happens at execution time is that the PO 210 represented by the keyword is recalled from disk and executed as a subroutine to generate the text at the next position in the document. Lines of code containing these keywords can appear in any order and each type of keyword can be repeated indefinitely. These are the possible object classes represented by each keyword and what each means during execution time. The correct syntax is noted on the first line of each paragraph.

TEXT "sample line of text" 370

The text from the object is inserted at the next point in the document. An alternative syntax allows the use of %VAR% 374_whereby the value of the variable VAR is inserted at the current position in the text. Lines of text may be interspersed with VAR commands and rule commands. A special text command is represented by the syntax "n" 374. This causes a line feed or carriage return to be inserted into the document.

VAR var_name 376

The variable by the name of var_name is queried for its value 270. Normally this will result in a list 256 being presented to the user 102. The user then makes a selection and the result is output into the document. If the variable is multi-selected, i.e., it contains more than one value, then the appropriate grammar and punctuation are automatically incorporated when the values are printed in the document. The multi-selected values will be automatically printed as A, B, and C when they are displayed in the document. There are several variations of the VAR command. They are listed as options or switches of the VAR command in a separate section below.

NODE node_name 378

Figures 14, 16:
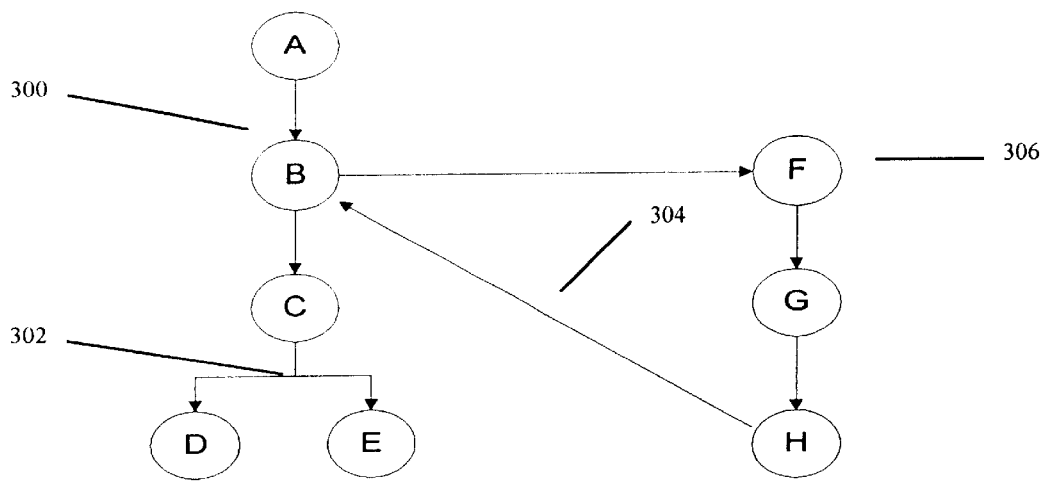
FIG. 14 is a flow chart which illustrates various node relationships, including looping, branching, and return of control.
FIG. 16 is a schematic representation of the inference object structure.

Nodes allow the use of sequential, branching, and looping program structures illustrated in FIG. 14. Nodes generally execute in a linear or sequential manner 300. The section division in a knowledge base contains a list of nodes which are executed in this way. When the NODE command 378 is used, the control of program execution is transferred in the same unconditional way to the node identified. This is the simplest and most direct method of program execution.

Control of routing or branching can also be accomplished via the use of rules. With a rule, the control of the program is transferred conditionally 302 depending upon the results of the rule execution. Program execution continues based on the status of that node. If there are more lines to be executed in the first node, then control will return to the first node 304 to execute the subsequent lines after the second node has been executed. Nested subroutines 306 are created in this way. Looping routines can be created as well. The syntax for this function is different if it is used as a result of a rule. When a rule initiates transfer of program control to another node the "NODE" command keyword is omitted. The name of the node is used alone.

IF (A=B) \ACTION 380

If/then rules can be created, to test various conditions and take actions based upon the results. The syntax is IF (A=B) \ ACTION, where (A=B) is some expression representing a test condition that can be evaluated and return a value of true or false. The rule in its simplest configuration involves a test condition and an action. Program execution is directed, based on the status of the rule. A rule begins with a keyword. Standardized logical constructions are utilized. These include the terms IF 380, ELSE IF, and ELSE 382. The rules use standard if/then logic. Typical Boolean constructs utilizing AND/OR and complex constructions using parentheses may be utilized. If/then logical constructs are obviously not new concepts. However, the actions performed as a result of these test conditions are new and unique. Node actions are noted in a separate section below.

SETTEMPLATE template_name=var_name 384

This action assigns a new unique name to particular variable instances. Compound variables are built from a template. This causes any rules that reference a generic template_name rather than a variable name to use the particular variable named by var_name. The general template name (template_name) is replaced by the more specific variable name (var_name). A complex variable or a template, then it must have the form var_name.component_name, as in COM.LOC (complaint location). E.g., after executing a SETTEMPLATE command, COM=COM1, a more specific variable is created. A subvariable might have the name LOC, thus the newly created compound variable would have the name COM1.LOC. Then any rules in the nodes that are executed that reference the general variable COM.LOC will now actually reference the particular variable COM1.LOC.

A node line may also contain a DO action using the syntax DO \ ACTION. This will cause a rule action to be executed unconditionally. This concept is explained further under the a subsequent section entitled rule actions.

VAR Command Options used for Document Control

The normal use of the VAR 244 command is to output a selected list item to the final document. The value of a variable may be a single word, a text fragment or a short list of items. Some of the multiple variations of the use of the variable have been described above. Further permutations of the VAR command are listed in the following sections. Any of these commands can be used in a node 246 wherever a typical VAR construction could be used. The following commands control the appearance of text in the document and the way the computer interacts with the user.

\NODISP var_name 386

This is the same as the VAR command in that the user will still be queried for input but no text is written to the document or to the screen.

\NOQUERY var_name

This is the opposite of VARNODISP. The user is not queried for input even if the variable is in an unselected state. The value of the variable is output to the document.

\DRAWING var_name

This causes a pop-up window to open with a drawing area for graphical user input. If a bitmap has been defaulted then this bitmap will serve as a backdrop or template for the user's drawing input. This is the function as clicking on the drawing button. This command is imbedded within the knowledge base and causes the drawing window to open automatically upon execution.

VAR Command Options Used for Grammar Control

The following commands are used to manipulate the text to maintain correct grammar.

\ARTICLE var_name 387

This is the same as the VAR command, except that the value of the variable is prefaced with an article, a or an, depending on the first letter of the value.

\CONVERSE var_name 520

The CONVERSE command displays all the entries in the variable's list that are NOT selected. If there are multiple selections, the last will be preceded by "OR" rather than "AND". This is generally used with a relatively short pick list and a multi-selected variable.

The VAR options may be combined on the same line separated by a space. \ Therefore VAR\ARTICLE\NOQUERY\CONVERSE would not query the user but would instead place the converse (unselected value) of a variable into the text preceded by the appropriate article (a or an).

Rule Actions

Rule actions are conditional actions executed by a specific keyword in capital letters. As noted above, any node line may contain a test condition preceded by an IF of ELSE keyword. If the test condition is true then the subsequent rule action listed on the same line is executed. If the rule test condition is false, then the action will be omitted and control of execution will be transferred to the next line of the program. Rule action keywords are preceded by a backslash "\". The following keywords are recognized:

\ABORT 388

The ABORT keyword means to terminate execution of the current node immediately and exit the node, and return to the node or section that called it.

TEXT "text to display" 390

This has the same function as TEXT in a node, but cannot contain embedded VAR references (%VAR%). The text will be printed in the document if the rule's condition is true.

\SETVARIABLE var_name list name selection 392

This will reset the specified variable with a new value. It will override a manual selection, unlike inference tables. This is a type of inference. This action can also be used to set a bitmap to be associated with a certain variable.

\VARFROMVAR vartoname\varfromname (target\source)

This will copy the value of one variable into another variable. It will also override manual selection. This too, is a type of inference.

\SETVARFROMSUM var1name\var2name\var3name 393

This will concatenate the values of two variables and enter the values into a third variable. (var1=var2+var3) It will also override manual selections. This is a type of inference as well.

\ENABLESECTION section$_{13}$ name

This will turn on display of section name and execution of its nodes.

\DISABLESECTION section$_{13}$ name

This will turn off display of section name and execution of its nodes.

Any word which appears without the "\" construction will be interpreted as the name of a node to "call". This is identical to the unconditional NODE action except it occurs as a result of a rule execution. The keyword NODE is not necessary in this situation. The control of program execution will be transferred to the new node and return once the new node has been executed 302.

DO \action 394

Where the action specified is any of the same actions that can follow a condition in the IF/ELSE rules. The commands SETVARIABLE, VARFROMVAR, and SETVARFROMSUM are all forms of variable inference actions which are generally executed from rules as a result of some test. The DO command is different than the rule command in the sense that rule commands are conditionally executed. The DO action allows the knowledge base author to cause one of these actions to always be executed unconditionally from a given node. There is no rule to be evaluated in a DO command line.

Another unique language construction designed explicitly to increase the power of the CaD program is the inference table or object. The inference division 248 begins with [INFERENCES]. FIG. 16 illustrates the structure of the inference object. Inference means that the value of variable B is inferred by or dependent upon a certain value of variable A. The inference division consists of a series of small tables, each consisting of one or more lines. Each table begins with INFERENCE varname=value 316, where value is a text string that corresponds to one of the selections from the list associated with the variable. Each subsequent non-blank line after the INFERENCE is formatted in the form:

I inferred_variable_name \list-name \selection \<selection \<selection \>>

Each subsequent line contains instructions to reset an inference output variable 318. An inference commnand begins with an "I" to initiate a set-variable rule. An inference table is executed automatically whenever the variable named in the first line receives a value. Inferred_variable_name is the name of a variable that has been defined in the [VARS] division. It could be either a simple variable name, or a compound variable name like "COM.LOC". Selection is a text string that corresponds to one of the selections from the list associated with the variable. List-name is the name of a list defined in the Lists division. There can be from 1 to 3 selections listed, which match menu text entries from the specified list. If the list is omitted (two \\) then the list is unchanged. Note that the last character must be a backslash.

The sections division 250 begins with [SECTIONS]. The name of each section is simply followed by a list of nodes 366. The unconditional, sequential execution of these nodes comprises that section of the document. The specification of sections allows the document structure to be defined in a manner according to professional traditions and expectations. The concept of the section is that sections are the top of the decision tree—they will always be "executed" during document generation. The section divisions are utilized as a means of organizing and navigating through the document. The user may select a section name 420 from the drop down chart menu as noted in FIG. 20. This allows the user to jump quickly to another section of the document. The makeup and content of the various sections and even their presence or absence can be variable and dynamic. Each new document section begins with "NAME=section$_{13}$ name" similar to other divisions of the knowledge base. After a name section, the optional keyword DISP=may appear 398. By default, display is YES. The display of a section name may be disabled by setting DISP=NO. Every non-empty non-keyword line after NAME=is the name of a node. Each section contains one or more nodes. The section$_{13}$ name text will be displayed with the formatting characteristics currently selected for section titles. If there is no text generated for the section, the section will be omitted (considered irrelevant) from the printed document. Note that if the resulting text is empty, the section is irrelevant for this document based on the rules in the nodes in the section. In this case, the section title will be omitted from the printed version of the document.

There is also a special keyword TITLE which can appear in the SECTIONS division. The syntax is TITLE="text" 400, FIG. 17f The text inside the quotes following the TITLE=keyword will be displayed at the top of the document, in the formatting characteristics for Title. The TITLE=line must be the last line in the SECTIONS division.

CaD Table File Structure

When a knowledge base text file is parsed into a binary knowledge base file, another file is created. This is a CaD table file. The CaD table file is the binary representation of the inference relationships described in the knowledge base file. The table file causes a top level table to be created, which is used by the CaD program to look up a variable-value pair. For each entry there is a list of entries describing other variables and the values, list, and/or bitmaps to infer into each of these variables.

Database Interface

According to this invention, pieces of data are recorded in variables. The variables 244 can be thought of as receptacles which contain individual pieces of data as the value 270. These individual pieces of data can be imported from or exported to a data base. Each variable 596 in the CaD program can correspond to a field 597 in a database. Once copied to a database, this information can be sorted, filtered or queried. Various analyses can be performed and suitable reports printed.

Screen Design/User Interface FIGS. 18–24

Figure 18:
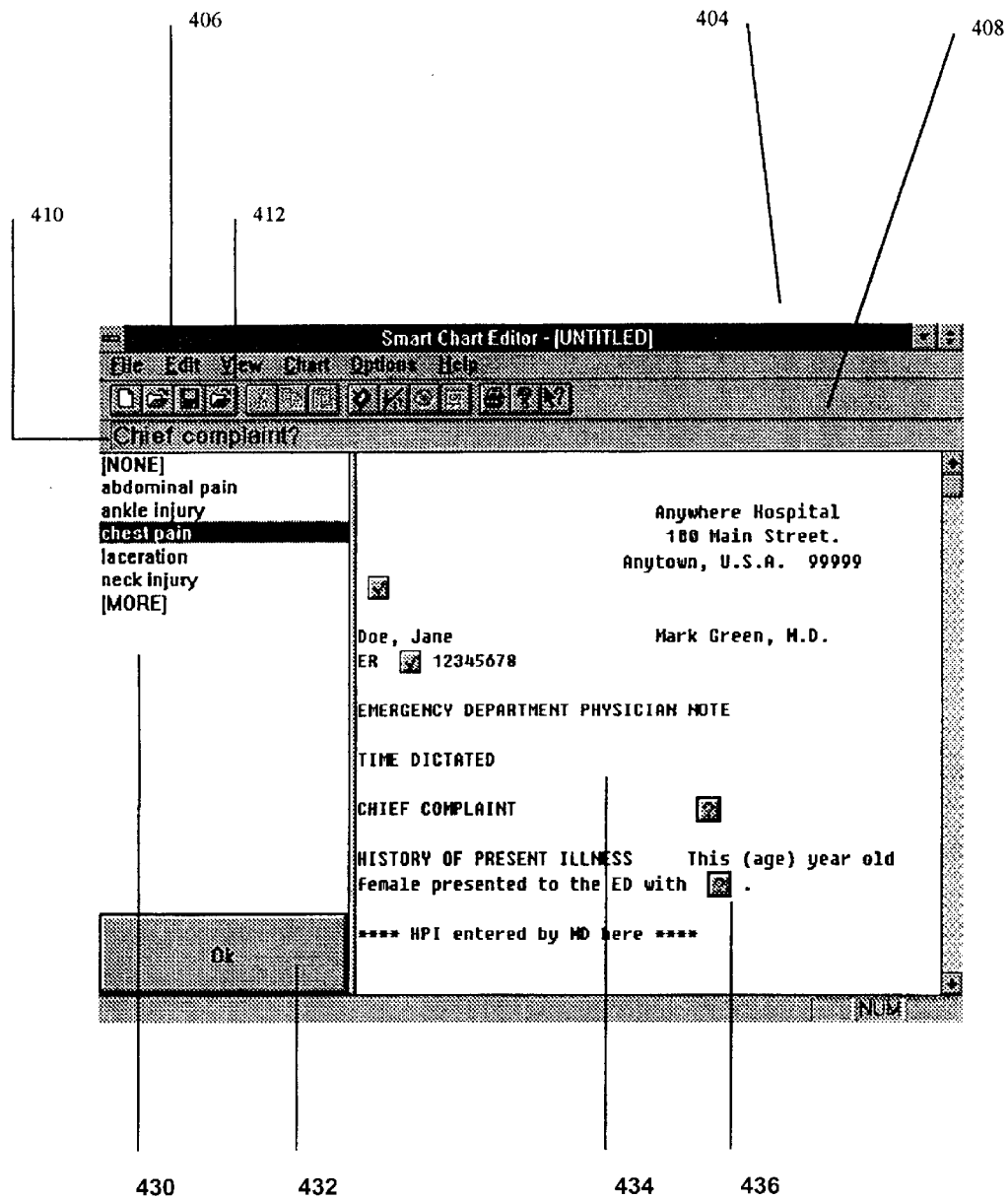
FIG. 18 is a screen snapshot which demonstrates features of the user interface.

The screen design for the current embodiment is illustrated in FIG. 18. The screen design or GUI is designed to be totally independent of the main function of the CaD program. Thus, multiple alternative embodiments could be envisioned or designed. The overall appearance of the user interface is consistent with the commonly accepted Microsoft Windows© standard. There is a title bar 404 that indicates the name of the file which is currently loaded. Some typical WINDOWS© features may be noted in both the menu bar 406 and the tool bar 408. A status bar located below the toolbar prompts the user with the current question 410. The text which appears in this widow is the longname 274 of the currently active variable 244.

Figure 19:
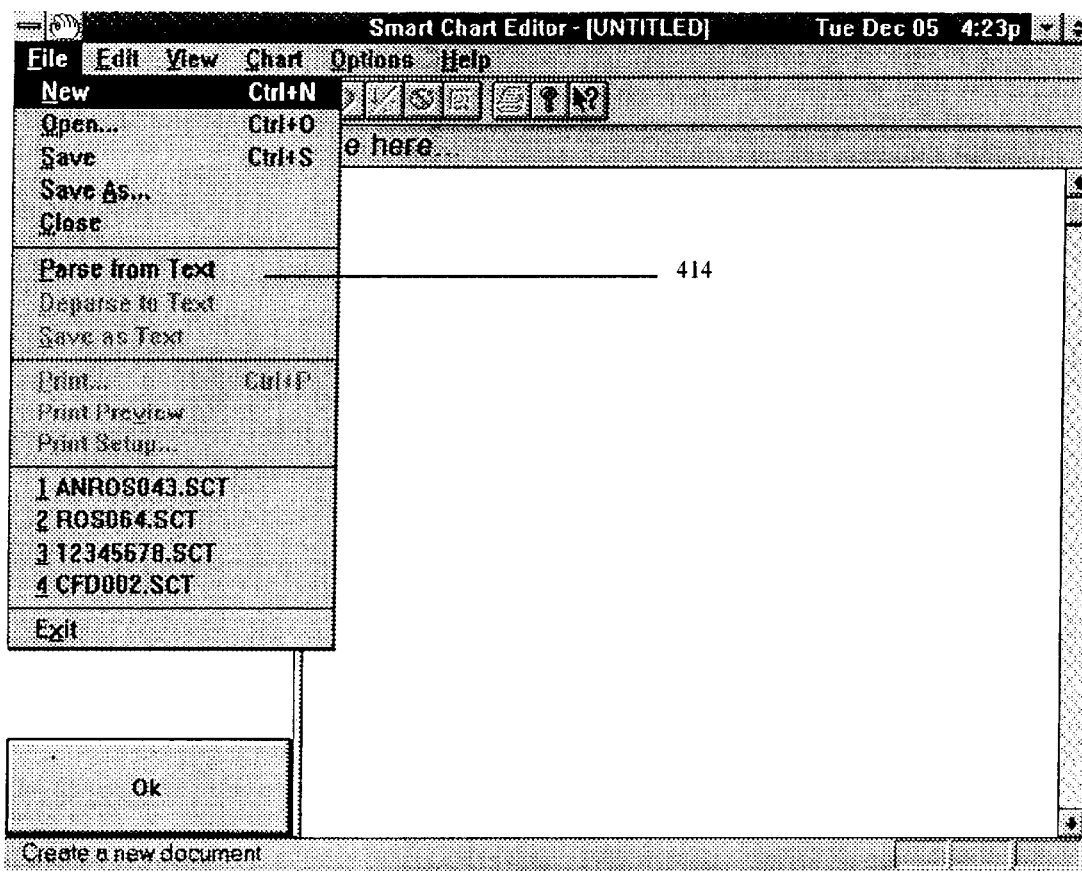
FIG. 19 is a screen snapshot which shows features of the CaD specific File menu.

The menu structure is quite similar to that found in many other windows programs. The Edit, View, and Help menus are similar to those found in other windows programs. The File menu shown in FIG. 19 is similar to other programs. The only menu functions that might be construed as unusual are the parse functions. The parse functions are found only in the editor's version of the program. "Parse from text" 414 will convert a knowledge base text file 204 into a binary knowledge base file 112. "Deparse to text" is simply the reverse procedure.

Figure 20:
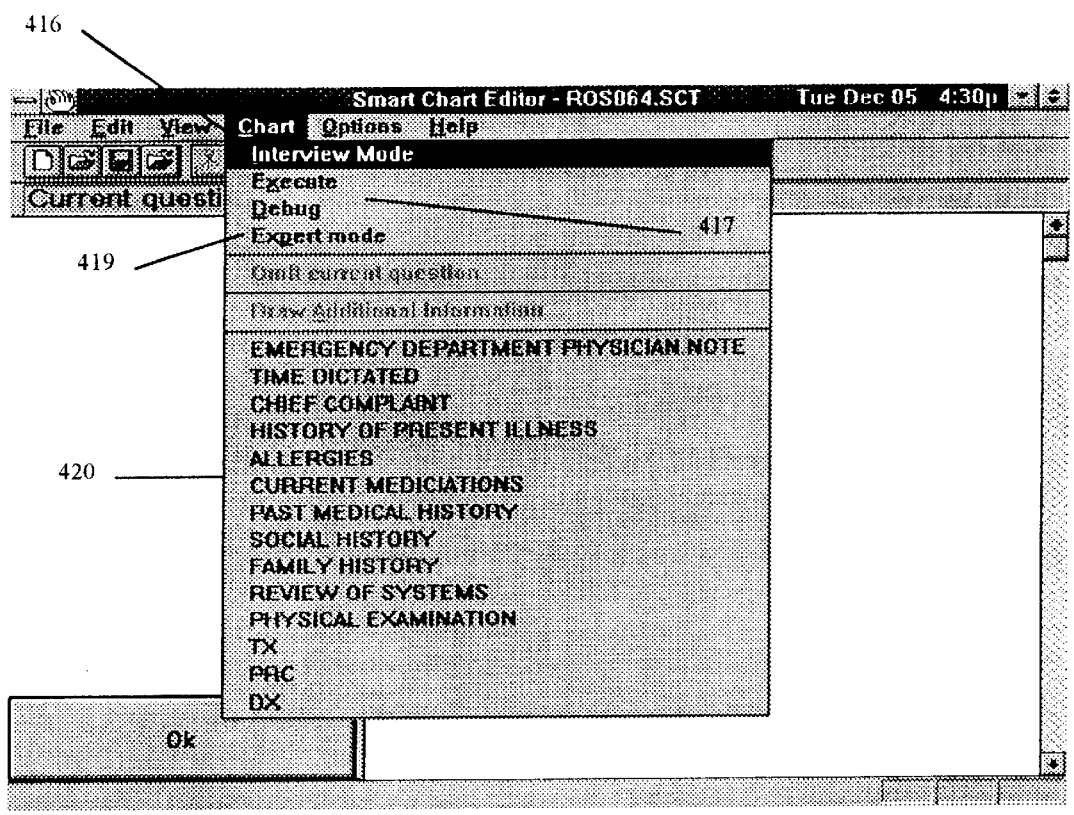
FIG. 20 is a screen snapshot which shows features of the CaD specific Chart menu.

The most notable difference in the menu structure is the addition of a new menu choice, Chart, shown in FIG. 20. The menu choices under Chart control the manner in which the program is executed. The first choice is Interview mode 416. This mode causes the program to wait for user input at each new question. The entire node tree of the CaD program is not re-executed nor is the text window repainted after each menu selection. From the user's perspective, the result is faster progression through the interview process. The Execute choice 417 simply begins execution from the menu. The initial mode of execution is specified in the CaD.INI file. Expert Mode 419 causes the program to jump ahead and fill in any default or inferred values automatically. The user always has the option of editing the document at a later time. In expert mode the program will stop for a user response only when it encounters a variable which is not selected, defaulted, or inferred.

Figure 21:
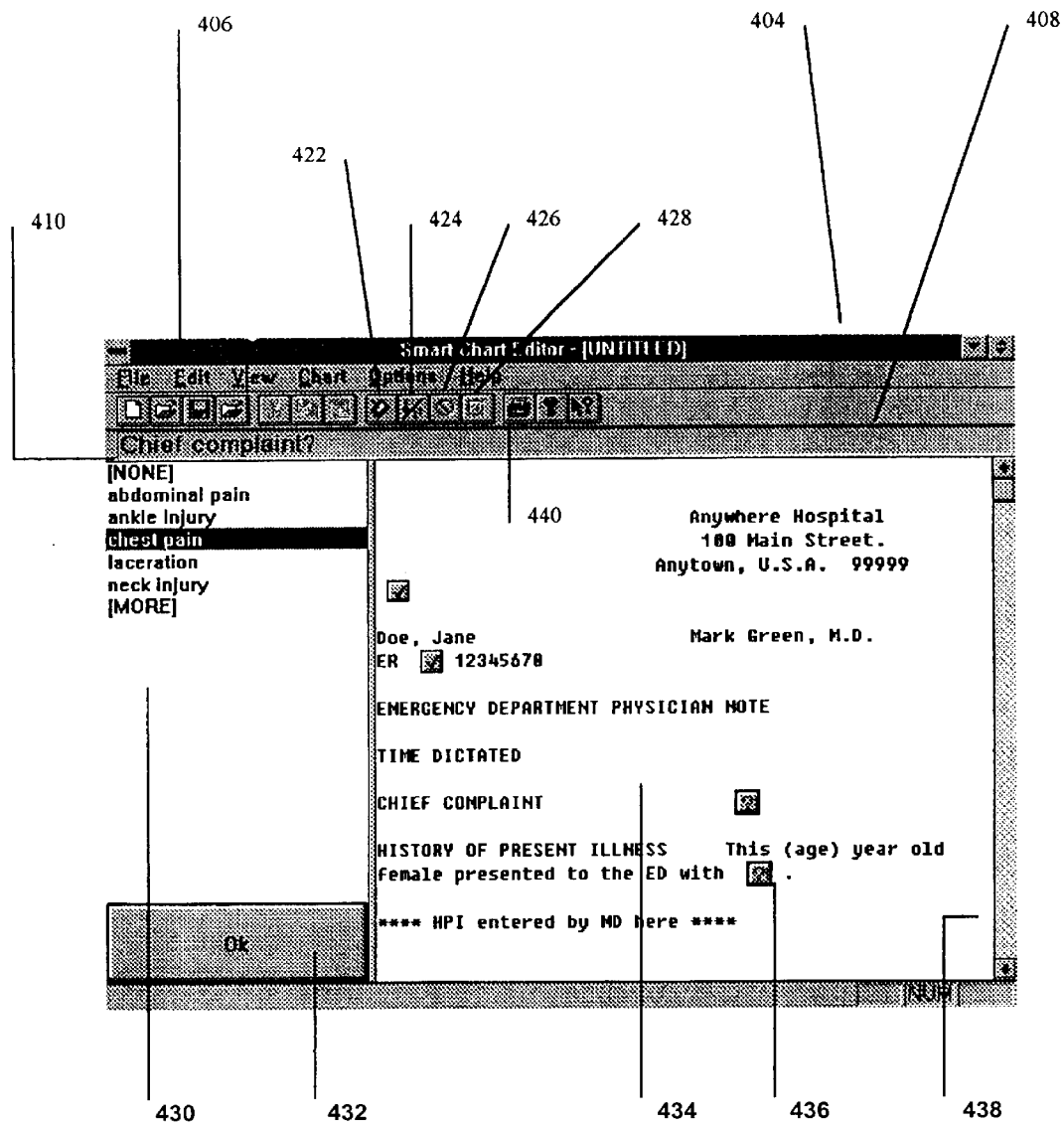
FIG. 21 is a screen snapshot which illustrates a pick list and text window with a menu bar and tool bar.

Tool bar buttons are noted in FIG. 21. There is a button 412 to parse a knowledge base text file 204 to a binary knowledge base file 112. This button is available only on the editor's version of the program 100. There is a button 422 which will initiate the execution of the CaD program after a knowledge base has been opened. This will begin the interview process 106. This button 422 is functionally equivalent to the Execute choice 417 on the Chart menu. Another button 424, toggles the program function between interview mode and text edit mode. In text edit mode the program runs slower but the changes are immediately apparent. Text edit mode also allows the user to select text for editing or revision. There is a button 426 to omit the current question. Another button 428 opens a window which allows drawing or free text entry which is saved in bitmap format. A typically appearing "print" button 440, will cause the currently loaded document to be output in printed format 110.

When the program is executed the current list is shown in a window 430 below the prompt line 410. The appropriate choice can be identified in this window. Scroll buttons are available when needed. Sometimes multiple selections are allowed as outlined in a previous section. A large "OK" button is present 432. This serves as the pen equivalent to the <ENTER> key on a conventional IBM PC compatible computer. This button allows for rapid data entry. If the user wished to accept the highlight (default) selection then only one stroke of the pen is required. The output text 114 appears in the window 434 as it is being produced. Edit buttons 436 appear in the text window. Clicking on these buttons while in text edit mode allows the user to go back and edit portions of the document. Clicking on such a button will call up the list associated with that variable to allow for a new selection. There is a conventional scroll bar 438 which aids in navigating through the document as it appears on screen.

Figure 22:
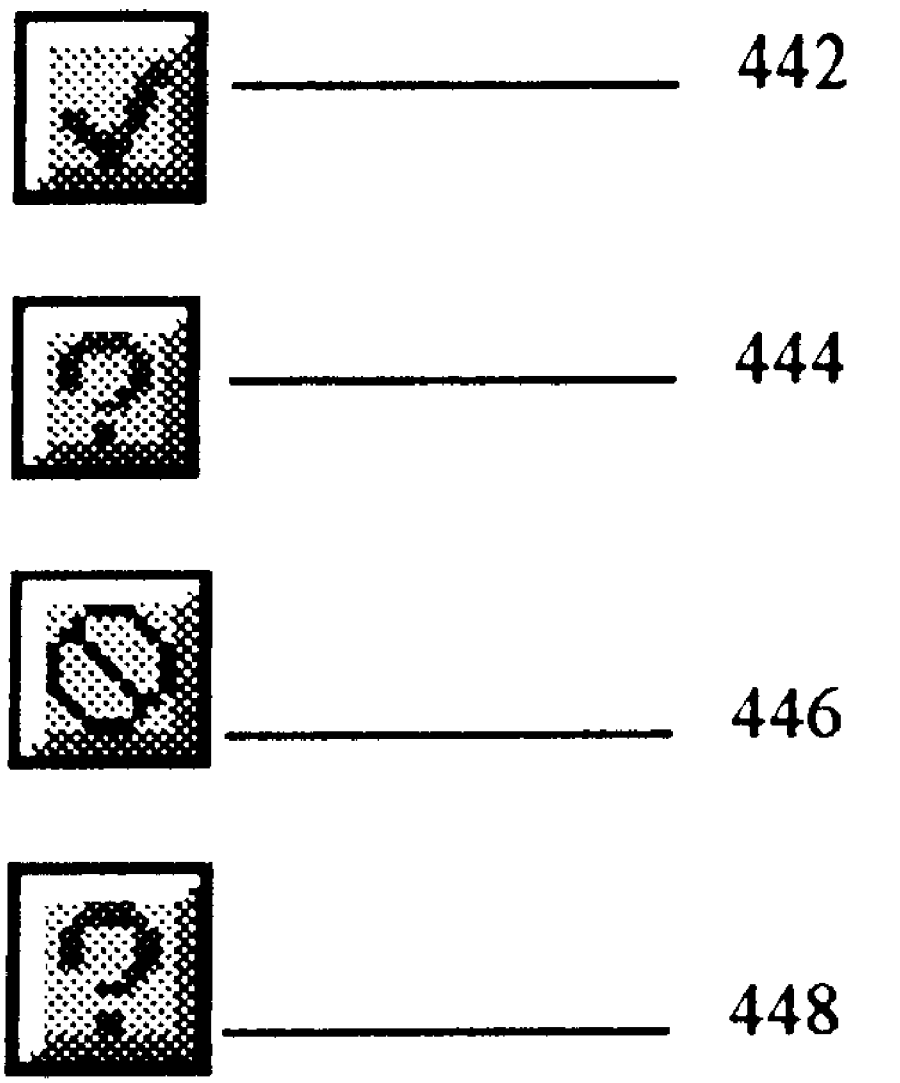
FIG. 22 illustrates the edit buttons for the text edit window and text mode.

FIG. 22 illustrates 4 buttons which can be found in the text editing window 434. A green check mark 442 indicates the question has been answered. Clicking on this button will reopen the question and the pick list. The previously given answer can be changed. A green question mark [?] 444 indicates the question has not yet selected or answered and that the question is optional. It is not required to be answered. The omit icon 446 indicates that the question or variable has been omitted. A red question mark [?] 448 indicates the question has not yet been selected or answered. This question represents a mandatory field and cannot be omitted. The text window is normally activated for editing after the questions have been answered in interview mode. The user has the option of exiting interview mode at any time by clicking on the appropriate toolbar button 424. The user can then move ahead or back and answer any question.

Login

Figure 23:
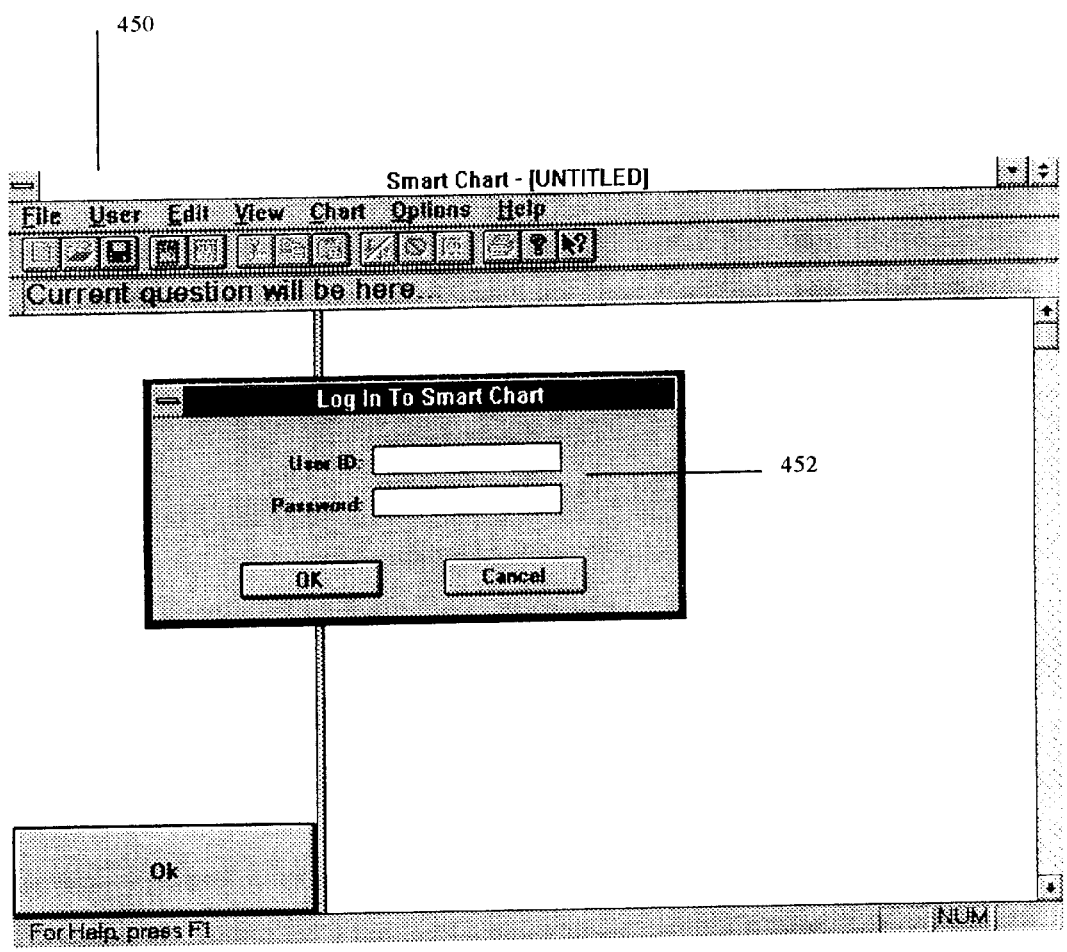
FIG. 23 is a screen snapshot which shows the login dialog box for name and password entry.
Figure 24:
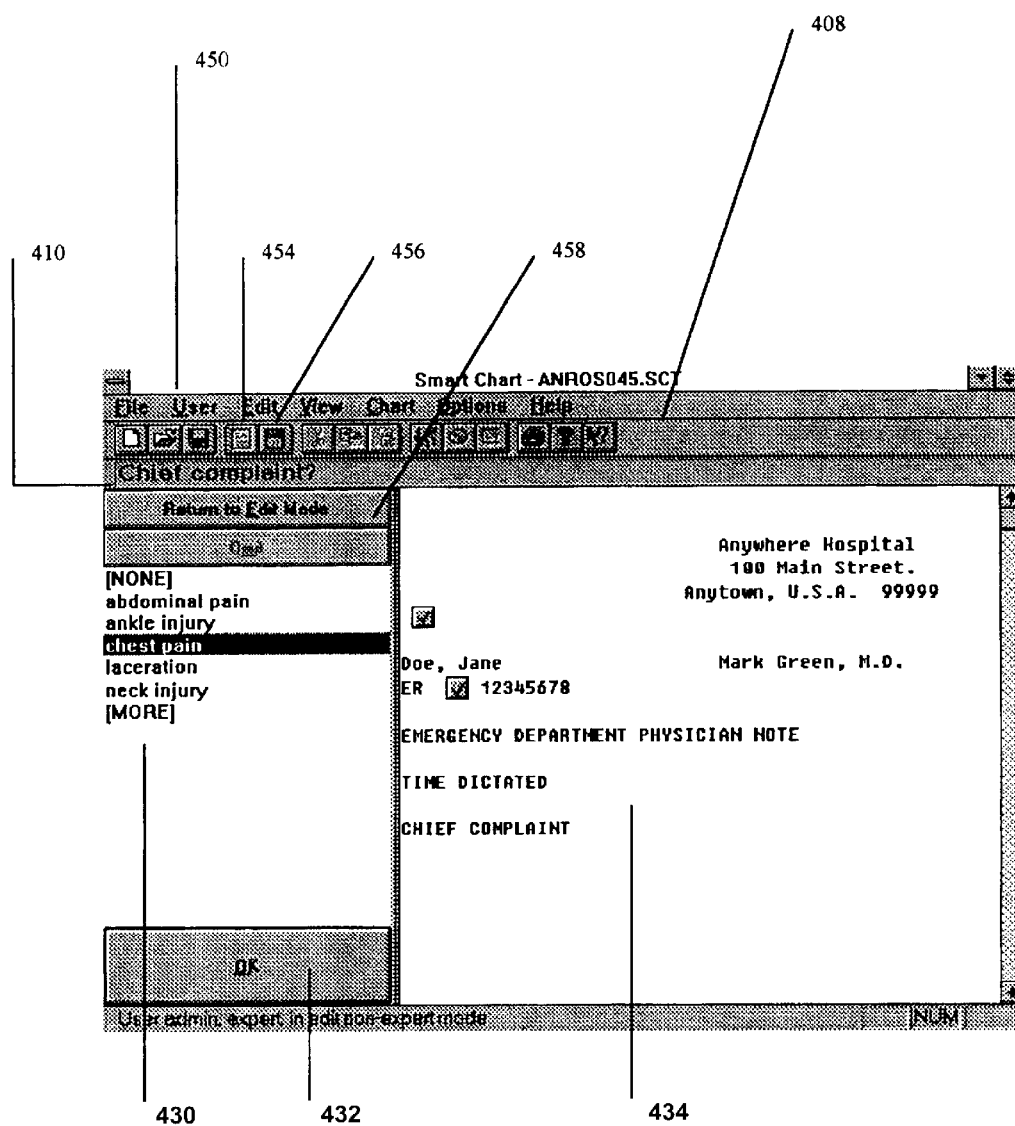
FIG. 24 is a screen snapshot which shows the login/logout buttons as well as other features.

Additional interface components of the preferred embodiment of the CaD program are noted in FIG. 23. These include login functions for password access. This is accessed for the first time by clicking on the User menu 450. This causes a password dialog box to appear 452. The user's name and password can them be entered into the appropriate boxes. This is necessary to track the user's level and may also be necessary if any of the documents are confidential in nature. FIG. 24 illustrates the CaD user interface and identifies two additional buttons. These are the login 454 and logout 456 buttons. Clicking on the login button 454 will call up the same password dialog as the login choice on the User menu. The logout button 456 and menu choice likewise have the same function. Activating either one of these will log the user out of the CaD program. When the program is running in interview mode a large button will be visible at the top of the pick list 458. By clicking on this button 458 the user may exit interview mode and return to edit mode.

Technical Description of Major Source Code Components

According to the current invention the execution module is written in C++programming language. It could presumably be written in another computer language. The following section is a listing of the component modules of the source code according the preferred embodiment of the present invention. According to C++convention all *.H files are header files and all *.CPP files are the actual source code modules. Because the actual source code consists of more than 65,000 lines of code the most important source modules will be described conceptually.

SCPARSE.CPP is the module 208 which performs the parse function which converts the knowledge base text file 204 into a knowledge base binary file 112. SCPARSE.H is the corresponding header file. The parse engine 208 translates the knowledge base text file 204 into the knowledge base binary file 112. All of the syntax rules 202 listed above are accordingly translated. These syntax rules are uniquely translated at the source code level. This syntax is not found in commercially available subroutines.

RMLOGGER.H is a definition file for a logger function. The logger is used to trouble shoot and debug the knowledge base as part of the parse process 208. It contains fairly standardized subroutines.

Because this invention is not based upon a word processor or a database the fundamental units of the program comprise persistent objects (POs) 210 which can be written to disk and later recalled. Some of the most basic and fundamental source code is demonstrated in FIGS. 25 and 26. RMPRSOBJ.H is the CaD PO base class definition file FIG. 25. All POs derive from this class. (Uses some Rogue Wave functions) SCDEFS.H is a file comprising definition of numeric constants used by all CaD POs. This file is shown in FIG. 23.

The following files contain the Object Class definitions 212 which are used to create the multitude of POs 210 used by the program. The various types of POs are noted in FIG. 7. Each file name listed below consists of a *.CPP implementation file and a corresponding *.H header file.

SCCHART is the definition of CaD document PO class 231.
SCDRWNG is the definition of CaD drawing PO class 239.
SCLIST is the definition of CaD list PO class 236.
SCNODE is the definition of CaD node PO class 233.
SCVAR is the definition of CaD variable PO class 237.
SCSECT is the definition of CaD section PO class 232.
SCVARSET and SCVARPTR comprise a set of files used to define templates and variables which are defined by pointing to other variables 238
SCTEXT is the definition of CaD text fragment PO class 234.
SCRULE is the definition of CaD rule PO class 235.

The CaD program 100 can exist in one of two forms. The CaD program generally executed by a user 102 comprises the basic runtime or execution or run-time program 214. There are two CaD files, CaD.CPP and CaD.H, that coordinate the overall functioning of the program. These files control such functions as list box displays used for opening and closing appropriate files and setting program defaults and preferences as recorded in an INI file. Additional CaD_EDIT files comprise an additional editing and parsing function 214 to be used by knowledge base developers 200.

Several of the PO classes 210 use C++programming language modules or classes from ROGUE WAVE TOOLS.H++™. The persistent object (PO) manager 224 class and the inference table manager 226 class use Rogue Wave's RWFileManager class software modules to perform allocation, reallocation, and de-allocation of space in files on disk. These same two classes also use Rogue Wave's RWBTreeOnDisk to perform binary tree access on various types of keyed data, including looking up the data on disk for a persistent object by its object id key, and looking up various components of inference tables on disk by their various keys. Several classes use Rogue Wave's RWBTreeDictionary to perform binary tree access to information stored in memory. These classes include the parse module 214, the PO manager 224, and the inference table manager 226.

Several classes use the Microsoft Foundation Class library (MPC), which encapsulates the Windows API. These windows API calls interact with the display, mouse, and keyboard. The classes which utilize these calls include the view manager 220, which is derived from MFC's CView class, and the display manager 222, which uses some MFC functions and is closely tied to the view manager. As in any MFC application, there are also classes derived from CWinApp, CFrameWnd, and various instances of classes derived from CDialog.

SCEDVIEW files comprise the view manager 220 which creates the interface of the SCEditView class. The view manager controls the primary view of text showing the wrapping document text and handling clicks in that text. It also handles such view functions as scrolling. The view manager interfaces with the knowledge base manager 218 and the display manager 222.

SCINFTAB files comprise the CaD inference table manager module 226. This module allows a variable to be reset or inferred based on the value of another variable. This module interfaces with the knowledge base manager 218 and object manager 224.

RMPOMNGR.CPP 224 is the implementation of CaD PO manager class. In order to add PO (PO) classes, see the rmpoclas.h file. That file must be modified, then the module is recompiled. While the file is open, the object manager actually works off of a temporary file. Only when the file is saved are the entire contents of the file copied back to the file specified. The application can call both file-level methods of this object (new, open, save, etc.), and object level methods (new PO, load PO, etc.). The PO classes 210 must be derived from class RMPersObj. When a PO manager object 210 is constructed, the name (and path) for the temporary file must be specified as well as how much total storage is needed by loaded personal objects. Note that even when a loaded PO is released by all other objects, the object manager 224 will continue to keep it in memory for fast future access until the total storage used by loaded POs 210 exceeds what is specified on the constructor. An application version is also specified. This version is stored with each PO's state information on disk, and passed to each object's restore state method.

It will be informative to the C++ programmer to describe how a new persistent object class is added to the persistent object manager. To do so, the programmer writes an object creator and object destroyer function for the new class corresponding to the prototype in RMPOCLAS.H. These simply perform a standard C++ new and delete for the new class. Then, the programmer modifies RMPOCLAS.H, adding an entry to the table of persistent object classes for the new class. Finally, the PO manager class is recompiled.

SCDSPMGR files comprise the display manager module 222. This module controls screen paints, fonts and printer support. Some of the grammar rules such as capitalization are incorporated in this module. This module interfaces with the object manager 224 and the view manager 2240.

SCCALLBK files contain global CaD callback function pointers, and the prototypes and functions that client code uses to set them. These files serve to interconnect the POs with the view and display managers.

Three significant portions of the actual source code are included as appendices. Appendix A is the code for the base class definition from which all of the POs 210 are derived. Much of the functionality of the CaD system is due to the complexity of the variable 244. The variable functionality 244 is encapsulated in the variable PO 237. Appendix B is the definition or header file for the variable PO 237. The C++ implementation file for the variable PO 237 is included as appendix C.

Summary

Like any invention, the CaD system builds upon previously known technologies such as persistent object programming read to and recalled from disk, decision node trees, scripting language, if/then logic and Windows graphical user's interface. These program structures are combined in new and unique ways with new methods of tracking a variable state, different types of complex inference and a unique knowledge base syntax language. The net result is a new and powerful tool for the production of technical documents.

OPERATION OF THE PREFERRED EMBODIMENT

Overview of the Process—FIG. 1

When implemented on a suitable hand-held tablet computer 130 CaD software 100 transforms such a computer into a device that guides a user 102 through an interview 106 of another individual 104. It also causes this computer device 103 to function as an efficient means of recording specific types of data. CaD is not intended to record random data elements such as generalized note taking. The CaD device is used for recording structured data gathered in a relatively systemic way. This structured interview function is created as the CaD program encounters a variable (VAR) 244 while executing. The CaD execution program 216 provides the user with a series of choices in the form of a list 256. The user makes a selection from the list 256 and the result is recorded as the value 270 of the variable 244. Although the data collection is structured and systematic for the purposes of speed and efficiency, the CaD program is still extremely flexible. In the preferred embodiment the CaD device is used for the purpose of taking a medical history. Such a use necessitates immense variation in the data to be recorded.

Power on Device

In its preferred embodiment the hand-held CaD device 130 is immediately ready for login when the device is powered on. The initial screen appearance is similar to that depicted in FIG. 18. After login the CaD execution program 216 is ready to begin the appropriate interview 106. The CaD device can be used in a wide variety of professions or fields and the appropriate knowledge base can be loaded as directed by an initialization file. The initialization file is indicated by the file extension "INI" and structured in accordance with conventional Windows standards. Other startup options can be designated by instructions recorded in this file as well.

Login/Password—FIG. 23

When the CaD program is first started by a user a login is typically required. This will be generally be password protected. Login serves two functions. In some embodiments the informations contained in documents might be of a confidential nature. The use of a password will be needed to restrict access in such cases. The second function of the login procedure is to determine the user level of the current user. This function is described in more detail in a later section. Once the user 102 has logged in, she is ready to begin the interview 106.

Interview

The CaD software guides the user through an interview by asking a series of questions. The answers to the questions are recorded as the contents or value of a variable. The first question asked is usually a general introductory question. The question appears in the prompt window 410. In the preferred embodiment the CaD software is used in a medical setting and the first question is "What is the Chief Complaint" ? This is in accordance with the established standards and conventions in the medical profession. Based upon the answer to the initial question the CaD device will prompt the user with subsequent questions to be answered. Generally these questions are answered in an appropriate sequential order although the user can jump ahead or go back and change an answer previously given. Sometimes the user has the option to omit a question. Some questions must be answered before the user can move along to the next question. These different types of questions are functions of the attributes of the variables 244 especially the variable type 282. These attributes are definable in the knowledge base 112.

Demographic Data

Because the CaD is a means for recording specific data from a specific source it will be customary to identify the unique source of the data. Thus some sort of identifying demographic information must be entered into CaD. In the preferred embodiment this value would be known as the medical record number, a number that serves to uniquely identify a particular patient. Regardless of the particular embodiment of the CaD program, this unique identifier can serve as a basis for the creation of a filename when a document is saved at a later date. In the preferred embodiment the medical record number could be chosen from a list of possible medical record numbers downloaded from the hospital computer. If the desired number is not found on the list then a special modal dialog appears which is used to enter the number quickly and easily. FIG. 12.

Figure 25:
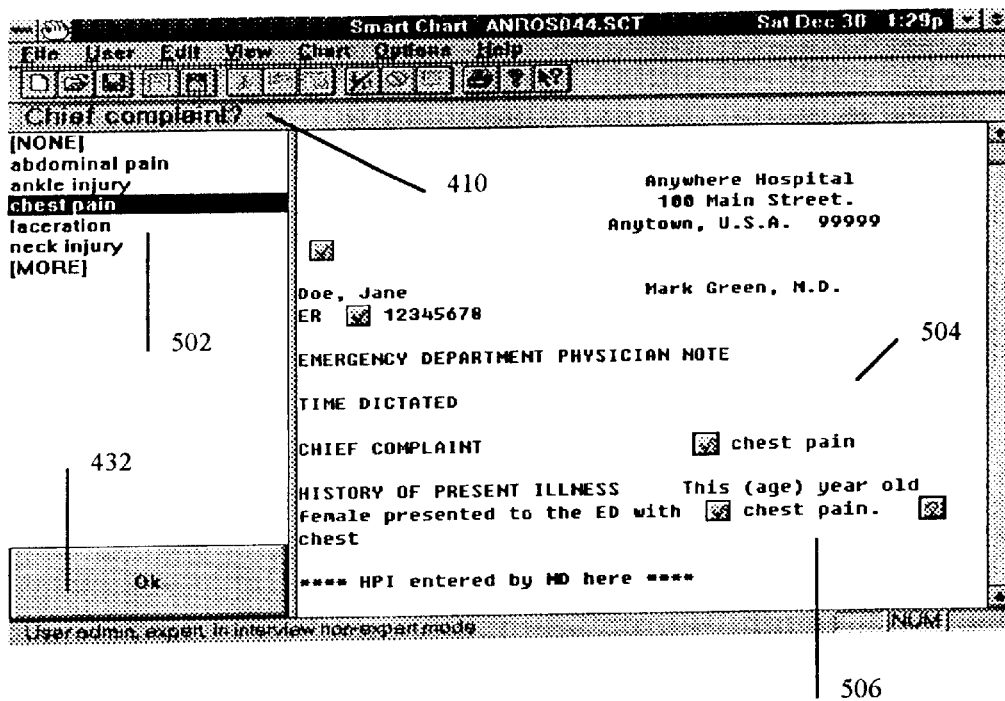
FIG. 25 is a screen snapshot which illustrates the most basic use of the input and output of a variable and the selection of the chief complaint in the preferred embodiment.

Simple Variable Input and Output—FIG. 25

The simplest use of the variable function is as a means of recording data and subsequent output of that data as text into the document. When the CaD software encounters a variable while executing, the value of the variable is generally output as text. If the variable does not contain a value or if the CaD program is being executed in interview mode, the program will prompt the user 102 for input. Once the user makes a selection the value is output in the proper position in the document. There are multiple variations of this simple scenario as outlined in the detailed description. FIG. 25 is an illustration of the basic use of the variable function. The current question is displayed in the window below the tool bar 410. A selection is made by the user, in this case a complaint of chest pain 502. Once the user clicks on the OK button 432 the selected value of the variable appears in the text 504. In this case the same variable is used again later in the document 506.

Figure 26:
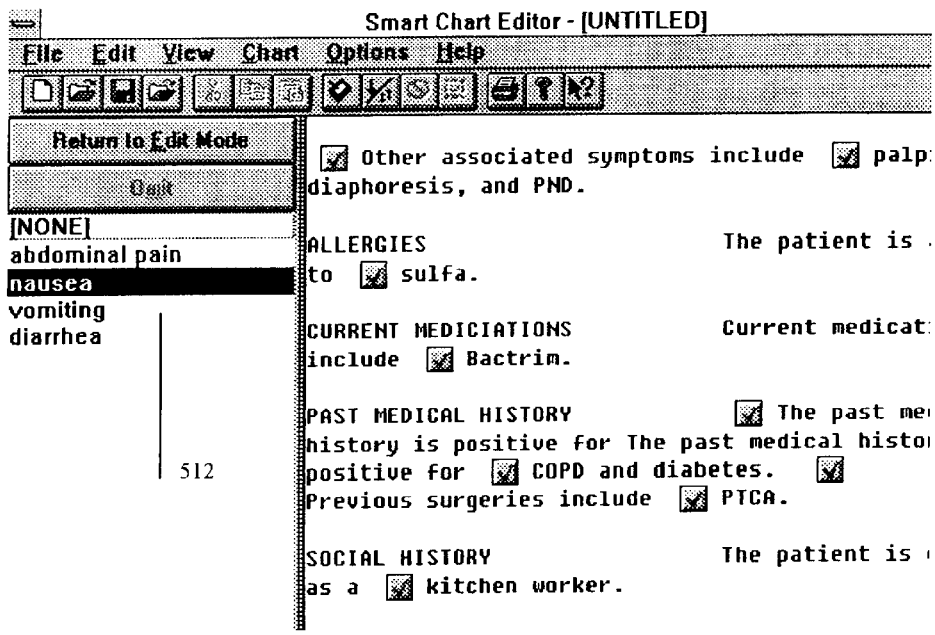
FIG. 26 is a screen snapshot which depicts example of input selection from a pick list for more complex manipulation of lists.
Figure 27:
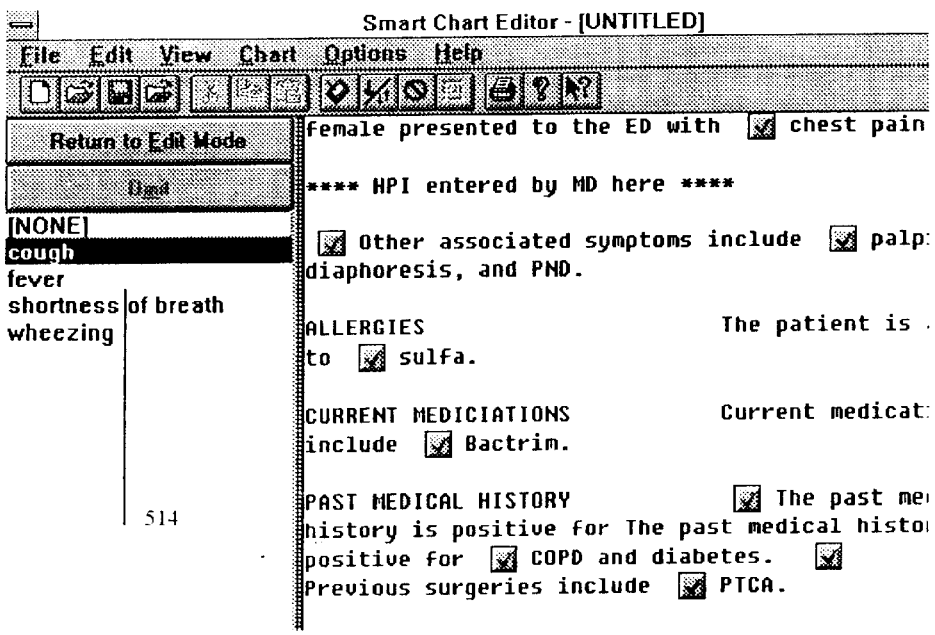
FIG. 27 is a screen snapshot which depicts another example of input selection for complex list handling as illustrated in FIG. 26.

Variable options—FIGS. 26–28

Most of the uses of a variable 244 in the CaD program involve simple variable display. There are however a wide variety of options or switches that can be used to cause the variable to display or behave in different ways. These various options, commands, and modifications are described in the detailed description. Two examples of the VAR command options are demonstrated in FIGS. 26–28. In simple cases only the selected variable is displayed. In some cases there is a reason to display an entire list or portion of a list. In the preferred embodiment there is a section of the medical history called the review of systems. This portion of the document is suited to such a display 516. In the taking of a medical history it is appropriate to ask a series of questions which are probably unrelated to the present complaint. There is a possibility that the patient may have some of these other symptoms and they may or may not be relevant. FIGS. 26 and 27 illustrate two lists which include further questions that might be asked when the chief complaint is chest pain. FIG. 26 is an abbreviated list of gastrointestinal complaints. Nausea is selected 512. FIG. 27 is an abbreviated list of respiratory complaints. Cough is the choice selected 514. FIG. 28 illustrates how these two lists may be manipulated to present the data in the document in different ways. The first sentence demonstrates the use of the \SETVARFROMSUM command 393. The selected choices from the lists displayed are combined and placed into a third variable. FIG. 28 demonstrates how the contents of this new variable can then be displayed with a simple VAR command 518. The following sentence illustrates a more sophisticated usage of the VAR options. The new third variable described above also contains a concatenated list made up of the sum of the contents of the two lists displayed in FIGS. 26 and 27. The combined, unselected choices contained in this variable can then be displayed 520 using the VAR \CONVERSE switch.

Dynamic Changes—FIGS. 29–37

Figure 29:
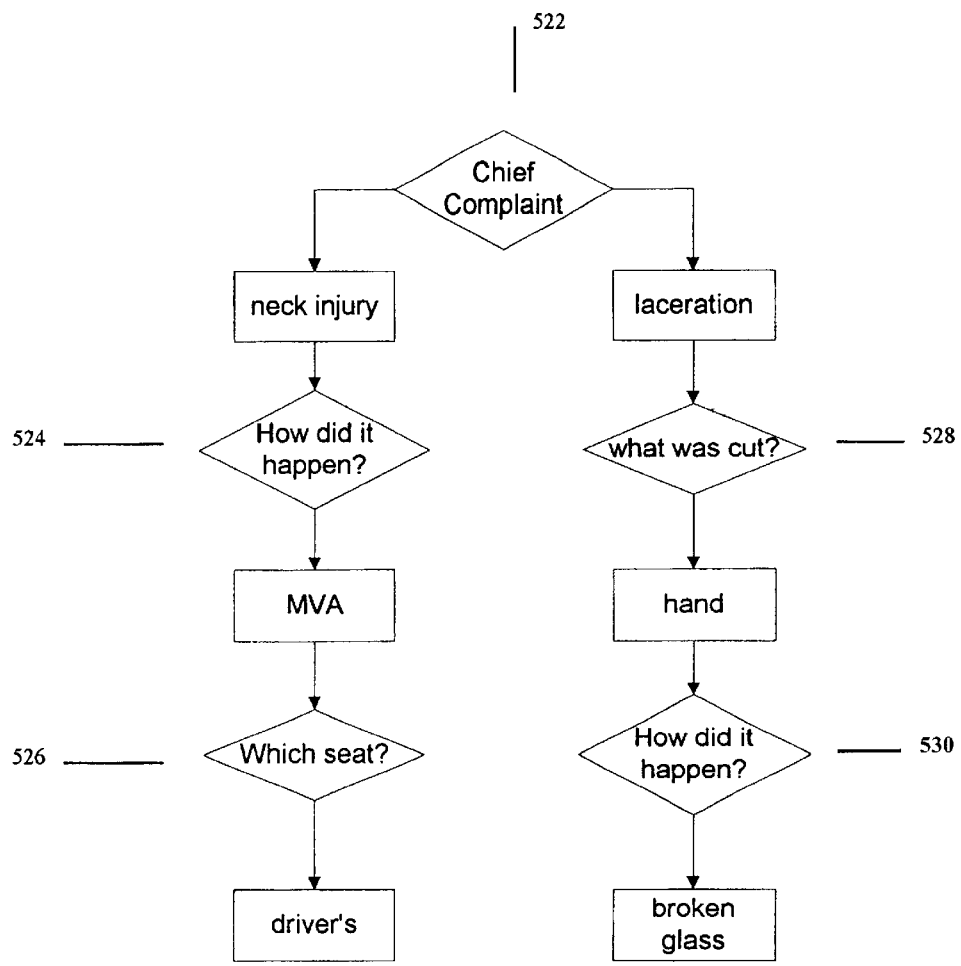
FIG. 29 is a flow chart which illustrates the potential for dynamic changes based upon user input.
Figure 30:
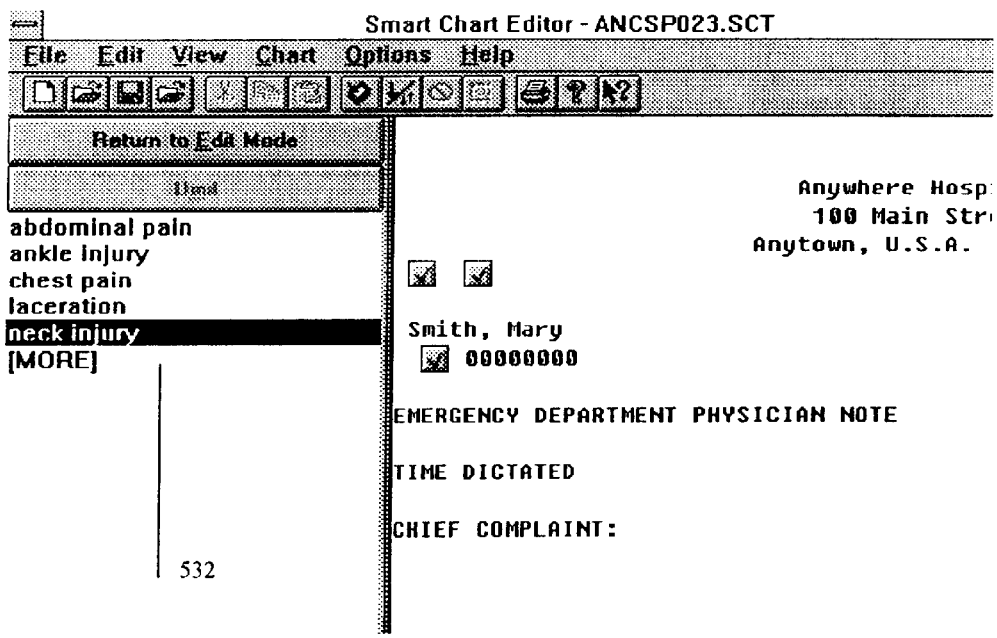
FIG. 30 is a screen snapshot which depicts input selection of a chief complaint of neck injury.
Figure 31:
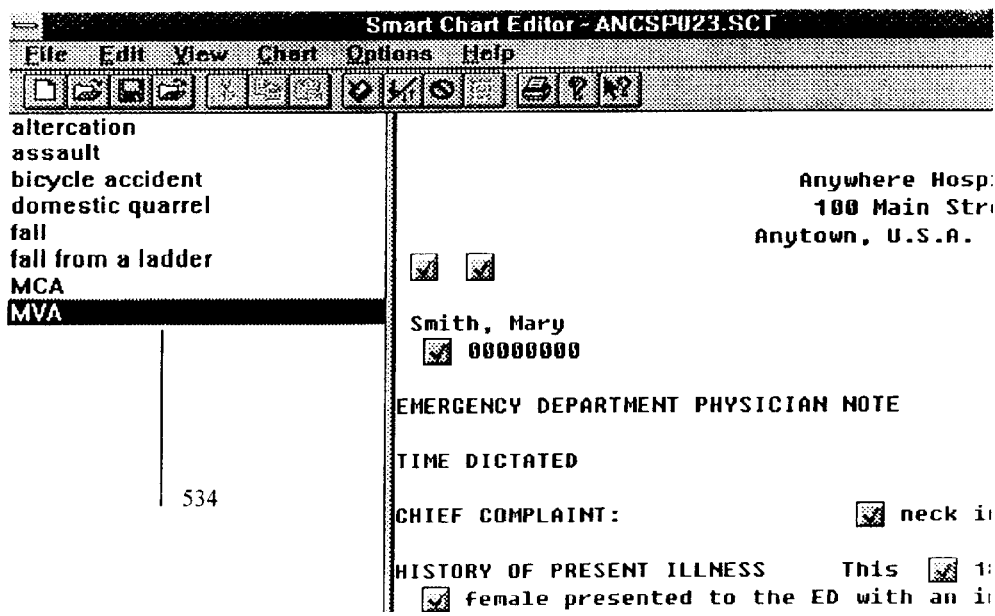
FIG. 31 is a screen snapshot which depicts context specific mechanism of injury choices presented to a user after selecting a complaint of neck injury.
Figure 32:
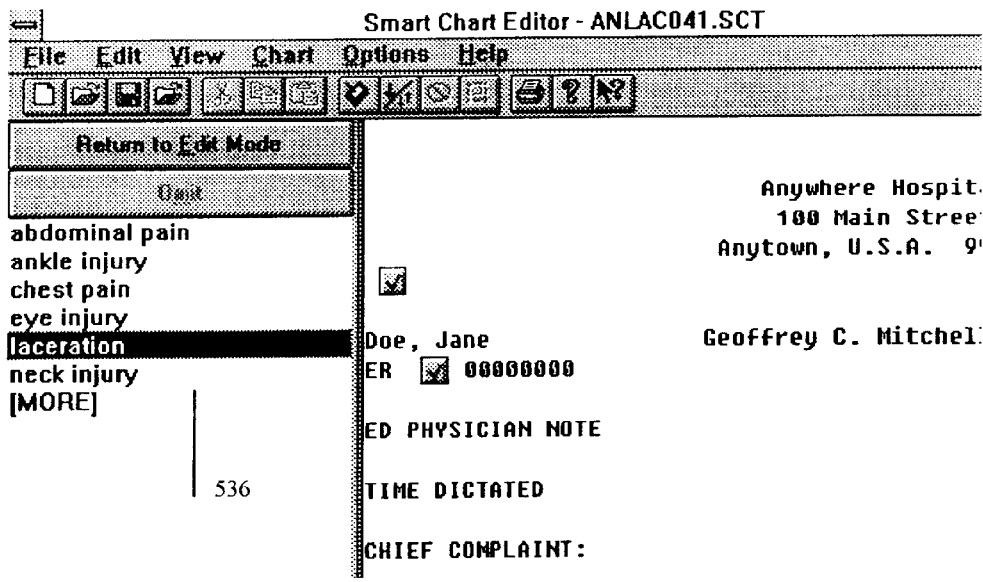
FIG. 32 is a screen snapshot which depicts input selection of a chief complaint of laceration.
Figure 33:
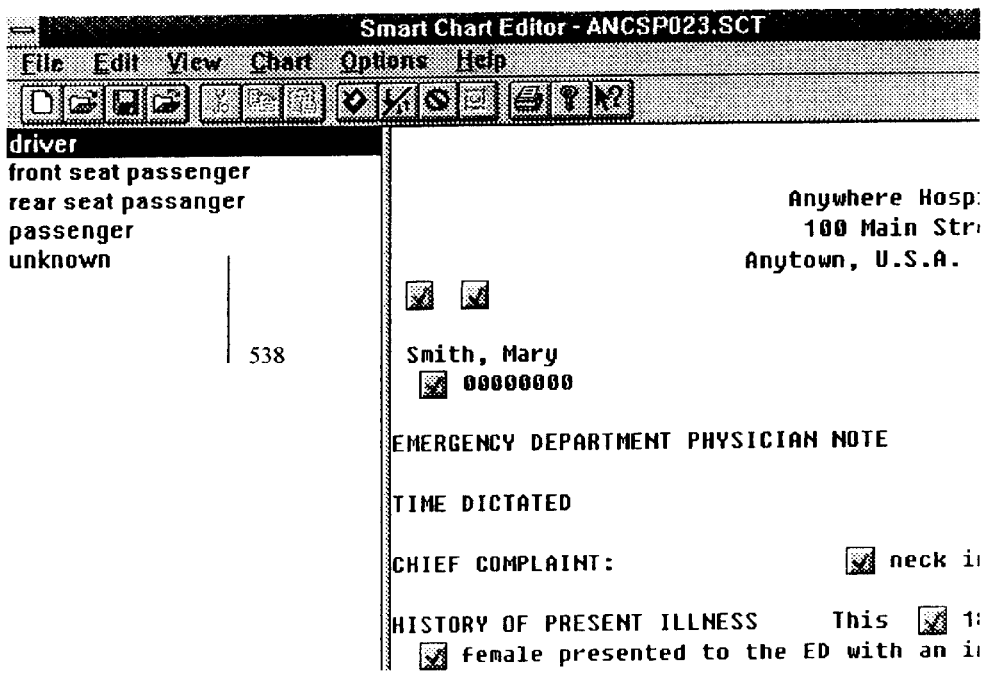
FIG. 33 is a screen snapshot which shows a context specific question, "Which seat in the car?", presented to a user after selecting auto accident as a mechanism.
Figure 34:
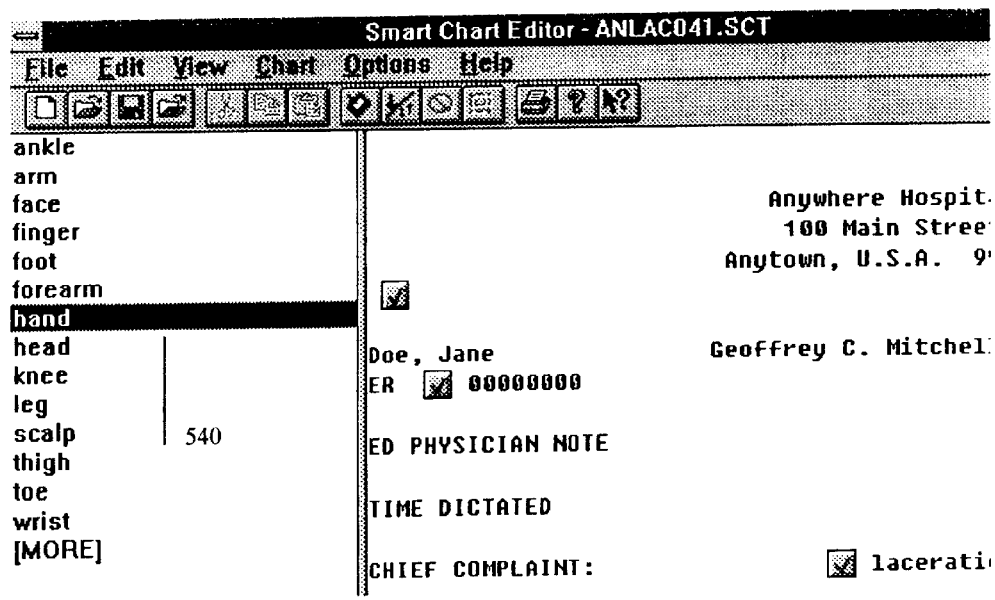
FIG. 34 is a screen snapshot which shows a context specific question, "Where is the laceration located?", presented to a user after selecting laceration as a complaint.

Based on the user's answer to each question, the CaD device may:

1) change the next or subsequent question(s) being asked. FIG. 29 is a flow chart that depicts this process and FIGS. 30–35 are actual screen snapshots that illustrate this function. In the medical context the start point in the taking of a medical hisitory is called the chief complaint 522. FIG. 29 simplifies this concept to two different complaints. In the preferred embodiment there would actually be a large number of possible complaints. FIG. 30 shows the selection of a type of complaint, a neck injury 532. Neck injury and laceration are similar in the sense that they are both types of injuries. Because they are both injuries it is appropriate to ask about the mechanism of the injury 524. How did the injury happen? In the case of the neck injury 532, the mechanism might be the appropriate second question 524. The screen display for the mechanism question is illustrated in FIG. 31. The choice selected for the mechanism of injury 524 is MVA (motor vehicle accident) 534. In the case of the laceration complaint 536, as selected in FIG. 32, the appropriate next question might be, where is the laceration located 528? The screen display for this question is illustrated in FIG. 34. The choice selected for the location of the laceration 528 is hand 540.

Thus these screen snapshots illustrate how in the CaD program, the next question to be asked is determined by the preceding question. Both branches of the node tree illustrated in FIG. 29 have a question about the mechanism of the injury 524 and 530. In the laceration pathway the question about the location 528 of the laceration is interposed before the question regarding the mechanism of injury 530. In the neck injury pathway on the left, the logical second question is, How did you neck? 524. Because the neck injury 532 was caused by a motor vehicle accident 534, a logical third question is "which seat of the car were you in? 526. The screen display for this question is illustrated in FIG. 33. The choice selected from the list is "driver's seat" 538. Neither this question nor this list would make any sense in any other scenario. The questions asked are context specific.

Figure 35:
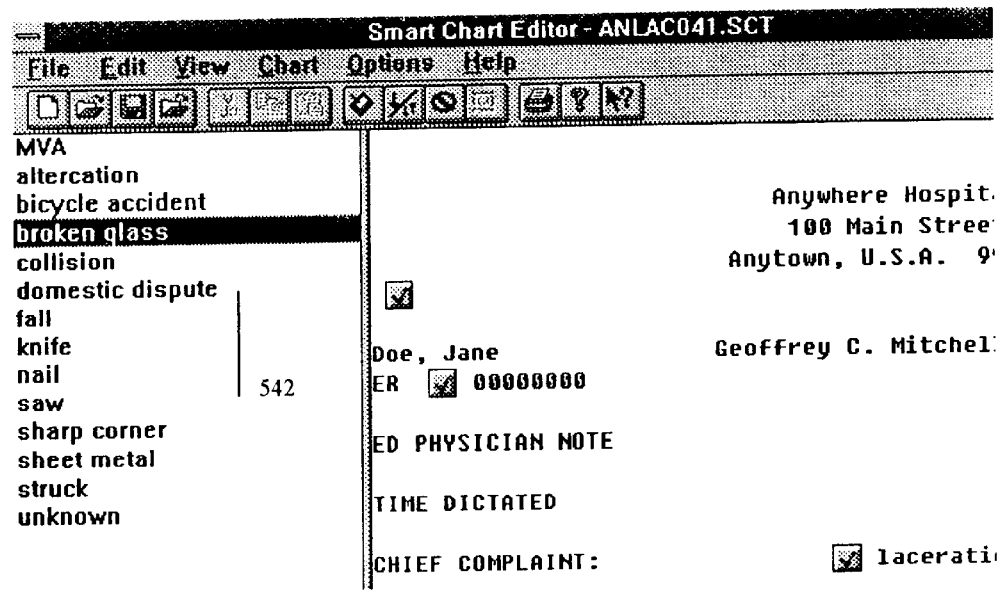
FIG. 35 is a screen snapshot which depicts context specific mechanism of injury choices presented to a user after selecting a complaint of laceration.

2) change the list associated with a given question. FIGS. 31 and 35 both illustrate a pick list associated with a variable known as the mechanism of injury 524. Both of these lists contain possible choices to answer the question, How did this injury occur? However, each of these lists contains answers that are appropriate to the context. A neck injury is likely to occur as a result of a motor vehicle accident (MVA) FIG. 31. It is essentially impossible for a neck injury to occur from a broken glass 542, FIG. 35. A broken glass is, however, a very likely to be the cause or mechanism 524 of a laceration 536, FIG. 32. Comparison of these two FIGS. (31 and 35) reveals that the lists are different even though the question being asked is essentially the same i.e., how did your injury occur? These two FIGS. illustrate how the list 256 associated with a question can change in response to a previous question. The list 256 associated with a particular question or variable 244 is context specific as well 3) change the text output being generated in the final document, FIG. 36. An important functional aspect of the CaD program is that it is "smart" in the sense that it has appropriate grammar rules incorporated into the program. FIG. 36 is a good example of this functionality. In the first frame a pick list is depicted 552. The question being asked is "What is the patient's occupation?" 554. The second frame illustrates that the choice of "clerical worker " has been selected from the list 556. The third frame illustrates what happens if the choice of "disabled" has been selected from the same list 552. While disabled might be an appropriate answer for the question this word does not fit into a sentence the same way. It would be inappropriate for the chart to read "The patient is employed as a disabled." In CaD the sentence structure changes if this different choice is made 558.

4) change the structure of a document. FIG. 37 is an abbreviated example of a document (medical chart) produced by with CaD in the preferred embodiment. This scenario describes a patient with an injury to the left ankle 562 and some pain in the right knee 564. In such a situation, good medical practice dictates that the examiner should examine the adjacent joints. It is not appropriate to examine the entire body in the case of a simple ankle sprain. An adequate medical chart would not address unrelated body parts and organ systems in such a case. In the illustrated case it would be inappropriate to include information about the head, neck, chest or abdomen. It would not even be customary to say they are normal or irrelevant or not examined. The astute reader knows these areas need not be examined.

In the example shown in FIG. 37 the physician is reminded to examine the left knee 566 because it is adjacent to the injured ankle. The painful right knee 568 is examined in greater detail 568. The injured left ankle is likewise examined in detail 570 because it is the area of the patient's primary complaint 562. The physician is also reminded to examine the right ankle 572 below the painful right knee. The right ankle was normal as would be expected. Notice that there is no exam of the head, neck, chest, or abdomen. It is not necessary to examine these areas in such a case.

This example is a case of moderate complexity with two different complaints. Other cases require the examination of a certain body area and comments that the exam was normal. CaD is able to track such cases and prompt the user to examine and document the proper areas of examination. CaD can do this even with multiple complaints. A template system could be used for a single complaint such as ankle sprain. The template could include the pertinent examination and omit the other areas. A template system, however, could never combine two different complaints in a meaningful way. This would require designing a new template for each and every possible combination of two complaints, then a different template for each combination of three complaints, etc. This would quickly become an impossible task. CaD can alter the structure of the document in a context specific fashion based upon the answers to the questions.

User Mode—Expert/Interview

In the preferred embodiment the user has a choice of two modes of operation. This is related to the concept of user level but is not exactly the same. In "interview" mode the CaD program will stop at each question and wait for user input. This happens regardless of whether a question has a defaulted or inferred answer. If an answer is defaulted or inferred it will be highlighted by the cursor on the screen. The use must still click on the "OK" button 432 in order to proceed. This mode is suitable for students and less skilled users of the CaD program. CaD was not originally designed as an expert system in the usual sense. In the preferred embodiment CaD is used to produce medical records. When people think of computers in medicine they often think of computer derived diagnosis. This is not the role of CaD in the preferred embodiment. CaD does however, function as an expert system in the sense that it can be used to train a less experienced worker. In the interview mode the user is literally walked through the thinking processes of the domain expert in a step by step manner. In this limited sense then, CaD is an expert system.

In contrast, the use of the "expert" mode causes the CaD program to skip over questions that have a defaulted or inferred answer. The CaD program will stop only at those questions which are not yet answered. If the user wants to change a particular defaulted answer, he may do so using the edit mode. The expert mode is called that for a reason; it assumes the user is intimately familiar with the CaD program. In this case the expert mode can greatly increase the speed and efficiency of similar documents. In the preferred embodiment the physician user might use this feature to skip ahead to enter the diagnosis. The diagnosis would then have several implications for the final document (medical chart). The physician user would then fill in unanswered question and edit the inferred questions as needed. The expert user must be aware of the default values and review and edit the document. A beginning user would be restricted from using the expert mode. This is accomplished by the use of a password system and a classification of user privileges.

The Power of Inference

In the preferred embodiment the CaD device functions in such a way as to allow an expert user to prepare documents more quickly and efficiently. This is especially true in the expert mode as outlined above. The speed and efficiency of the expert mode are only partly derived not only from the fact that the CaD program skips ahead to unanswered questions. The more important factor is the fact that so many questions can be answered automatically by defaults and especially by inference. In the CaD program there are different types of inference available to the knowledge base programmer. This feature is especially useful in the preferred embodiment. In a medical record the answers to certain questions such as the chief complaint or the diagnosis may have a multitude of implications in terms of history taking, physical examination and diagnostic testing. Although these inferences can be incredibly complex, CaD provides tools for identifying these inference relationships and utilizing them to improve documentation and hopefully to ultimately improve the care being given.

In the CaD program there are at least 4 different types of inference available. These differences are invisible at the user level but the subtle nuances would be important to the knowledge base programmer. The inference tables 248 are especially useful when the answer to one question has implications for many other questions. In the preferred embodiment an example of such a question might include the chief complaint or the diagnosis. The various types of rule inference 392 are useful for one to one inference relationships. These rules are also used for more complex types of inference relationships. For example, the particular combination of two or more answers or variable values might imply the answer or value for a third question. Rule inferences are discussed in the detailed description. Default is a particular type of inference which is used when a particular question has a single, most likely answer.

The use of inference can speed up the documentation process for the expert user. FIG. 38 is an example of the expert mode and inference. Again this is an abbreviated section excerpted from a document produced with CaD. This is an example of the preferred embodiment, a medical record. This example of inference is based upon the preferences of an individual physician user. A physician is likely to perform similar procedures in similar ways with occasional minor variations. CaD allows these types of preferences to be preprogrammed for the sake of expediency. In this example Dr. Lewis is a modern doctor 574. She uses Xylocaine anesthetic, nylon sutures, and Neosporin antibiotic ointment 576. Dr. Welby 580 on the other hand, is an older doctor with different preferences. He chooses Novocain anesthetic, silk sutures, and sulfa antibiotic ointment 582. In the abbreviated example shown in FIG. 38 these charts look otherwise identical and it may appear that this is a simple template system. This is not the case. These documents may be modified and embellished in a whole host of ways as outlined elsewhere in this document. In this illustrated example only one modification is demonstrated. Nothing was changed except the doctor's name. This FIG. demonstrates one type of inference function 248.

Bi-directional Inference

One important and unique feature of inference in the CaD system is that it can operate in a both, directions. That is, reverse to the normal flow of the document and reverse to the apparent thinking process of the user. This has been alluded to previously but it is an important component of the CaD program. It is particularly useful in the expert mode of the preferred embodiment. Laypersons often assume that computers will someday replace physicians or that computers will assist physicians in making diagnoses. Although there are certainly some examples where this might be true, experimental trials have generally failed to confirm the value of the computer in this arena. There are probably two reasons for this. The first is that in medicine, the very process of data collection generally requires a physician's expertise. When a less experienced individual collects data for input into the computer there is often an interpretive process that takes place between the patient and the data entry process. Thus this data is subject to the garbage in, garbage out phenomena. The second reason why computers are not helpful in diagnosis is that the diagnostic process may not be the algorithmic process most believe. The diagnostic process is probably more akin to a pattern recognition process. Some have likened this to the process of recognizing someone's face. Computers have thus far been unsuccessful in face recognition.

This has important implications for the CaD program in its preferred embodiment. Physicians can often arrive at a correct diagnosis more quickly than a computer. The documentation process often takes more time then the diagnosis. A medical diagnosis carries with it many expectations and implications in terms of historical details, physical findings and diagnostic tests. However, many of these must be documented and cannot be assumed. For example, a diagnosis of a broken ankle almost always implies that an X-ray was taken and demonstrated a fracture. This diagnosis also implies that the ankle should have been examined. The head may or may not need to be examined depending upon the circumstances. Countless other examples could be cited. In the expert mode and the preferred embodiment, CaD can work backwards from the medical diagnosis. Elements of the document are generated and the user is prompted for the pertinent information based upon the "bottom line". This concept of "bi-directnal inference", i.e., the ability to build a document backwards based upon the final answer, is in important functional attribute of the CaD system.

User Level

Three classes of users are defined in the preferred embodiment. These can be simply described as beginner(interview), intermediate and expert or advanced. In a specific embodiment these levels might have more specific definitions. In a medical setting they might be labeled technician, nurse, and doctor. The user level has implications in terms of various privileges granted in the running of the CaD program. User level also plays a role in inference function. The user level is inferred from the user name. It is recorded as a simple variable but then it can be used in a whole host of inference rules.

Variable State 272

Inference rules can become quite complex. This is especially true if the CaD system is used in a complex field such as law or medicine. It is easy to imagine potential conflicts between two different inference rules. The CaD program has an additional feature which allows it to process potentially conflicting inferences. The CaD program tracks of the "state" of each variable 272. This is a record of how a given variable came to contain its current value 270. The CaD program records whether a variable has been selected as a default value, inferred by the value of another variable, or manually selected by a user. CaD also maintains a record of the level of the user who selected an answer contained as a variable value 270. On the functional level the user never directly enters or changes the state of a variable. The state is hidden from the user. The state is tracked and recorded automatically by the CaD software.

The implication of this is that the CaD program remembers if a particular answer was manually selected by a user. If so, it will not override the answer with an inferred selection. Thus the selections entered manually by the user will be preserved. Another use for the variable state is when a given document is being prepared by more than one individual. If one user is an expert and the other user is a beginner or helper, then the helper will not be able to override a choice made by the expert user.

Execution Mode—Interview/Edit

In the preferred embodiment CaD has two modes of execution, two ways in which the user can interact with the device. The first is called interview mode. This is the mode described above. The CaD program is usually started in interview mode. When the user completes the interview by answering all of the questions, the CaD device automatically changes to edit mode. The edit mode is usually used after all or part of a document has been generated. The user does not have to complete the interview all at once. The user can switch to edit mode at any time. The user can also save the current document to a file and change to another file or exit the CaD program entirely. A file closed in this way can be reopened later by the same or another individual user.

As the name implies, the edit mode allows the user to edit text which has already been generated. The edit mode is illustrated in FIG. 21. The edit window 434 has a conventional Windows type scroll bar 438 along the right hand margin. The four types of edit buttons are described in FIG. 22. When a user clicks on an edit button the associated pick list will appear in the left window 430. The associated user prompt, i.e., the question being asked appears in the window 410 below the tool bar. The user may then click on an alternative selection. This process is identical in both the interview and edit modes. Once the user has selected an answer and entered the selection by clicking on the OK button 432 she is free to edit another portion of the text.

Figure 39:
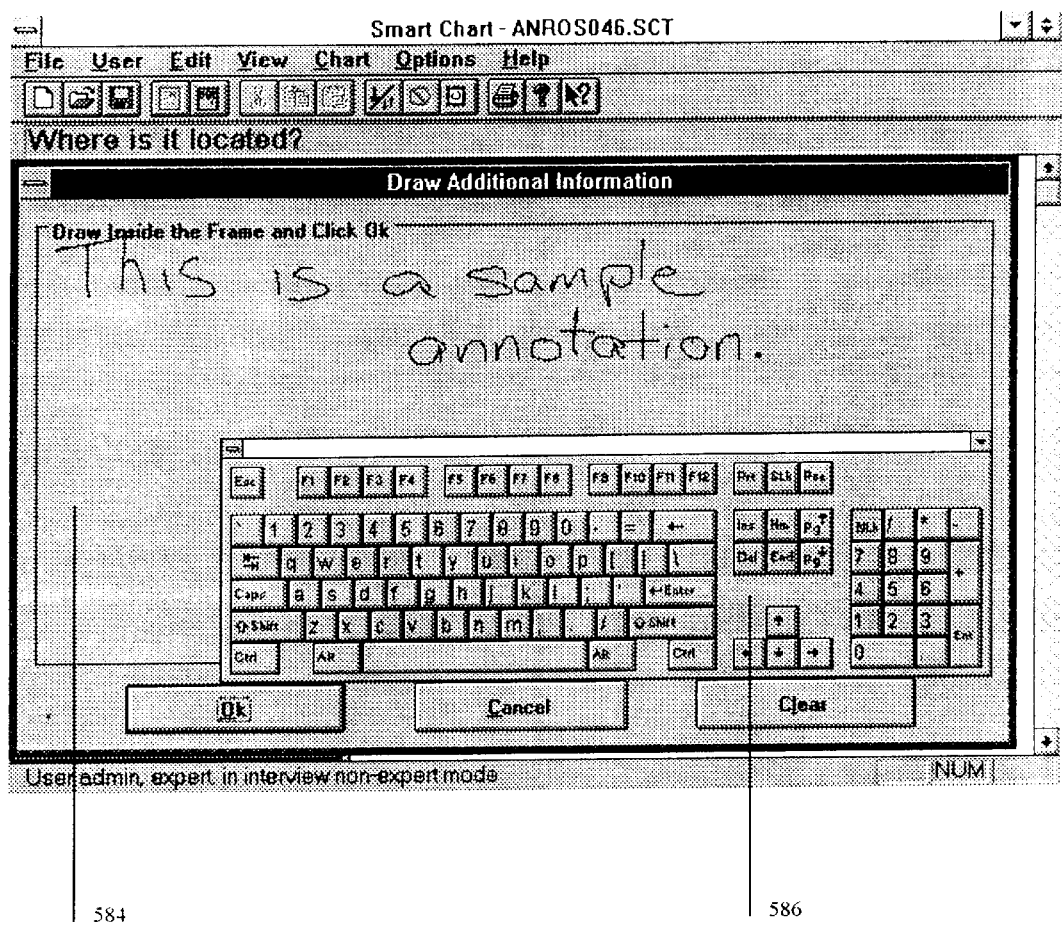
FIG. 39 is a screen snapshot which depicts two alternate means of text input, a free text annotation and a pen driven input keyboard on the screen.

There are three additional ways to edit the document by adding text. Two of these are illustrated in FIG. 39. Editing may also be accomplished by marking the text and appending additional material by writing in a drawing window with the pen 158. The user can write a freehand note 584. This note attached to the document and saved to disk as a bitmap image. The user may also enter additional text by means of commercially available handwriting recognition software which is also loaded on the CaD computer 130. Such adjunctive software is not very efficient at the present time but may become more useful in future embodiments. The third alternative way to enter data is by means of a keyboard overlay 586 program. The pen input device 158 can be used to click on the individual keys as depicted on the screen. This too is a commercially available product which may be loaded on to the CaD computing device 130 for the purpose of entering data into the CaD program.

Figure 40:
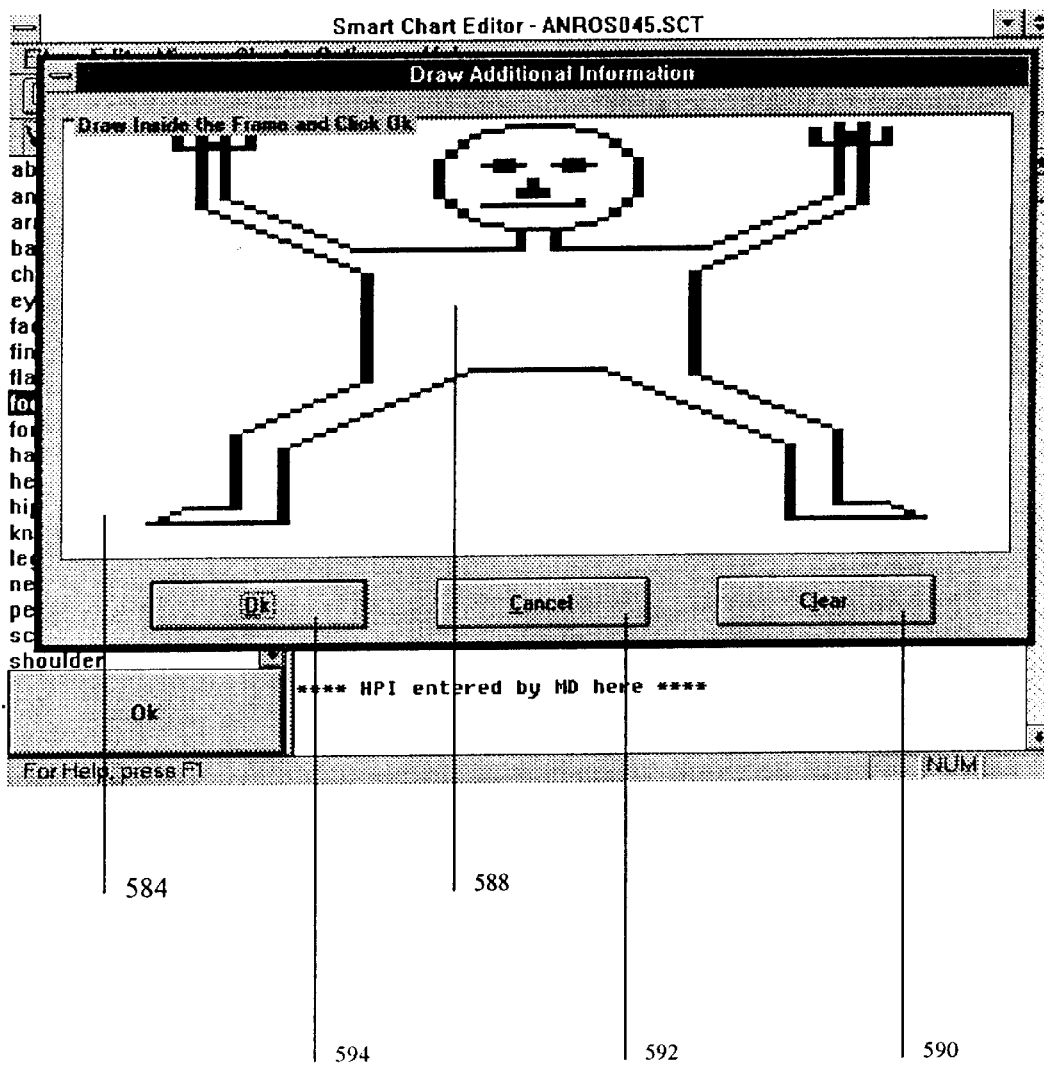
FIG. 40 is a screen snapshot shows an example of a drawing template.

Drawings—FIG. 40

CaD allows the user to add drawings to a document. These drawings are meant to provide a visual description of something that might be very difficult to describe within the structured format of CaD. Certain variables can be programmed to accept an associated drawing. If a drawing is available or allowed to be associated with the current variable, the drawing button 428 on the toolbar will be highlighted. If the user then clicks on the drawing button 428 then a window 584 will open and the drawing 588 will be displayed. FIG. 40 illustrates a prototypical drawing template. Higher quality bitmap images can be used. The drawing is not simply appended as a separate file, but is actually incorporated into the final document. Once the drawing window is opened, the user edits may be cleared from the screen 590, the window may be closed and the edits canceled 592, or the edits may be accepted and saved 594.

Typical uses of the drawing function might include a map or a description of an auto accident. In the preferred embodiment, drawings might be used to show the location of a particular injury on the surface of the body. The user might call up a particular template drawing. These templates are stored as bitmap images. The user can add pertinent details and saved the modified drawing 594. Drawing templates can also be inferred. Thus an eye injury might infer a template showing a diagram of an eye. The user could then draw on the template a representation of the particular injury in question. Drawings are saved to disk and incorporated into the final document.

Save for Later Edit

The CaD program 100 is capable of saving the file to disk 146 with an automatically generated file name. A file name may be generated internally from some piece of demographic data. This information is stored in and retrieved from a specific variable of the variable type FILENAME 364, FIG. 17c. In the preferred embodiment this file name is the patient's medical record number, a number which is uniquely attributed to each individual in a particular hospital or health care system. This file can then be opened at a later time for editing or for adding information 228. The persistent objects 210 and their relationships to each other are maintained. Thus, when such a file is recalled from disk, it appears identical to its previous state. It can be edited in the edit mode. If the interview 106 was not previously completed, it can be continued at this time. With this function different workers 102 can contribute information to the same document. For example, in the preferred embodiment doctors and nurses could each contribute to a particular patient record.

Complete Record—FIG. 41

Once the document is completed it is saved to disk and exists in an electronic format. This may be a simple ASCII text file (assuming there are no drawings or appended notes) or the file may contain formatting according to the particular embodiment. This electronic file may be transmitted across a wireless network or printed later in a batch format. The electronic file may be transmitted by phone lines and modem to a distant location. In the preferred embodiment this electronic file may be archived in a clinical information system to comprise a portion of an electronic medical record.

Print Output

The document produced by CaD may be printed 110 locally or distantly. It may be printed immediately or at a later time. In the preferred embodiment the document is printed immediately by transmitting it over a wireless LAN 134 to a designated printer.

Save Text to Archive

Once a user decides that a particular document is complete it may be saved to disk in a text format. In this format the persistent objects and their relationships are not saved. Thus the file size is dramatically reduced and more files may be saved to disk 146. A file saved in this format 120 might be edited in a text editor or word processor but not in the CaD program.

Export to Database—FIG. 42

Any variable in the CaD system can be marked for export function. Any data thus collected under this variable name 596 will then be stored in a database. The database will contain field names 597 defined by the exportable variables. Each record will be defined by the unique document names or numbers 598. An abbreviated sample database is depicted in FIG. 42. This database exists only for the purpose of recording data for future analysis. The CaD system is much more than a database front-end. The functionality of CaD is in no way built upon a database file structure. The database thus constructed may be utilized for outcomes analysis and scientific research. The database is ODBC compliant. It may be opened by standard commercially available database programs. The unique aspect of the database created by the export function of CaD is that the state of each variable is recorded as well. This has implication in quality management studies. E.g. who selected a particular choice or how many times did a certain user make certain selections. The information collected by the CaD program and stored in the various variables can be sorted, filtered and analyzed for relationships between the various data elements.

Role of the Knowledge Base

The preceding functional elements of the CaD program require the existence of a suitable knowledge base (KB) 204 previously prepared by a domain expert 200. A knowledge base has been prepared for the field of emergency medicine according to the preferred embodiment of the present invention. A particular knowledge base is not necessarily part of the present invention. The same functionality could be produced by different knowledge base scripts. The syntax rules enable the CaD program to interpret a knowledge base and carry out the unique functions described above. The knowledge base syntax comprises a new and unique programming language 202 which is an integral portion of the present invention. The knowledge base syntax 202 is further described in the detailed description.

Figure 43:
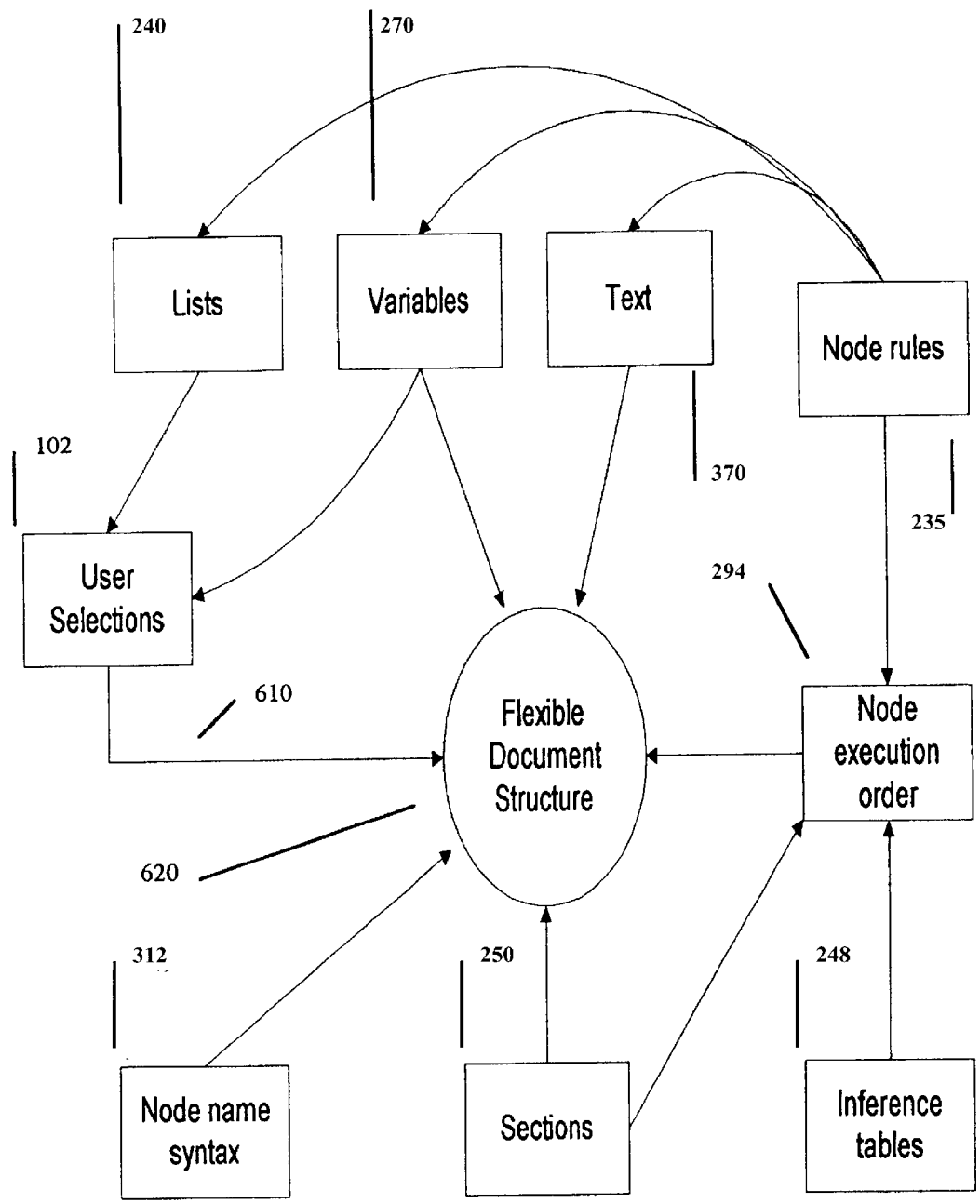
FIG. 43 is a flow chart which illustrates how multiple factors contribute to flexible document structure.

Overview of Document Modification FIG. 43

FIG. 43 is a complex flow chart that illustrates how these features come together to produce a powerful tool for document production known as CaD. The fundamental building block of document construction is the node. Node objects are serialized or executed in a specific order 602. Nodes cause various types of PO's to output their contents to the document. These can include straight text 604 which is not directly manipulated by the user but goes straight to the document. Variables 606 can output their contents to the document if they contain a value. If the value contains no value the user 102 will be prompted to make a selection 610. This is accomplished by presenting a pick list 608 to the user 102. In most cases the pick list does not appear in the document but only the choice selected from the pick list 608. The basic node order is defined in the knowledge base by the definition of sections 614. Sections give a basic structure to the document. Sections are often defined according to professional traditions or local custom. The sections portion of the knowledge base contains a list of nodes associated with each section. These nodes are executed in the given order as each section is executed in order. The particular order of node execution can be further modified viavis the use of inference 616. This is a most sophisticated means of modifying a document. It is independent of direct user input (although the user's input of a certain variable may have instigated the inference cascade). Finally the power and flexibility of the CaD program may be further enhanced by the selection of a suitable scheme for naming nodes, variables and lists. A suitably organized syntax can allow the domain expert to program a knowledge base which can guide the user through a large number of potential scenarios according to the conventions of a particular field of expertise. All of these features and components then interact in the ways described above to create the CaD system. The result is a powerful tool for the production of technical documents. Documents produced by CaD are flexible, varied, and professional 620.

Figure 44:
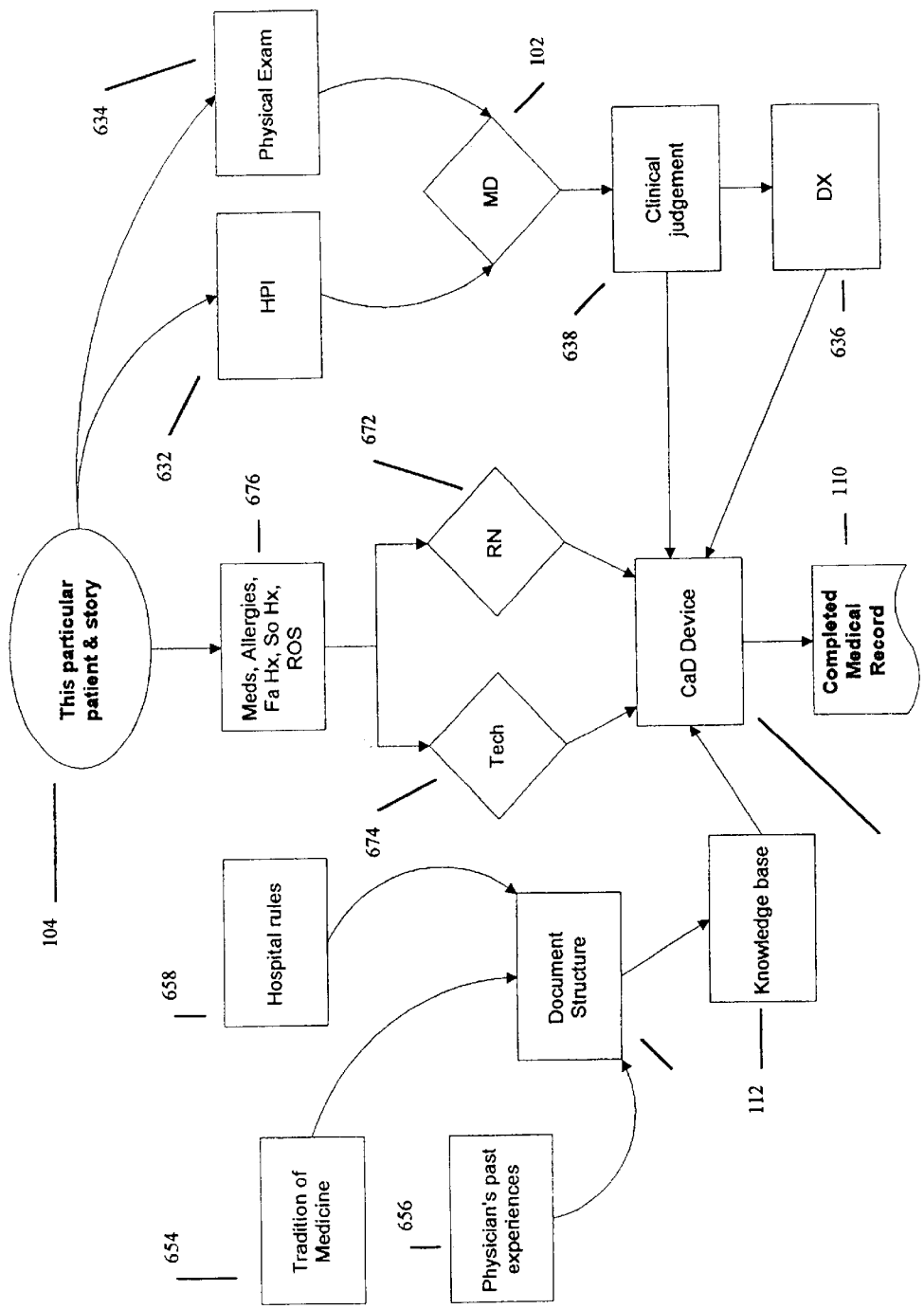
FIG. 44 is a flow chart which illustrates steps to generate a medical record document in a hospital emergency department according to the preferred embodiment.

Overview of Medical Record Production in the Preferred Embodiment FIG. 44

In its preferred embodiment the present invention is designed for the efficient production of medical records. An overview of this process and the role of the CaD program is depicted in FIG. 42. The process begins with a particular patient 104 who presents for treatment in an emergency department. The peculiar events leading up to this visit are known as the history of the present illness (HPI) 632. This information along with the particular physical findings 634 must be noted by the physician 102, the primary user of the CaD device 130. Once this information is recorded it is known as the patient's medical record 110. This most important piece of information which is generated by the physician user 102 is the diagnosis 636. In a very real sense the entire document revolves around the diagnosis. The diagnosis must make sense out of the preceding data, the patient's history and physical exam. The correct diagnosis 636 is a precursor to the correct treatment. The medical record document 110 should tell a story to any other physician who reads it. Ultimately the physician decides 638 to add material in order to make the record more complete or perhaps to withhold material to make it more readable. The medical record has been recorded in a fairly structured narrative format 652 for generations. The reasons for this are beyond the scope of this document. This format varies somewhat from one location to another but is remarkably consistent throughout the world 654. There is some variation based upon a physician's past experience and training 656. There may exist local hospital rules that require minor modifications to the document 658. The chart structure is defined in the knowledge base file 112.

Some have tried to abbreviate or modify the format of the medical record in order to provide for better ways to handle and communicate this information. These attempts have been met with little success. The preferred embodiment of the CaD system offers a way to facilitate and improve the process of medical documentation while maintaining records in their time tested traditional format 652. The physician is the primary user 102 of the CaD device 130. She or he can input data directly into the hand-held mobile computer 130. The CaD software 100 offers many tools for enhancing the medical record and recording it quickly and efficiently. These functions have been previously outlined in this section. In the preferred embodiment the process can also be improved by utilizing other personal such as nurses 672 and technicians 674 to contribute to the document. Some of the information 676 that must be collected is well suited to entry by nurses and ancillary personal. Some information could be entered by patients themselves 104 or by family members. According to the preferred embodiment of the current invention, Computer-assisted Documentation, these multiple users can each enter data into the mobile, hand-held computer 130 which executes the CaD software 100.

Figure 45:
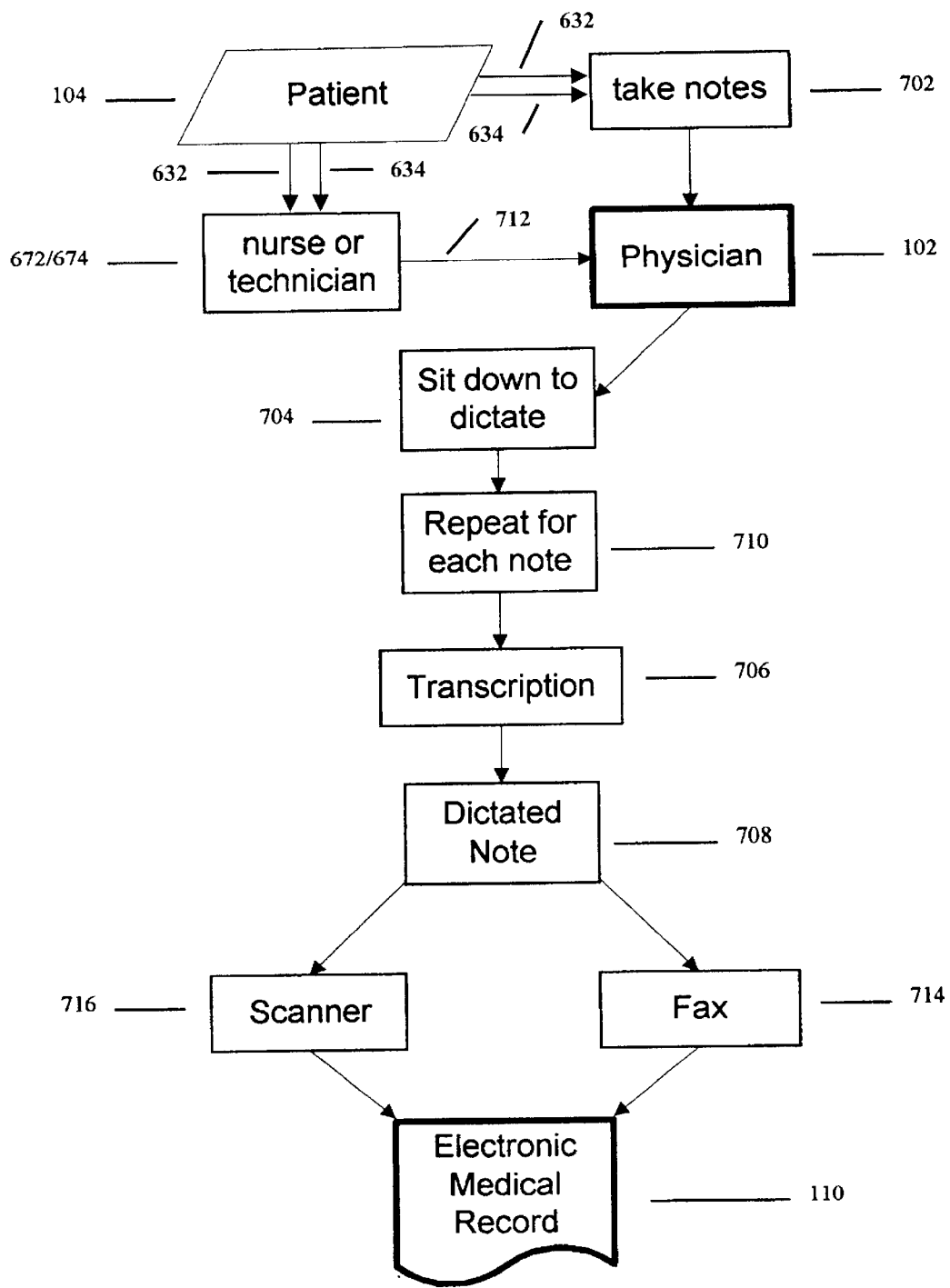
FIG. 45 is a flow chart which illustrates conventional steps to produce an electronic medical record.

Decreased Number of Steps—FIG. 45

The process of documentation with CaD can be compared to traditional methods of documentation which require several steps. This is especially true if the individual producing the document is mobile or if an electronic version of the document is desired. The following steps can be eliminated by the use of CaD:

1. If the user 102 is mobile it is often necessary to take preliminary notes 702 which can be referred to later.
2. If dictation is the method used the user 102 must sit down and verbally dictate 704 the record from notes and/or memory.
3. A transcriptionist must then type 706 the document 708.
4. Regardless of the method used, often times the user must repeat and regenerate identical words 710 and phrases for each individual document.
5. In the medical setting the operator (physician) often times must repeat information previously gathered 712 by other health care workers such as nurses 672 and technicians 674.
6. Once a document is produced there are usually extra steps required to convert to an electronic format. If one wishes to transmit the document it must be entered into a facsimile machine 714.
7. If one wishes to archive a document such as a medical record for later retrieval it is usually fed into an optical scanner 716.

Our invention has the advantage of eliminating each of these seven steps thus contributing greatly to the overall efficiency of the process. This results in an improved method of documentation of medical care. The CaD process can also be extended to other fields of expertise where documentation is required.

DESCRIPTION AND OPERATION OF ALTERNATIVE EMBODIMENTS

Field of Expertise

The computer assisted documentation software system (CaD) was originally created to facilitate the production of high quality medical records in a busy emergency department. This comprises the preferred embodiment. As an alternative embodiment, CaD could be used for other medical specialties as well. It could also be used to produce documents for nonmedical professionals including, but not limited to, attorneys, psychologists, journalists, etc.

Non-Expert Mode

In its preferred embodiment, the CaD system operates in "Expert mode". It is designed to help an expert user produce necessary documents quickly and easily. Expert mode means that the values of certain variables are defaulted or inferred. If the CaD program encounters a variable in such a state while executing in expert mode, them the CaD program does not stop and prompt the user for an answer. Instead it skips ahead to the next unanswered question. If the CaD program were executed in nonexpert mode this would be considered an alternative embodiment. A defaulted or inferred value would show up as a preselection on the pick list but the user would at least have to confirm the entry by striking the "OK" button. Non-Expert mode could be used to allow less experienced workers to function in place of more experienced ones. In this alternative embodiment, the CaD system can be used to walk a less experienced user through the interview. This assistant user thus serves as an "extender" of the more expert user. The nonexpert user can borrow upon the expertise of the original domain expert who produced the knowledge base.

Training Tool

One alternative embodiment of the CaD program would be use as a training tool. To again use the medical setting as the example, a medical student or intern can actually learn how to take a better medical history by using the CaD device. In this alternative embodiment, CaD functions as an expert system. Using CaD as a teaching tool would be considered an alternative embodiment.

Diagnostic Aid

Another alternative embodiment would be the use of CaD to enable a less experienced worker to staff a computer help desk or otherwise serve in a technical support role. A script would guide the worker through a series of diagnostic questions. However, several features of the program would not be utilized to their fullest potential in this mode of use. These features include interactive questions (multiple possibilities and combinations anticipated), inference defaults (different users), and text output capability (especially the grammar and document appearance commands) for example.

Other Operating Systems

In the preferred embodiment the CaD software runs under the Microsoft Windows© operating system. Modifying the program to run under another operating system such as OS/2, UNIX or WINDOWS NT©, or some other operating system would constitute an alternative embodiment.

Network Connections

In its preferred embodiment, the CaD system operates by connecting the hand-held computer device 130 to the desktop computer via wireless LAN 134. If two computers or a computer and a printer were networked via an infrared serial communication port, conventional hardwired LAN or any other serial communications device this would constitute an alternative embodiment. If the CaD system was run on a desktop system alone or operated on a network of several computers, this would be considered an alternative embodiment.

Delayed or Batch Printing

In its preferred embodiment, a mobile worker utilizes the CaD system to initiate the printing of documents at a location that may be physically distant. This is accomplished by transmitting the documents to the printer over a wireless LAN. If the documents were simply stored on a hard drive mass storage device in the hand held computer and printed as a batch print job, then this would be considered an alternative embodiment.

No Interview

In its preferred embodiment, the CaD system is used to conduct an interview of another individual. If the CaD software is used to record structured data which was not obtained as a result of an interview this would be considered an alternative embodiment.

Pen Substitutes

In its preferred embodiment, the CaD system operates by means of a digitizing pen 158 that transmits an electrical signal to a suitable LCD screen which is specially equipped to receive input signals. A touch screen that could receive input from a user's finger would be considered an alternative embodiment. Using the CaD program with a conventional mouse would also constitute an alternative embodiment.

Data Entry Methods

The use of alternate means of text and data entry such as the addition of speech recognition or use of a keyboard would be considered an alternative embodiment.

Variable State

In the preferred embodiment a significant measure of the sophisticated functionality of the CaD software system operates is due to the way the software tracks the "state" of a variable 272. This is described in the preceding section. Additional methods or schemes for naming, classifying or monitoring the "state" of a variable would be considered alternative embodiments.

Modal Dialog Data Entry Forms

The CaD program incorporates specially designed modal dialog forms 284. FIG. 12 for the entry of specific types of data. Numerical data can be entered quickly by pressing the appropriate buttons 286 on the screen 156. The number thus selected shows up in the display box 288. When all of the data is correct, it can be verified by clicking the "OK" button 290. Similar devices could be created for other specialized uses of the CaD system. Different modal dialog data entry forms would be considered alternative embodiments.

Additional Modes of Operation

In the preferred embodiment the CaD system operates in one of two modes expert and non-expert. Three user levels are recognized. Additional modes of operation or user levels would be considered alternative embodiments.

Inference

In the preferred embodiment, the CaD program can infer the value of a variable based upon the values of one or more other variable. There are four different methods to accomplish this task, each with subtle differences that add to the power and flexibility of the CaD system. Inferences can be based upon the mode of operation or the user's level as well. Different methods of inference would be considered alternative embodiments.

Alternative Naming Conventions

In the preferred embodiment, the nodes, lists, variables and sections are named with abbreviated and compounded names according to the particular profession being served. A different scheme or naming syntax for nodes, variable, and lists would be considered an alternative embodiment. All of the commands and functions in the knowledge base language could have different names. The various divisions of the knowledge base could be named differently. For example, we have chosen the name list for the items to choose from in a drop down pick list. In data base terminology this might be known as a table. Sometime such a list is known as a verification table. Alternate names for similar functions would be considered alternative embodiments.

Expert System Rules

Many so called "expert systems" incorporate sophisticated probability rules. These types of rules might be used, for example, to make a diagnosis based upon the data input. In the preferred embodiment the CaD program does not employ this level of complexity. If/then rules are in the form of equal to, not equal to, or greater than or less than. Probability rules could be added if desired. This would constitute an alternative embodiment.

Graphical User Interface

CaD operates in a Windows environment with a fairly conventional user interface. The user interface is just that, a means of enabling a user to communicate and interact with the CaD software. Alterations and modifications of the user interface would be considered alternative embodiments. Examples of such alterations include but are not limited to changes in layout, window size and shape, fonts, colors, buttons, tabs, menus. Different means of communicating information to the user and different means of user input would be considered alternative embodiments.

CONCLUSION, RAMIFICATIONS AND SCOPE

Thus, according to this invention, an improved method of producing technical documents is provided. Computer-assisted Documentation (CaD) may be considered to be a new type of computer application category. Alternative terms that could be used to describe this invention include: documentation technology, interview processor, computer directed interview, interactive document production, or data collection software. CaD causes a hand-held computing device to be transformed into a tool for collecting data by means of a guided interview. Within the computer, the collected data is sorted, saved, and recalled in the form of serialized persistent objects. This data can then be processed, output, or stored in such a way as to produce a high quality technical document. These documents are written in a narrative format according to the traditions and customs of the profession of the user. CaD uses a knowledge base script language with a unique syntax to accomplish this task.

In the preferred embodiment CaD is used to produce patient records in the field of emergency medicine. Health care represents a large expense to our nation, approximately 11% of GDP. Documentation of patient care represents an increasing burden to the practitioner. In the present "information" age there is a great need to manage medical records in a more efficient fashion. This is commonly referred to as the "Electronic Medical Record". Until now, attempts to create such records have been clumsy and redundant. CaD introduces a novel method for the efficient production of medical records efficiently.

While the descriptions in the preceding sections of this application identify many specific functions of CaD, these should not be construed as limitations on the scope of the invention. These previously noted descriptions should rather be considered as exemplifications of the presently preferred embodiments. Many more ramifications are possible within the teachings of the invention. These include multiple variations in the means of printing and transmittal of documents, and the use or non-use of adjuncts such as transcription. Other means by which the embodiment could be altered include: mobile vs. stationary computing devices, different operating systems, or a different user interface. Specifically, this invention could be used in fields other than medicine, such as law, allied health professions, psychology, law enforcement, fire and EMS departments, journalism, and technical support in a variety of settings. Thus, the full scope of the invention should be determined not by the examples given, but by the appended claims and their legal equivalents.

We claim:

1. A document generation system for the purpose of creating technical or professional documents comprising:
   a. a mobile computing device incorporating a user interface device for entering data in various locations, said data entered pursuant to a menu driven user interface wherein choices can be selected quickly so as to make use of said mobile computing device;
   b. wherein said menu driven user interface is a guided interview wherein: the user is asked a series of question posed by said system and the subsequent questions asked vary in response to answers previously given;
   c. a programmable and reusable knowledge base which is distinct from any execution program accessible by said mobile computing device such that, said programmable knowledge base is defined by a script language such that the user can perform modification of the knowledge base resulting in alteration of the final document; and further comprises a navigation means for routing or guiding the user through the interview.

2. The system of claim 1, further comprising:
   a bi-directional inference means for producing medical records, the bi-directional inference means containing the following elements:
   multiple variable elements which may contain single or multiple variable values;
   variable states which track user information;
   rule elements which execute various actions such as screen display, text output, user prompts and pick lists depending upon the values of the variables; and
   inference tables which reset or infer the values of multiple variables based upon the input value of a single variable;
   the bi-directional inference means modifying the knowledge base such that the final document may be altered in a forward direction by entering answers to the questions asked in the guided interview and in a reverse direction by entering a medical diagnosis.

3. A document generation system for the purpose of creating technical or professional documents comprising:
   a. a mobile computing device incorporating a user interface device for entering data in various locations, said data entered pursuant to a menu driven user interface wherein choices can be selected quickly so as to make use of said mobile computing device;
   b. wherein said menu driven user interface is guided interview wherein: the user is asked a series of questions posed by said system and the subsequent questions asked vary in response to answers previously given;
   c. a programmable and reusable knowledge base which is distinct from any execution program accessible by said mobile computing device further comprising a drawing means whereby additions in the form of bit mapped images may be:
   displayed on the screen;
   edited by the user; and
   incorporated into the final document produced.

* * * * *